United States Patent
Kato et al.

(10) Patent No.: US 8,980,183 B2
(45) Date of Patent: Mar. 17, 2015

(54) APPARATUS AND METHOD FOR PRODUCING CATALYST, AND METHOD FOR PRODUCING UNSATURATED ACID OR UNSATURATED NITRILE

(75) Inventors: Takaaki Kato, Tokyo (JP); Satoshi Endo, Tokyo (JP); Minoru Kadowaki, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 0 days.

(21) Appl. No.: 13/991,991

(22) PCT Filed: Dec. 13, 2011

(86) PCT No.: PCT/JP2011/078798
§ 371 (c)(1),
(2), (4) Date: Jun. 6, 2013

(87) PCT Pub. No.: WO2012/081578
PCT Pub. Date: Jun. 21, 2012

(65) Prior Publication Data
US 2013/0253216 A1    Sep. 26, 2013

(30) Foreign Application Priority Data

Dec. 17, 2010 (JP) .................. 2010-282346
Jan. 14, 2011 (JP) .................. 2011-006328

(51) Int. Cl.
*B01J 19/00* (2006.01)
*C07C 253/24* (2006.01)
*C07C 253/26* (2006.01)
(Continued)

(52) U.S. Cl.
CPC .............. *B01J 23/28* (2013.01); *C07C 253/24* (2013.01); *C07C 253/26* (2013.01); *B01J 37/12* (2013.01);
(Continued)

(58) Field of Classification Search
CPC .......... B01J 20/00; B01J 20/02; B01J 20/003; B01J 20/0214; B01J 20/0216; B01J 23/16; B01J 23/20; B01J 23/22; B01J 23/24; B01J 23/28; B01J 23/54; B01J 23/56; B01J 23/64; B01J 23/648; B01J 23/6482; B01J 23/6484; B01J 23/652; B01J 23/6525; B01J 2531/50; B01J 2531/56; B01J 2531/57; B01J 2531/60; B01J 2531/64; B01J 19/00; B01J 19/24
USPC .................. 422/129, 187, 211; 502/300, 305, 502/311–313
See application file for complete search history.

(56) References Cited

U.S. PATENT DOCUMENTS 4,499,197 A * 2/1985 Seese et al. .............. 502/65
4,542,118 A * 9/1985 Nozemack et al. ........ 502/65
(Continued)

FOREIGN PATENT DOCUMENTS

JP    7-315842 A    12/1995
JP    8-141401 A    6/1996
(Continued)

OTHER PUBLICATIONS

International Search Report issued in PCT/JP2011/078798, mailed on Mar. 6, 2012.

*Primary Examiner* — Natasha Young
(74) *Attorney, Agent, or Firm* — Birch, Stewart, Kolasch & Birch, LLP

(57) ABSTRACT

An apparatus for producing a catalyst comprising a tank configured to prepare an aqueous mixed solution containing a Mo compound, a V compound and a Nb compound, a dryer configured to spray-dry the aqueous mixed solution, and a pipe for connecting the tank with the dryer so that the aqueous mixed solution can be supplied from the tank to the dryer, wherein a heater configured to heat the aqueous mixed solution is provided in the tank and/or the pipe, and a filter configured to filtrate the aqueous mixed solution is provided in the pipe.

20 Claims, 6 Drawing Sheets

(51) Int. Cl.
  *B01J 37/12* (2006.01)
  *B01J 23/00* (2006.01)
  *B01J 35/02* (2006.01)
  *B01J 37/00* (2006.01)
  *B01J 23/16* (2006.01)
  *B01J 23/20* (2006.01)
  *B01J 23/22* (2006.01)
  *B01J 23/24* (2006.01)
  *B01J 23/28* (2006.01)
  *B01J 23/54* (2006.01)
  *B01J 23/56* (2006.01)
  *B01J 23/64* (2006.01)
  *B01J 23/648* (2006.01)
  *B01J 23/652* (2006.01)
  *B01J 20/00* (2006.01)
  *B01J 20/02* (2006.01)
  *B01J 35/00* (2006.01)

(52) U.S. Cl.
  CPC .............. *B01J 23/002* (2013.01); *B01J 35/023* (2013.01); *B01J 37/0018* (2013.01); *B01J 37/0045* (2013.01); *B01J 35/002* (2013.01); *B01J 2523/00* (2013.01)

USPC ........... 422/129; 422/187; 422/211; 502/100; 502/300; 502/305; 502/311; 502/312; 502/313

(56) References Cited

U.S. PATENT DOCUMENTS

| | | | |
|---|---|---|---|
| 6,036,880 A * | 3/2000 | Komada et al. | 252/183.13 |
| 6,610,629 B2 * | 8/2003 | Hinago et al. | 502/300 |
| 7,667,073 B2 * | 2/2010 | Dieterle et al. | 562/535 |
| 2005/0107252 A1 * | 5/2005 | Gaffney et al. | 502/355 |
| 2007/0203022 A1 | 8/2007 | Schlogl et al. | |
| 2011/0288325 A1 | 11/2011 | Ishii et al. | |

FOREIGN PATENT DOCUMENTS

| | | |
|---|---|---|
| JP | 2003-181287 A | 7/2003 |
| JP | 2003-210982 A | 7/2003 |
| JP | 2007-117818 A | 5/2007 |
| JP | 2008-506522 A | 3/2008 |
| JP | 2009-148749 A | 7/2009 |
| JP | 2011-5364 A | 1/2011 |
| TW | 2010-41649 A1 | 12/2010 |

* cited by examiner

APPARATUS AND METHOD FOR PRODUCING CATALYST, AND METHOD FOR PRODUCING UNSATURATED ACID OR UNSATURATED NITRILE

The present application is a National Stage Phase entry of PCT Application No. PCT/JP2011/078798, filed Dec. 13, 2011, which claimed priority to Japanese Application No. 2010-262346, filed Dec. 17, 2010, and Japanese Application No. 2011-006328, filed Jan. 14, 2011, the disclosures of which are hereby incorporated by reference in their entireties.

BACKGROUND OF THE INVENTION

1. Field of the Invention

The present invention relates to an apparatus and a method for producing a catalyst, and a method for producing an unsaturated acid or an unsaturated nitrile.

2. Description of the Related Art

Previously, a method of subjecting propane or isobutane to a vapor-phase catalytic oxidation or vapor-phase catalytic ammoxidation reaction, so as to produce a corresponding unsaturated carboxylic acid or unsaturated nitrile, has attracted attention, and various types of oxide catalysts preferably used in such production have been proposed.

As a method for producing an oxide catalyst containing a Mo compound, a V compound and a Nb compound, there has been known a technique for obtaining an oxide catalyst by preparing an aqueous mixed solution, then spray-drying this mixed solution and then calcining it. In a mixed solution consisting of niobium and multiple types of other metal ions, individual metal ions have each different pH stable ranges. Thus, such a mixed solution has extremely low stability as a solution, and precipitation easily takes place. In particular, in a case in which an aqueous mixed solution contains Mo—V—Nb—(Te/Sb), such an aqueous mixed solution has a characteristic that it extremely easily becomes gelatinous under non-stirred conditions. Hence, there may be a risk that the composition of ingredients may become uneven in a local region in which stirring is insufficient, and that a decrease in catalytic performance may thereby occur. In addition, there may also be a case in which it becomes impossible to supply the prepared aqueous mixed solution to a spray dryer.

In order to prevent the aforementioned phenomenon, for example, Patent Document 1 describes a method for supplying an aqueous mixed solution to a pipe by controlling a retention time in a preparation step and/or a drying step. Moreover, Patent Document 2 discloses a method for controlling a non-stirring time in the preparation step. Furthermore, Patent Document 3 states that a stirring power is controlled within a constant range during the preparation step.

CITATION LIST

Patent Documents

[Patent Document 1] Japanese Patent Application Laid-Open No. 2003-181287
[Patent Document 2] Japanese Patent Application Laid-Open No. 2003-210982
[Patent Document 3] Japanese Patent Application Laid-Open No. 2007-117818

SUMMARY OF THE INVENTION

Problems to be Solved by the Invention

According to the methods described in Patent Documents 1 to 3, an aqueous mixed solution is certainly in a substantially resting state over a long period of time, so that it can be prevented from becoming gelatinous. However, even if such an aqueous mixed solution has been prevented from becoming gelatinous, a portion of the aqueous mixed solution may become gelatinous. In particular, when such an aqueous mixed solution is industrially produced, there may be cases in which a pipe for supplying the prepared aqueous mixed solution to a spray dryer includes portions in which the solution is easily retained, or in which it takes a long time from preparation of the aqueous mixed solution to the spray-drying thereof. As a result, the aqueous mixed solution easily becomes gelatinous. If the gelled aqueous mixed solution is directly supplied to the spray dryer, clogging may be generated in the midcourse thereof. Moreover, even if the aqueous mixed solution can be supplied to the spray dryer, there may be a case in which clogging is generated in the spray dryer and thus it becomes difficult to carry out spray-drying. If a small amount of aqueous mixed solution is prepared in a laboratory, the mixed solution is, for example, heated, so that it can be returned to a fluidized state again. However, in a case in which the mixed solution is prepared during continuous steps, it is difficult to heat the gelled aqueous mixed solution.

Hence, the present invention has been completed under the above-mentioned circumstances, and it is an object of the present invention to provide an apparatus and a method for producing a catalyst, which are capable of smoothly supplying the prepared aqueous mixed solution to a dryer, and a method for producing an unsaturated acid or an unsaturated nitrile using the aforementioned a catalyst.

Means for Solving the Problems

As a result of intensive studies directed towards achieving the aforementioned object, the present inventors have discovered that the clogging of a pipe and a spray dryer can be prevented by providing a heating unit in a mixed solution tank for preparing an aqueous mixed solution containing a Mo compound, a V compound and a Nb compound and/or a pipe for supplying the mixed solution from the mixed solution tank to a spray dryer, and also by providing a filtration unit in the pipe to remove a solid and/or a gelled product, thereby achieving the present invention.

Specifically, the present invention is as follows.

[1] An apparatus for producing a catalyst, comprising a tank configured to prepare an aqueous mixed solution containing a Mo compound, a V compound and a Nb compound, a dryer configured to spray-dry the aqueous mixed solution, and a pipe for connecting the tank with the dryer so that the aqueous mixed solution can be supplied from the tank to the dryer, wherein
a heater configured to heat the aqueous mixed solution is provided in the tank and/or the pipe, and a filter configured to filtrate the aqueous mixed solution is provided in the pipe.
[2] The apparatus for producing a catalyst according to [1] above, wherein at least a part of an inner surface of the tank and/or an inner surface of the pipe consist of a fluorocarbon resin.
[3] The apparatus for producing a catalyst according to [1] or [2] above, wherein a cooler configured to cool the aqueous mixed solution is provided in the tank.
[4] The apparatus for producing a catalyst according to [3] above, wherein at least a part of a region of the heater and/or the cooler provided in the tank, the region being allowed to come into contact with the aqueous mixed solution, consist of a fluorocarbon resin.

[5] The apparatus for producing a catalyst according to any one of [1] to [4] above, comprising, inside the tank, a washer configured to wash an inner surface of the tank.

[6] The apparatus for producing a catalyst according to [5] above, wherein the washer is configured to spray and/or inject water into the tank so that the water is allowed to come into contact with the inner surface of the tank.

[7] The apparatus for producing a catalyst according to any one of [1] to [6] above, comprising a plurality of the tanks, wherein the tanks are configured so that the aqueous mixed solution prepared in one or more of the tanks is spray-dried by the dryer, and thereafter, the aqueous mixed solution prepared in other one or more of the tanks that are different from the former one or more of the tanks is spray-dried by the dryer.

[8] A method for producing a catalyst using the apparatus for producing a catalyst according to any one of [1] to [7] above, comprising:
(a) a step of preparing an aqueous mixed solution containing a Mo compound, a V compound and a Nb compound; and
(b) a step of drying the aqueous mixed solution by a dryer,
wherein the apparatus for producing a catalyst comprises a plurality of tanks, and
the method comprises:
a step of, while spray-drying the aqueous mixed solution from one or more of the tanks, further preparing the aqueous mixed solution in other one or more of the tanks that are different from the former one or more of the tanks; and
a step of continuously spray-drying the aqueous mixed solution by supplying the aqueous mixed solution prepared in the other one or more of the tanks to the dryer and spray-drying the aqueous mixed solution, after the aqueous mixed solution from the former one or more of the tanks has been spray-dried.

[9] A method for producing a catalyst using the apparatus for producing a catalyst according to any one of [1] to [7] above, wherein the catalyst has a composition represented by the following formula (1):

$$MoV_aNb_bX_cT_dZ_eO_n \quad (1)$$

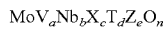

(wherein X represents one or more elements selected from the group consisting of Sb, Te, Sr, Ba, Sc, Y, La, Ce, Pr, Yb, W, Cr, Ta, Ti, Zr, Hf, Mn, Re, Fe, Ru, Co, Rh, Ni, Pd, Pt, Ag, Zn, B, Al, Ga, In, Ge, Sn, Pb, P, Bi, rare earth elements and alkaline earth elements; T represents one or more elements selected from the group consisting of Ti, Zr, Hf, Ta, Cr, W, Mn, Re, Fe, Co, Ni, Au, Zn, B, Al, Ga, In, Ge, Sn, Pb, P and Bi; Z represents one or more elements selected from the group consisting of La, Ce, Pr, Yb, Y, Sc, Sr and Ba; a, b, c, d and e are within the ranges of $0.01 \leq a \leq 1$, $0.01 \leq b \leq 1$, $0.01 \leq c \leq 1$, $0 \leq d < 1$, and $0 \leq e < 1$, respectively; and n is a value satisfying the balance of valences).

[10] The method for producing a catalyst according to [8] above, wherein the catalyst has a composition represented by the following general formula (1):

$$MoV_aNb_bX_cT_dZ_eO_n \quad (1)$$

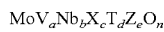

(wherein X represents one or more elements selected from the group consisting of Sb, Te, Sr, Ba, Sc, Y, La, Ce, Pr, Yb, W, Cr, Ta, Ti, Zr, Hf, Mn, Re, Fe, Ru, Co, Rh, Ni, Pd, Pt, Ag, Zn, B, Al, Ga, In, Ge, Sn, Pb, P, Bi, rare earth elements and alkaline earth elements; T represents one or more elements selected from the group consisting of Ti, Zr, Hf, Ta, Cr, W, Mn, Re, Fe, Co, Ni, Au, Zn, B, Al, Ga, In, Ge, Sn, Pb, P and Bi; Z represents one or more elements selected from the group consisting of La, Ce, Pr, Yb, Y, Sc, Sr and Ba; a, b, c, d and e are within the ranges of $0.01 \leq a \leq 1$, $0.01 \leq b \leq 1$, $0.01 \leq c \leq 1$, $0 \leq d < 1$, and $0 \leq e < 1$, respectively; and n is a value satisfying the balance of valences).

[11] A method for producing an unsaturated acid or an unsaturated nitrile, comprising carrying out a vapor-phase catalytic oxidation reaction or vapor-phase catalytic ammoxidation reaction of propane or isobutane so as to produce a corresponding unsaturated acid or unsaturated nitrile,
wherein a catalyst obtained by the method for producing a catalyst according to any one of [8] to [10] above is used.

Advantages of the Invention

According to the present invention, there can be provided an apparatus and a method for producing a catalyst, which are capable of smoothly supplying the prepared aqueous mixed solution to a dryer, and a method for producing an unsaturated acid or an unsaturated nitrile using the aforementioned catalyst.

DETAILED DESCRIPTION OF THE PREFERRED EMBODIMENTS

Figure 1:
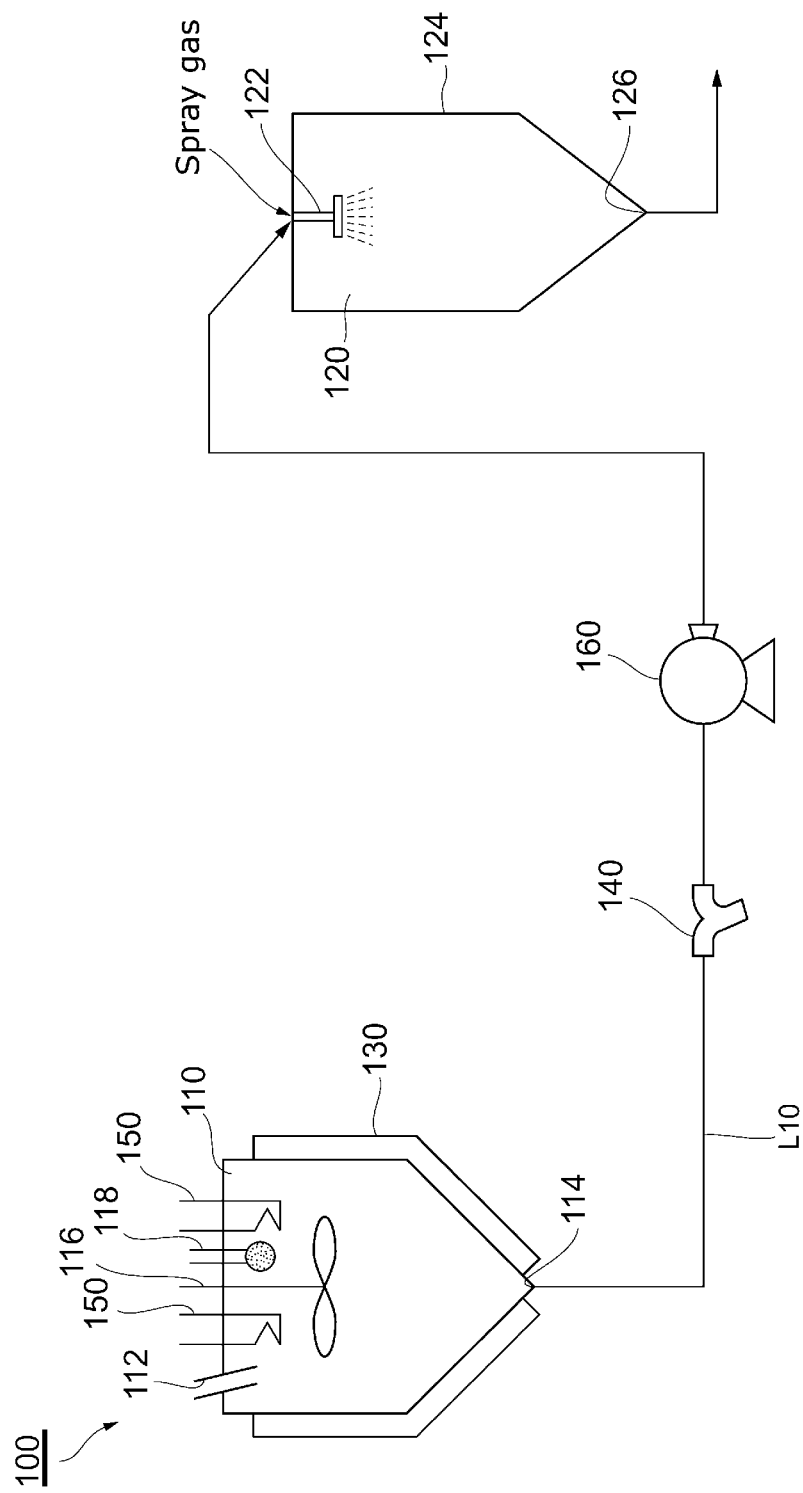
FIG. 1 is a partial schematic view showing an example of the apparatus for producing a catalyst of the present embodiment.

Hereinafter, the embodiment for carrying out the present invention (hereinafter abbreviated as "the present embodiment") will be described in detail, while referring to drawings, as necessary. It is to be noted that the present invention is not limited to the following embodiment, and that it can be carried out in various modifications within the range of the gist thereof. In addition, the same symbol is given to the same element in the drawings, so that overlapped explanations are omitted. The positional relationships (upper, lower, left, right positions, etc.) are based on the positional relationships shown in the drawings, unless otherwise specified. Moreover, the dimensional ratios used in the drawings are not limited to the ratios shown in the drawings. In the present specification, the Japanese term "chogo (preparation)" has the same meaning as that of the Japanese term "chosei (preparation)."

The apparatus for producing a catalyst (hereinafter simply referred to as a "production apparatus" or a "catalyst-producing apparatus" at times) of the present embodiment comprises a tank configured to prepare an aqueous mixed solution containing a Mo compound, a V compound and a Nb compound, a dryer configured to spray-dry the aqueous mixed solution, and a pipe for connecting the tank with the dryer so that the aqueous mixed solution can be supplied from the tank to the dryer, wherein a heater configured to heat the aqueous mixed solution is provided in the tank and/or the pipe, and a filter configured to filtrate the aqueous mixed solution is provided in the pipe.

FIG. 1 is a partial schematic view showing an example of the apparatus for producing a catalyst of the present embodiment. This production apparatus 100 comprises a mixed solution tank 110, a dryer 120, and a pipe L10 for connecting them. The mixed solution tank 110 is used to prepare an aqueous mixed solution containing a Mo compound, a V compound and a Nb compound. In addition, the mixed solution tank 110 may be configured to preserve (store) the aqueous mixed solution. The dryer 120 is configured to spray-dry the aqueous mixed solution. The pipe L10 connects the mixed solution tank 110 with the dryer 120, so that the aqueous mixed solution prepared in the mixed solution tank 110 can be supplied to the dryer 120.

Temperature control devices 130 and 150 are provided in the mixed solution tank 110, and such a temperature control device is also provided in the pipe L10 (not shown in the figure). A filter 140 is provided in the pipe L10. The prepared aqueous mixed solution, which has been heated by the temperature control devices 130 and 150 in the mixed solution tank 110, is heated by the temperature control device provided in the pipe L10, is then filtrated by the filter 140, is then supplied to the dryer 120.

In the production apparatus 100, the mixed solution tank 110 has a raw material supplying port 112 and an aqueous mixed solution discharging port 114, and it also has a stirrer 116 and a washing device 118. The raw material supplying port 112 is a supplying port for supplying each ingredient used as a raw material for the aqueous mixed solution into the mixed solution tank 110. The aqueous mixed solution discharging port 114 is a discharging port for discharging the prepared aqueous mixed solution to the pipe L10.

As the temperature control devices 130 and 150, known temperature control devices may be used, as long as they are able to heat or cool the aqueous mixed solution so as to control the temperature of the aqueous mixed solution in the mixed solution tank 110. Thus, the type of the temperature control device is not particularly limited. One of the temperature control devices 130 and 150 may be a heater having only heating function, and the other may be a heater or a heating-cooling device having both heating and cooling functions. Otherwise, the two devices may be both heating-cooling devices. Otherwise, one of the temperature control devices 130 and 150 may be a cooler having function to cool the aqueous mixed solution. In such a case, the other device is a heating-cooling device or a heater. The temperature control device 130 heats or cools the mixed solution tank 110 from the environment thereof, so as to control the temperature of the aqueous mixed solution contained therein. In contrast, the temperature control device 150 is allowed to directly come into contact with the aqueous mixed solution in the mixed solution tank 110 so as to control the temperature thereof. The temperature control devices 130 and 150 may utilize a heating medium such as water vapor and a cooling medium such as water, as with a heat exchanger, and the devices may also be electrical heaters.

In order to prevent adhesion of the aqueous mixed solution, members displaced on the inner surface of the mixed solution tank 110 and inside the mixed solution tank 110, and materials constituting the apparatus, are preferably materials capable of reducing the friction of the inner surface. Examples of such a preferred material include a fluorocarbon resin, a glass and a silicon resin. In particular, on the surface of the temperature control device 150, which easily reaches a high temperature, fouling caused by the adhering aqueous mixed solution is easily solidified in a short time. Thus, from the viewpoint of easy removal of such a solidified product, at least a portion of the region more preferably consists of a fluorocarbon resin.

Figure 2:
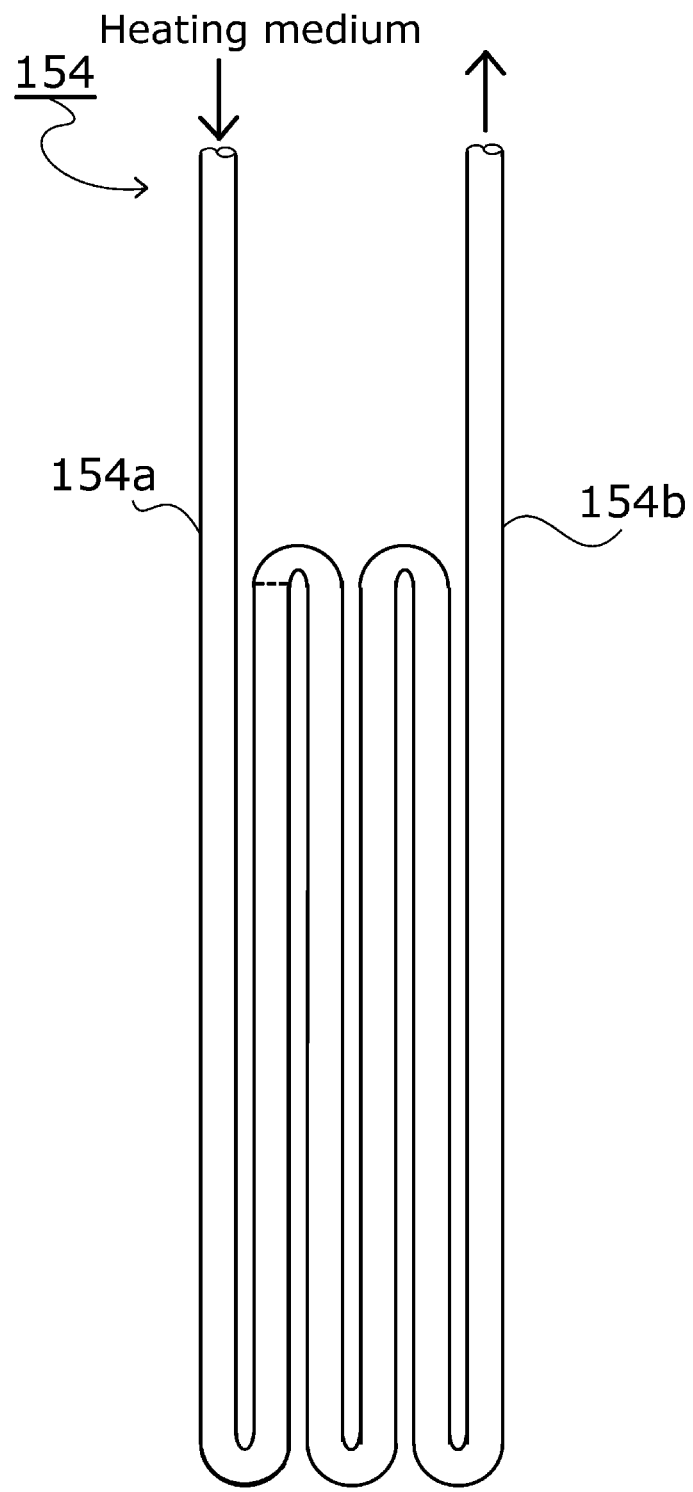
FIG. 2 is a schematic view showing an example of a temperature control device 150 shown in FIG. 1.

FIG. 2 is a schematic view showing a heat-transfer pipe that is a member of a heat exchanger, in a case in which the temperature control device 150 is a heat exchanger for heating the aqueous mixed solution by heat exchange with a heating medium. A heating medium (for example, water, benzyl alcohol, ethylene glycol, toluene, and silicon oil) is supplied into the pipe of this heat-transfer pipe 154, and thus, the aqueous mixed solution allowed to come into contact with the outer surface of the heat-transfer pipe 154 is heated by the heat transferred from the heating medium via the heat-transfer pipe 154. In the heat-transfer pipe 154, in a region 154a on the side upstream of the supplying direction of the heating medium, the heating medium has a higher temperature. Thus, there is a large difference in temperature from the aqueous mixed solution. As a result, the surface of the region 154a easily becomes dirty. Hence, from the aforementioned viewpoint, the outer surface of the region 154a preferably consists of a fluorocarbon resin. On the other hand, a region 154b on the side downstream of the supplying direction of the heating medium in the heat-transfer pipe 154, in which the temperature of the heating medium has decreased as a result of heat exchange with the aqueous mixed solution, preferably consists of a material with high thermal conductivity in order to further increase its heat exchange efficiency. Examples of such a material include stainless steel and carbon steel. From the same viewpoint as described above, it is more preferable that the heat-transfer pipe 154 consist of a material with the above described high thermal conductivity, and that the outer surface of the region 154a on the side upstream of the supplying direction of the heating medium be coated with a fluorocarbon resin.

In order to supply the aqueous mixed solution from the mixed solution tank 110 to the dryer 120, a pump 160 is preferably provided in the midcourse of the pipe L10. The embodiment of the pump 160 is not particularly limited, as long as it is able to supply the aqueous mixed solution. Examples of such a pump include a screw pump, a uniaxial eccentric screw pump, a centrifugal pump, and a piston pump. For the purpose of preventing an increase in the temperature of the aqueous mixed solution and deterioration, and also for the purpose of preventing a pulsating flow, a uniaxial eccentric screw pump is preferably used. Moreover, if such a uniaxial eccentric screw pump is used, a buffer tank used for prevention of a pulsating flow becomes unnecessary, and as a result, clogging caused by an increase in the viscosity of the aqueous mixed solution in the buffer tank and/or the pipe can be suppressed.

The capacity of the pump is not particularly limited. The discharge rate thereof is preferably 10 to 300 L/hr, and the discharge pressure thereof is preferably 0.1 to 5.0 MPa.

The stirrer 116 may be disposed such that it can stir the aqueous mixed solution in the mixed solution tank 110. Herein, the term "stir" is used in the present specification to mean the action to move the after-mentioned aqueous solvent or aqueous mixed solution. The type of the stirrer 116 is not particularly limited, as long as it is able to stir a substance having fluidity. A known stirrer may be used. The stirrer 116 may comprise common mixer blades, impellers, and the like. Specifically, the stirrer 116 may comprise a multistage blade, a multistage pitched blade, an anchor blade, a helix blade, or a helical band blade, for example. Moreover, the stirrer 116 may also comprise, as a mixer blade for low-viscosity solution, a propeller, a disk turbine, a fan turbine, a curved vane fan turbine, a feather turbine, or an angle vane turbine, for example. Of these, a multistage pitched blade is preferable from the viewpoint of the control of a stirring power. Furthermore, the mixer blade used in the stirrer 116 is preferably a blade that can be immersion in the solution up to the lower portion of the mixed solution tank 110. When the mixed solution tank 110 has an inclination at the bottom thereof, the stirrer 116 more preferably has a small impeller that is suitable for the inclination.

The power (hereinafter referred to as "Pv") of the mixer blade of the stirrer 116 that is given per unit volume of the aqueous mixed solution in the mixed solution tank 110 is represented by a formula (A) as described below. A preferred Pv is 0.005 to 300 kW/m$^3$, more preferably 0.01 to 280 kW/m$^3$, and further preferably 0.1 to 250 kW/m$^3$.

By maintaining the Pv at 0.005 to 300 kW/m$^3$, clogging in the pipe caused by gelation of the aqueous mixed solution can be prevented more effectively, and at the same time, generation of depressions in dry particles obtained by spray-drying can also be prevented more effectively. Since the presence of such depressions causes a reduction in the strength of an oxide catalyst obtained after calcination, generation of the depressions can be preferably suppressed. The Pv can be controlled by regulating a solution density, the amount of the aqueous mixed solution, the number of rotation of the mixer blade, etc.

$$Pv = Np \times \rho \times n^3 \times d^5 / V \quad (A)$$

Herein, the symbols used in the formula (A) have the following meanings:

Np: Power number (–) that is a dimensionless number regarding a power necessary for stirring
$\rho$: Solution density (kg/m$^3$)
n: Number of rotation (s$^{-1}$) of the mixer blade
d: Diameter (m) of the mixer blade
V: Amount (m$^3$) of the aqueous mixed solution Np can be calculated using the following calculation expression (B1).

[Expression 1]

$$Np = \frac{A}{Re} + B \left( \frac{10^3 + 1.2 Re^{0.66}}{10^3 + 3.2 Re^{0.66}} \right)^p \times \left( \frac{Z}{D} \right)^{(0.35 + b/D)} \times (\sin\theta)^{1.2} \quad (B1)$$

wherein $$A = 14 + (b/D)\{670(d/D - 0.6)^2 + 185\} \quad (B2)$$

$$B = 10^{\{1.3 - 4(b/D - 0.5)^2 - 1.14(d/D)\}} \quad (B3)$$

$$p = 1.1 + 4(b/D) - 2.5(d/D - 0.5)^2 - 7(b/D)^4 \quad (B4)$$

$$Re = 10^{4(1-\sin\theta)} \times (25/(b/D) \times (d/D - 0.4)^2 + [(b/D)/\{0.11(b/D) - 0.0048\}]) \quad (B5)$$

Herein, the symbols used in the Expressions (B1) to (B5) have the following meanings:

b: Width [m] of the mixer blade
d: Diameter [m] of the mixer blade
D: Diameter [m] of the stirring tank
Z: depth [m] of the solution
$\theta$: Angle of inclination [deg] from the horizontal surface of the mixer blade The viscosity of the aqueous mixed solution during stirring is preferably 1 to 100 cp, more preferably 2 to 90 cp, and further preferably 2.5 to 80 cp.

The viscosity of the aqueous mixed solution can be measured, for example, by a method of measuring the viscosity using a commercially available viscometer or a method of measuring a pressure loss in the pipe for supplying the aqueous mixed solution. When the viscosity of a solution whose gelation gradually progresses in an non-stirred state is measured, there is a possibility that the viscosity gradually changes upon the measurement using a commercially available viscometer. Thus, from the viewpoint of reproducibility of the measurement value, the viscosity is preferably measured by the method of measuring a pressure loss in the pipe for supplying the aqueous mixed solution.

When the viscosity of the aqueous mixed solution is measured by the method of measuring a pressure loss in the pipe for supplying the aqueous mixed solution, the viscosity can be calculated by the following calculation expression (C1):

[Expression 2]

$$\mu = \frac{9.8 \times \Delta P \times D^2}{32 \times 10^{-3} \times uL} \quad (C1)$$

Herein, the symbols used in the formula (C1) have the following meanings:

$\Delta P$: Pressure loss (mmH$_2$O) in the pipe
$\mu$: Solution viscosity (cp)
u: Average solution supplying rate (m/s)
L: Pipe length (m)
D: Pipe diameter (m)

Moreover, when aqueous mixed solution is a complete aqueous solution, and no solids are generated by precipitation or the like during the spray-drying operation, preferred ranges of the upper and lower limits of Pv are not particularly limited.

A washing device 118 is preferably disposed in an upper portion of the mixed solution tank 110. The washing device 118 sprays and/or injects water, and allows the water to come into contact with the inner surface of the mixed solution tank 110, so as to wash out fouling caused by the aqueous mixed solution attached to the inner surface of the mixed solution tank 110. The type of the washing device 118 is not particularly limited, as long as it has such function to wash out fouling. A known washing device may be used. From the viewpoint of an increase in the washing effect, the linear velocity of water to be sprayed and/or injected is preferably 0.1 m/s or higher. Moreover, the water is preferably sprayed and/or injected for 5 minutes or longer. From the same viewpoint as described above, a plurality of the washing devices 118 are preferably provided in the mixed solution tank 110.

From the viewpoint of an increase in the washing efficiency, the washing device 118 is preferably able to spray and/or inject water in multiple directions. In particular, the upper lateral side of the inner surface of the mixed solution tank 110 is hardly allowed to come into contact with the aqueous mixed solution. Thus, if fouling caused by the aqueous mixed solution is attached thereto due to dispersion of liquid droplets or the like, they are solidified by unintended heating, and as a result, it is hardly removed. Accordingly, the washing device 118 is more preferably a device capable of reliably washing such a portion.

After completion of the production of a catalyst, or after all of the aqueous mixed solution has been discharged from the mixed solution tank 110 after completion of preparation of the aqueous mixed solution (wherein the after-mentioned drying of the aqueous mixed solution or calcination of a dry product may be carried out during this operation), it is effective, if hot water at approximately 50° C. is poured into the mixed solution tank 110 and it is then stirred to remove fouling. Moreover, it is more effective, if the water obtained after washing is supplied to the dryer 120 and it is then sprayed therein, because the pipe L10, the pump 160 and the dryer 120 can also be washed with the water.

Figure 3:
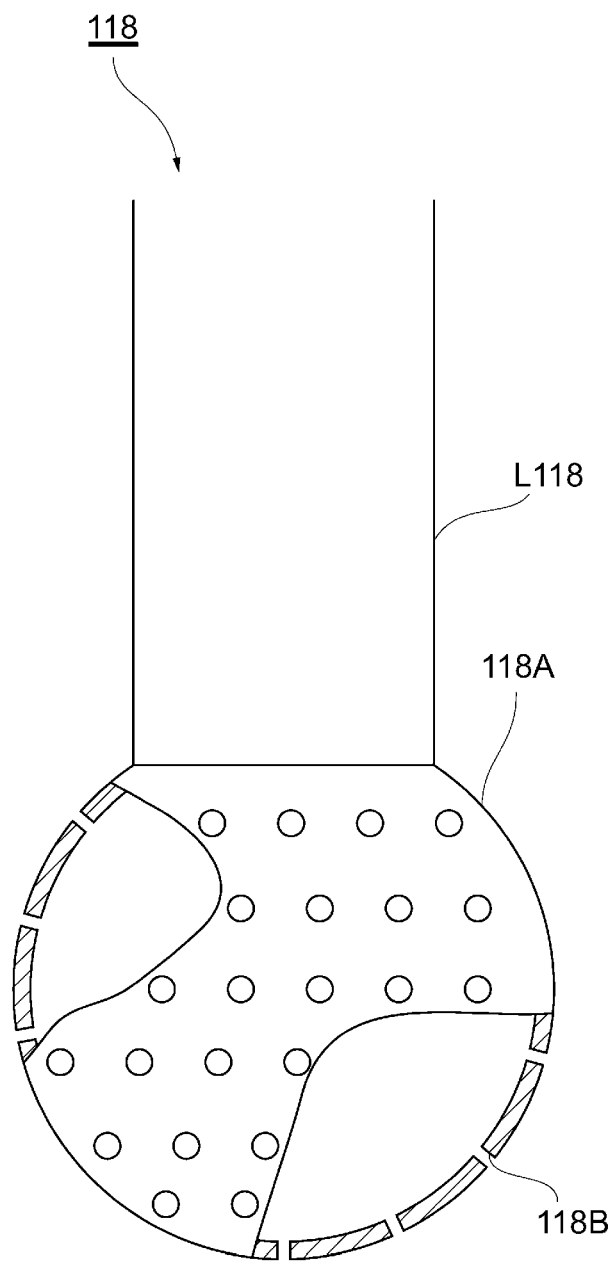
FIG. 3 is a partial cross-sectional view schematically showing an example of a washing device.

FIG. 3 is a partial cross-sectional view schematically showing an example of the washing device 118. The washing device 118 comprises a spherical spray nozzle 118A and a pipe L118 for supplying water to the spray nozzle 118A. The spray nozzle 118A is a hollow spherical form, and it has a plurality of through-holes 118B on the surface of the spherical form thereof. Water supplied via the pipe L118 to the spray nozzle 118A is sprayed and/or injected through the through-holes 118B into the mixed solution tank 110. The water may also be sprayed and/or injected by a pressure difference between the inside and outside of the spray nozzle 118A, namely, by setting the pressure inside the spray nozzle 118A higher than the pressure outside the spray nozzle 118A. Alternatively, the water may also be sprayed and/or injected by centrifugal force generated by rotation of the washing device 118 having the axis of the pipe L118 as a center.

The pipe L10 is a device for supplying the aqueous mixed solution or water, which connects the mixed solution tank 110 with the dryer 120. The material for the pipe L10 is not particularly limited. For example, a fluorocarbon resin, a glass, or a silicon resin can be used. Of these, a fluorocarbon resin is preferable because fouling is hardly attached thereto. Moreover, for the purpose of preventing the clogging of the pipe due to accumulation of fouling, two or more systems of the pipes L10 for connecting the mixed solution tank 110 with the dryer 120 are preferably provided, although they are not shown in the figure. A temperature control device (not shown in the figure) is provided in a part of or the entire pipe L10. The temperature control device has at least heating function, and it preferably has cooling function as well. For the purpose of preventing an increase in the viscosity of the aqueous mixed solution, and also for the purpose of preventing the aqueous mixed solution from becoming solidified by unintended heating during retention of the solution in the pipe L10 for a long period of time, the temperature in the pipe L10 is preferably controlled, and it may be controlled at approximately 50° C., for example. The retention time of the aqueous mixed solution in the pipe L10 is preferably from 3 seconds or more and 1 hour or less.

The filter 140 is disposed anterior to the dryer 120 along the supplying direction of the aqueous mixed solution. As shown in FIG. 1, in a case in which the pump 160 is provided between the mixed solution tank 110 and the dryer 120, the filter 140 is preferably positioned on the side more upstream of the above described supplying direction than the pump 160 from the viewpoint of suppression of clogging in the pump 160. However, in the case of using a pump that is hardly clogged, such as a uniaxial eccentric screw pump, the filter 140 may be positioned on the side either upstream or downstream (either aspiration side or discharge side) of the pump 160.

The type of the filter 140 is not particularly limited, as long as it is able to filtrate the aqueous mixed solution. As such a filter 140, a common filter such as a strainer or a sand filter may be used. As such a filter 140, a type Y, type T or type U strainer is preferable. Such a strainer supplies water in a direction opposite to the supplying direction of the aqueous mixed solution, and then filtrates the water through the filter 140, so as to perform backwashing of fouling attached to the net. Moreover, in terms of easiness of such backwashing, the filter 140 is particularly preferably a type Y strainer.

Figure 4:
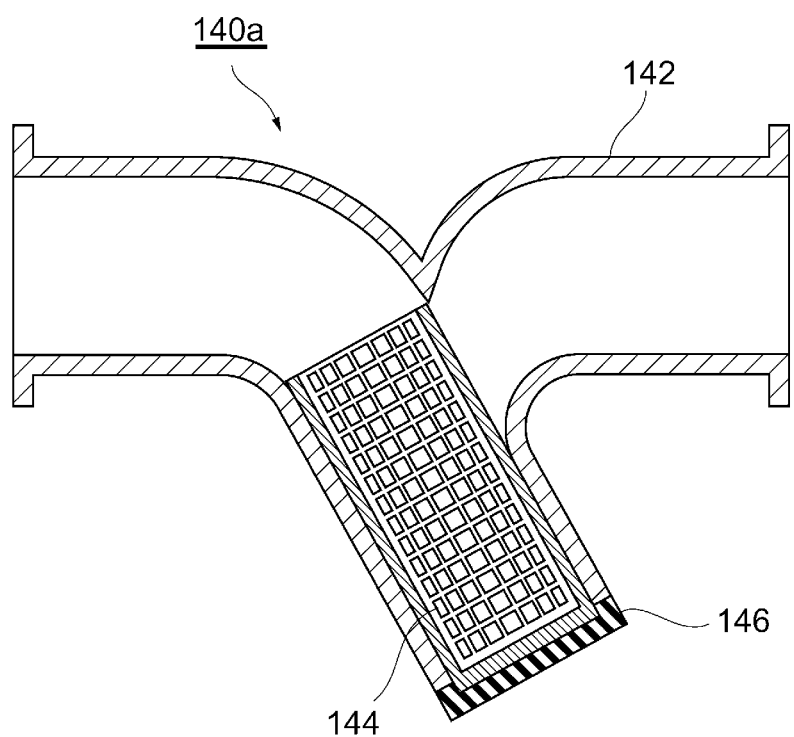
FIG. 4 is a schematic cross-sectional view showing an example of a type Y strainer 140 shown in FIG. 1.

As with the type Y strainer 140a shown in FIG. 4 for example, the type Y strainer comprises a strainer main body 142, a screen 144 contained therein, and a screen holder 146 that holds the screen 144 and is detachable to the strainer main body 142. The screen 144 has a cylindrical shape, for example, and it has an aperture in the upper portion thereof, into which the aqueous mixed solution flows, and also has a large number of pores (for example, a mesh net) on the lateral side thereof. When the aqueous mixed solution (or water) flowing into the type Y strainer 140a passes through the screen 144, solid fouling or gelatinous ingredients are captured by the screen 144. Then, the aqueous mixed solution (or water) is discharged to a site downstream of the type Y strainer 140a in a state in which such fouling or ingredients have been removed. The screen 144 that has captured the solid fouling or gelatinous ingredients, together with the screen holder 146, may be removed from the strainer main body 142, and may be then washed. Otherwise, the screen 144 that has captured the fouling or ingredients may also be washed by the above described backwashing, in a state in which it remains attached to the strainer main body 142.

The size of a pore (e.g. a mesh net) on the lateral side of the screen 144 is preferably 0.05 to 30.0 mm relative to the diameter of the pore. From the results of studies conducted by the present inventors, the size of such a pore is more preferably from 0.10 to 15.0 mm, which is a size range suitable for capturing fouling and the like. By setting the size of the pore in the aforementioned range, an increase in pressure attended with the capturing of fouling and the like is suppressed, and the subsequent drying treatment using a dryer can be carried out more favorably. In addition, by setting the size of the pore in the aforementioned range, fouling and the like can be captured more effectively.

The material for the screen 144 is not particularly limited. For example, stainless steel or carbon steel can be used. Of these, stainless steel is more preferable because it is hardly eroded.

The aqueous mixed solution that has passed through the above described filter 140 and pump 160 is dried in the dryer 120. The dryer 120 shown in FIG. 1 is a spray dryer. However, the type of the dryer is not limited thereto, and a conventionally known dryer may be used. For example, an evaporation drying machine may be used. The spray dryer is preferable because it can easily produce pseudospherical particles that are preferably used for fluidized bed reactions. The dryer (spray dryer) 120 shown in FIG. 1 comprises a dry chamber 124, a nozzle 122 for spraying the aqueous mixed solution into the dry chamber 124, and a dry product discharging port 126 for discharging a dry product of the aqueous mixed solution obtained by spray-drying.

The system for spraying the aqueous mixed solution in the dryer 120 is not particularly limited. For example, it may be a two-fluid nozzle system such as the nozzle 122 shown in FIG. 1. Otherwise, it may also be a centrifugal system, a high-pressure nozzle system, etc. The nozzle 122 shown in FIG. 1 injects spray gas (for example, air or nitrogen gas) together with the aqueous mixed solution, so that the spray gas contributes to microparticulation of the aqueous mixed solution. As a result, using such a nozzle 122, more fine particles of the dry product can be obtained. Moreover, the type of a dry heat source (not shown in the figure) is not particularly limited. For example, air heated by water vapor, an electrical heater or the like can be used. The temperature of the aqueous mixed solution at the inlet of the dryer 120 (hereinafter simply referred to as an "inlet temperature") is preferably from 150° C. to 300° C., the temperature in the dry product discharging portion 126 (hereinafter simply referred to as an "outlet temperature") is preferably from 100° C. to 160° C.

In general, as the aqueous mixed solution is converted to a dry product by heating in the drying operation in the dryer 120, the degree of oxidation-reduction thereof changes, and the performance of the obtained oxide catalyst is easily influenced thereby. When a dry product is industrially obtained by performing spray-drying on an aqueous raw material, there may be a case in which a portion of the dry product is attached to and accumulated on the wall surface and/or bottom portion of the dryer 120 and it remains in the device for a long period of time, and in which unintended heat is thereby given to the dry product. As a result, the degree of oxidation-reduction of the dry product may be changed, and it may influence on the performance of the finally obtained catalyst in some cases. Thus, for the purpose of preventing accumulation of the dry product in the dryer 120, a vibrator (not shown in the figure) for giving vibration to the dryer or an air knocker (not shown in the figure) for giving impact on the dryer is preferably equipped into the dryer 120, although the unit therefore is not limited.

The aqueous mixed solution sprayed from the nozzle 122 into the dry chamber 124 is dried therein, so that it is converted to a dry product. The dry product is then discharged from the dry product discharging port 126. The thus discharged dry product is supplied to a calcination device (not shown in the figure), and it is calcined therein, so as to obtain an oxide catalyst.

Constitutional elements of the oxide catalyst are not particularly limited. The oxide catalyst preferably comprises Mo (molybdenum), V (vanadium), Nb (niobium), and the aftermentioned elements represented by X, T and Z.

An example of the preferred oxide catalyst of the present embodiment is a catalyst having the composition represented by the following general formula (1):

$$MoV_aNb_bX_cT_dZ_eO_n \qquad (1)$$

Herein, a, b, c, d, e and n each represent the ratio of each atom to 1 atom of Mo. The atom ratios are within the ranges of $0.01 \leq a \leq 1$, $0.01 \leq b \leq 1$, $0.01 \leq c \leq 1$, $0 \leq d < 1$, and $0 \leq e < 1$, respectively; and n is a value satisfying the balance of valences.

It is preferable that, to 1 atom of Mo, the atom ratio a of V be from 0.1 or more to less than 0.4, and the atom ratio b of Nb be from 0.01 or more to less than 0.2. In addition, the atom ratio c of X ingredient to 1 atom of Mo is preferably from 0.01 or more to less than 0.6, and more preferably from 0.1 or more to less than 0.4.

Examples of the element represented by X include one or more elements selected from the group consisting of Sb (antimony), Te (tellurium), Sr (strontium), Ba (barium), Sc (scandium), Y (yttrium), La (lanthanum), Ce (cerium), Pr (praseodymium), Yb (ytterbium), W (tungsten), Cr (chromium), Ta (tantalum), Ti (titanium), Zr (zirconium), Hf (hafnium), Mn (manganese), Re (rhenium), Fe (iron), Ru (ruthenium), Co (cobalt), Rh (rhodium), Ni (nickel), Pd (palladium), Pt (platinum), Ag (silver), Zn (zinc), B (boron), Al (aluminum), Ga (gallium), In (indium), Ge (germanium), Sn (tin), Pb (lead), P (phosphorus), Bi (bismuth), other rare earth elements and alkaline earth elements. Examples of a compound containing these elements include nitrate, carboxylate, ammonium carboxylate salts, peroxocarboxylate, ammonium peroxocarboxylate salts, ammonium halide salts, halide, acetylacetonate, and alkoxide. Of these, aqueous raw materials typified by nitrate and carboxylate as typical examples are preferably used.

Preferred examples of the element represented by X include Te and Sb. In general, long-term durability at a temperature of 400° C. or higher is a property necessary for an industrial production method of an unsaturated nitrile, and Sb is particularly preferably used as the element represented by X. On the other hand, in an industrial production method of an unsaturated acid, a reaction can be carried out at a temperature of 400° C. or lower. Hence, influence by fugacity of Te during a long-term operation is limited, and thus, Te can also be preferably used.

The atom ratio d of the element represented by T to 1 atom of Mo is preferably from 0 or more to less than 1, more preferably from 0.001 or more to less than 0.1, and further preferably from 0.002 or more to less than 0.08. The elements represented by T are preferably one or more elements selected from the group consisting of Ti, Zr, Hf, Ta, Cr, W, Mn, Re, Fe, Co, Ni, Au, Zn, B, Al, Ga, In, Ge, Sn, Pb, P and Bi. Of these, Ti, W and Mn are more preferable.

The atom ratio e of the element represented by Z to 1 atom of Mo is preferably from 0 or more to less than 1, and more preferably from 0.0001 or more to less than 0.5. The elements represented by Z are preferably Sr, Ba, Sc, Y, La, Ce, Pr and Yb. Of these, Ce is particularly preferable. From the viewpoint of the improvement of the yield of a product of interest in an ammoxidation reaction, the oxide catalyst preferably contains the element represented by Z, and it is more preferable that such element Z be uniformly dispersed in catalyst particles. However, as Japanese Patent Application Laid-Open No. 11-244702 teaches, since there is a fear that the element represented by Z causes an unfavorable reaction in slurry, the content of the element represented by Z is preferably very small.

As a compound containing Mo (hereinafter referred to as a "Mo compound"; the same applies to other elements) serving as a raw material for Mo, ammonium molybdate oxide, ammonium heptamolybdate, phosphomolybdic acid, silicomolybdic acid can be used, for example. Of these, ammonium heptamolybdate [$(NH_4)_6Mo_7O_{24} \cdot 4H_2O$] can be preferably used.

Examples of a V compound serving as a raw material for V include vanadium pentoxide, ammonium metavanadate, and vanadyl sulfate. Of these, ammonium metavanadate [$NH_4VO_3$] can be preferably used.

Examples of a Nb compound serving as a raw material for Nb include niobic acid, inorganic acid salts of niobium, and organic acid salts of niobium. Of these, niobic acid can be preferably used.

When Te is added as the element represented by X, telluric acid [$H_6TeO_6$] can be preferably used as a raw material for Te. When Sb is added, antimony oxide, and particularly, antimony trioxide [$Sb_2O_3$] can be preferably used.

When the oxide catalyst is a silica-supported catalyst, silica sol, powder silica or the like can be added as a raw material for silica. As such powder silica, powder silica produced by a high heat method is preferable. By previously dispersing such powder silica in water and then using it, addition and mixing of the powder silica into slurry becomes easy. The dispersion method is not particularly limited. The powder silica can be dispersed in water by a single use of a common homogenizer, Homo Mixer, ultrasonic vibration machine, etc., or by a combined use thereof.

The method for producing the oxide catalyst of the present embodiment is not particularly limited. For example, the above described apparatus for producing a catalyst of the present embodiment may be used. An example of the production method includes the steps of: (a) mixing an aqueous raw material solution (I) containing a Mo compound and a V compound with an aqueous raw material solution (II) containing a Nb compound, and preferably a hydrogen peroxide solution, to obtain a preliminary mixed solution, and then aging the preliminary mixed solution preferably in an atmosphere of an oxygen concentration of 1 to 25 vol %, and preferably for 90 minutes to 50 hours, to obtain an aqueous mixed solution (III); (b) filtrating the aqueous mixed solution (III); (c) spray-drying the aqueous mixed solution (III) to obtain a dry product; and (d) calcining the dry product. Hereafter, each step will be described in detail.

(a) Step of Preparing Aqueous Mixed Solution

The step of preparing an aqueous mixed solution (hereinafter referred to as a "step (a)") is a step of mixing an aqueous raw material solution (I) containing a Mo compound and a V compound with an aqueous raw material solution (II) containing a Nb compound, and preferably a hydrogen peroxide solution, to obtain a preliminary mixed solution, and thereafter, aging the preliminary mixed solution to obtain an aqueous mixed solution (III).

In the present step (a), first, a Mo compound, a V compound, the after-mentioned X ingredient as necessary, and other ingredients serving as raw materials are added to an aqueous solvent such as water, a nitric acid aqueous solution, or an ammonia aqueous solution, and the obtained mixed solution is then stirred to prepare an aqueous raw material solution (I). The Mo compound, the V compound and the after-mentioned X ingredient added as necessary, which are powdery raw materials, are preferably measured using an automatic powder measuring machine (not shown in the figure) because this measurement can significantly reduce operation time. As such an automatic powder measuring machine, a conventionally known automatic powder measuring machine can be used. When the X ingredient is Sb that is a deleterious substance, such Sb is not substantially released in the air by the use of an automatic powder measuring machine having a hermetically closed structure, so that adverse effects given to human bodies can be reduced. The automatic powder measuring machine is connected with the mixed solution tank 110 by a pipe (not shown in the figure). As such a pipe, a small sanitary pipe or fluorocarbon resin pipe having a small surface friction is preferably used to prevent adhesion of powdery raw materials. In order to wash out powdery raw materials adhering to the pipe with gas or liquid, a washing device is preferably provided in the pipe. In addition, as a device removing powdery raw materials adhering to the pipe, a knocker and/or a vibrator are preferably provided in the pipe. The aqueous raw material solution (I) may be prepared in the mixed solution tank 110. The raw material ingredients are preferably heated upon preparation of the aqueous raw material solution (I). From the viewpoint of the solubility of the raw material ingredients, the heating temperature is preferably from 80° C. to 100° C., and the heating time is preferably 30 minutes or longer. From the viewpoint that the preparation time is set substantially identical to the spraying time, the preparation time is preferably within 3 hours. Moreover, during this operation, the aqueous raw material solution (I) may be prepared in an inert gas atmosphere, for example, in the mixed solution tank 110 that is in a nitrogen gas atmosphere.

In order to prevent the backflow of vapor generated from the aqueous raw material solution (I), or from an aqueous raw material solution (II) or an aqueous mixed solution (III), which will be described in detail later, to the side of the automatic powder measuring machine, a check valve is preferably provided in the pipe for connecting the mixed solution tank 110 with the automatic powder measuring machine. As such a check valve, a ball valve, a globe valve, a butterfly valve, a gate valve or the like can be used. In order to prevent adhesion of powdery raw materials, a ball valve having no impediments to the flow is preferably used. The check valve is closed, after powdery raw materials have been added from the automatic powder measuring machine to the mixed solution tank 110. Then, the check valve is opened, when powdery raw materials are added again after completion of the supply of an aqueous mixed solution (III) prepared in the mixed solution tank 110 to a dryer.

Subsequently, a Nb compound and preferably dicarboxylic acid are heated and stirred in water to prepare a mixed solution (B0). Thereafter, a hydrogen peroxide solution is preferably added to the mixed solution (B0) to prepare an aqueous raw material solution (II). In this operation, $H_2O_2$/Nb (molar ratio) in the aqueous raw material solution (II) is preferably 0.5 to 20, and more preferably 1 to 10. Thereafter, the aqueous raw material solution (I) is mixed with the aqueous raw material solution (II) at a preferred ratio, depending on the composition of interest, so as to obtain a preliminary mixed solution. When the aqueous raw material solution (I) has been prepared in the mixed solution tank 110, this mixing operation may be carried out by adding the aqueous raw material solution (II) into the mixed solution tank 110. Thereafter, the preliminary mixed solution is aged, for example, in the mixed solution tank 110, so as to prepare an aqueous mixed solution (III).

When antimony (Sb) is used as the ingredient X, hydrogen peroxide is preferably added into the aqueous raw material solution (I), or a raw material solution containing the aqueous raw material solution (I) that is in the midcourse of preparation. During this operation, $H_2O_2$/Sb (molar ratio) is preferably 0.01 to 5, more preferably 0.5 to 3, and further preferably 1 to 2.5. After addition of hydrogen peroxide, preferably, the obtained mixed solution is continuously stirred at 30° C. to 70° C. for 5 minutes to 4 hours. When spray-drying is continuously carried out, the preparation time of the aqueous mixed solution (III) is preferably set substantially identical to the spray-drying time, although this will be described later. Taking into consideration this point, the preparation time of the aqueous raw material solution (I), and the time in which hydrogen peroxide is added and then stirred in the case of using antimony (hereinafter referred to as a "processing time with hydrogen peroxide"), may be set within 2 hours, preferably within 1 hour, and more preferably within 30 minutes. When Sb is used, there may be a case in which, when raw materials are added to the mixed solution tank 110, the raw materials fall to the pipe L10 on the lower side of the mixed solution tank, without being mixed with a solution used for preparation. Thereby, since the composition of the finally obtained catalyst may be changed, a bottom valve is preferably provided in the connected portion of the mixed solution tank 110 with the pipe L10. As described above, from the viewpoint that the preparation time of the aqueous mixed solution (III) is set substantially identical to the spray-drying time, the preparation time of the aqueous raw material solution (I) and the processing time with hydrogen peroxide in the case of using Sb may be adjusted, as appropriate.

The term "aging" is used in the present step to mean that a preliminary mixed solution containing a Mo compound, a V compound and a Nb compound is left at rest or stirred in an oxygen atmosphere having a predetermined concentration for a predetermined period of time.

In the present step, from the viewpoint of prevention of excessive retardation of the progression of an oxidation-reduction reaction, which has a certain effect on the oxidation-reduction condition of metallic ingredients contained in the aqueous mixed solution (III), the oxygen concentration in the gas phase is preferably set at 1 vol % or more during the aging operation. On the other hand, from the viewpoint of prevention of excessive progression of the oxidation-reduction reaction, the oxygen concentration in the gas phase is preferably set at 25 vol % or less during the aging operation. Anyhow, since the oxygen in the gas phase has influence on the oxidation-reduction condition of the aqueous mixed solution (III), the oxygen concentration in the gas phase is preferably maintained in an appropriate range. The oxygen concentration in the gas phase during the aging operation is preferably 5 to 23 vol %, and more preferably 10 to 20 vol %.

The oxygen concentration in the gas phase during the aging operation can be measured by a general method, for example, using a zirconia-type oxygen concentration meter. The site at which the oxygen concentration in the gas phase is measured is preferably the proximity to the interface between the aqueous mixed solution (III) and the gas phase. For example, it is preferable that the oxygen concentration in the gas phase be measured 3 times within 1 minute at the same point, and that a mean value of the results of 3 measurements be defined as the oxygen concentration in the gas phase.

The type of a diluent gas for reducing the oxygen concentration in the gas phase is not particularly limited. Examples of such a diluent gas include gases such as nitrogen, helium, argon, carbon dioxide, and water vapor. The nitrogen gas is industrially preferable. Moreover, a gas used for increasing the oxygen concentration in the gas phase is preferably, for example, pure oxygen or air having a high oxygen concentration.

From the viewpoint of the improvement of the performance as an oxide catalyst of the obtained oxide, the aging time is preferably from 30 minutes to 6 hours. By setting the aging time within the aforementioned range, an aqueous mixed solution (III) having a preferable oxidation-reduction state (potential) is easily prepared, and the performance of the obtained oxide catalyst can be maintained higher. By adjusting the aqueous mixed solution (III) to be in a preferred oxidation-reduction state in the aforementioned time range, the yield of a product of interest obtained using the finally obtained catalyst is significantly increased. If the aging time exceeds 6 hours, the yield of such a product of interest obtained using the catalyst tends to decrease over time.

When the oxide catalyst is industrially produced via a spray-drying step, the processing speed of a spay dryer (for example, the dryer 120) is generally used as a rate-controlling factor. That is to say, there may be a case in which it takes a certain period of time until the spray-drying of all of the aqueous mixed solution (III) has been completed, after completion of the spray-drying of a portion of the aqueous mixed solution (III). During this period of time, the oxidation-reduction of the aqueous mixed solution (III), which has not yet been spray-dried, is continued. Accordingly, in order to appropriately determine the aging time, not only the time required until initiation of spray-drying, but also the time required until completion of the drying is taken into consideration, and the time required until completion of the drying is preferably set within 6 hours. When the preparation time of the aqueous mixed solution (III) is set substantially identical to the drying time, the drying time is preferably controlled within 6 hours in order to particularly improve the yield of a product of interest obtained using the catalyst. Thus, it is preferable that the preparation time of the aqueous mixed solution (III) be also controlled within 6 hours.

The aging temperature is preferably set at 25° C. or higher, from the viewpoint of prevention of the condensation of the Mo ingredient or the precipitation of the V ingredient. Moreover, the aging temperature is preferably set at 65° C. or lower from the viewpoint of preventing the complex containing Nb and hydrogen peroxide from being excessively hydrolyzed and forming the aqueous mixed solution (III) in a preferable form. Thus, the aging temperature is more preferably from 30° C. or higher to 60° C. or lower.

The preparation time of the aqueous mixed solution (III) essentially includes an aging time. When the preparation time required until the aging operation is shorter than the spray-drying time, the aging time is adjusted, so that the preparation time of the aqueous mixed solution (III) can be set substantially identical to the spray-drying time.

(Supply of Aqueous Mixed Solution (III))

In order to produce a catalyst having excellent performance at a high recovery rate over a long period of time without significantly increasing the temperature in the spray dryer during the production of the catalyst, the aqueous mixed solution (III) is preferably continuously supplied to the spray dryer. In order to continuously supply an aqueous mixed solution (III) to the spray dryer, the apparatus for producing a catalyst preferably comprises a plurality of mixed solution tanks with respect to a single spray dryer. Thereby, while an aqueous mixed solution (III) is supplied from one or more mixed solution tanks out of the plurality of mixed solution tanks to the spray dryer and is then spray-dried therein, another aqueous mixed solution (III) can be prepared in other one or more mixed solution tanks that are different from the above described one or more mixed solution tanks. Alternatively, after an aqueous mixed solution (III) has previously been prepared in two or more mixed solution tanks, the aqueous mixed solution (III) may be supplied from certain one or more mixed solution tanks to the spray dryer, and it may be then spray-dried therein. As a result, before the spray-drying of an aqueous mixed solution (III) supplied from one or more mixed solution tanks has been completed, another aqueous mixed solution (III) to be next supplied to the spray drier is stored in the other one or more mixed solution tanks. Thereafter, by successively supplying the aqueous mixed solution (III) prepared in the other one or more mixed solution tanks to the spray dryer, it becomes possible that the aqueous mixed solution (III) be continuously spray-dried in the spray dryer.

The apparatus for producing a catalyst of the present embodiment, which can continuously supply the aqueous mixed solution (III) to the spray dryer as described above, comprises a plurality of mixed solution tanks. The present apparatus for producing a catalyst is configured to spray-dry an aqueous mixed solution (III) prepared in one or more mixed solution tanks by a spray dryer, and then to spray-dry another aqueous mixed solution (III) prepared in other one or more mixed solution tanks that are different from the above described mixed solution tanks by the spray dryer. Specifically, the apparatus for producing a catalyst comprises a plurality of mixed solution tanks, and a spray dryer with which the plurality of mixed solution tanks are connected. According to this production apparatus, after an aqueous mixed solution (III) supplied from one or more mixed solution tanks to a spray dryer has been sprayed from the spray dryer, another aqueous mixed solution (III) is supplied from other one or more mixed solution tanks that are different from the above described mixed solution tanks to the spray dryer. Then, this aqueous mixed solution (III) is sprayed from the spray dryer, following the above described aqueous mixed solution (III), so that continuous spray-drying can be carried out.

For example, when the apparatus for producing a catalyst comprises two mixed solution tanks (the first mixed solution tank and the second mixed solution tank), after an aqueous mixed solution (III) supplied from the first mixed solution tank to a spray dryer has been spray-dried by the spray dryer, another aqueous mixed solution (III) is supplied from the second mixed solution tank to the spray dryer, and it is then spray-dried.

In the production apparatus of the present embodiment, preferably, a plurality of mixed solution tanks are directly or indirectly connected with the spray dryer via pipes. The number of such mixed solution tanks connected with a single spray dryer is not limited. If the number of such mixed solution tanks increases, a broad site area is required for accommodating the mixed solution tanks, the cost of equipment increases, the switching of mixed solution tanks becomes complicated, and a great care becomes necessary for the operation. In order to suppress the aforementioned phenomena, the number of mixed solution tanks is preferably approximately 2 to 4. It is more preferably 2, which is the smallest number of mixed solution tanks enabling continuous spray-drying.

Figure 5:
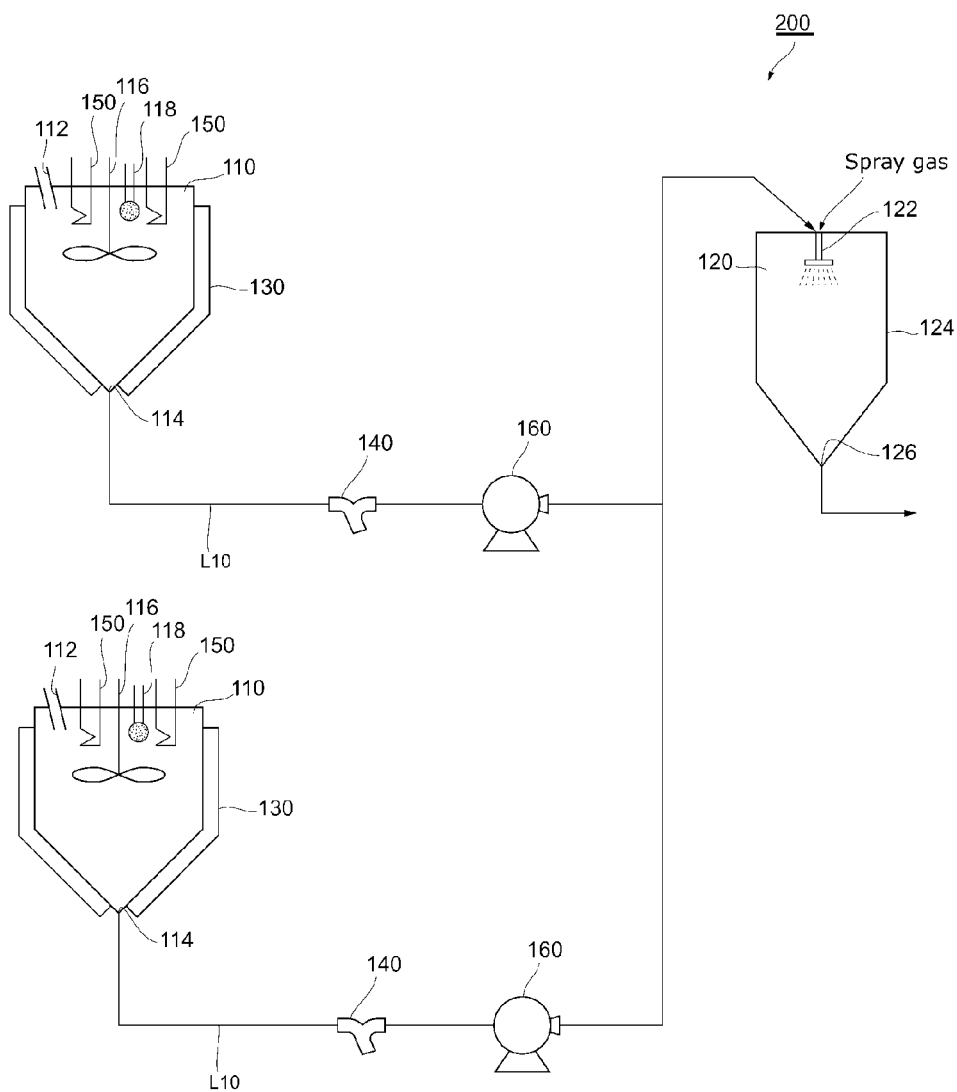
FIG. 5 shows an embodiment of a plurality of mixed solution tanks and a spray dryer for carrying out the method for producing a catalyst of the present embodiment.

FIG. 5 is a schematic view partially showing another example of the apparatus for producing a catalyst of the present embodiment. This production apparatus 200 has the same configuration as that of the production apparatus 100 shown in FIG. 1, with the exceptions that it comprises two mixed solution tanks 110, two stirrers 116 attended therewith, two washing devices 118, two filters 140, and two pumps 160, and that two pipes L10 are joined on the discharge side of the pumps 160. In this production apparatus 200, in order to supply an aqueous mixed solution (III) from one mixed solution tank 110 to a dryer 120 and/or the other mixed solution tank 110, the pumps 160 are each provided in the midcourse of the pipes L10. Herein, the pipe L10 is a device that connects one mixed solution tank 110 with the dryer 120 and/or the other mixed solution tank 110, so as to supply the aqueous mixed solution (III) or water. Such a pipe L10 enables the transfer of the aqueous mixed solution (III) or water between the two mixed solution tanks 110. Moreover, for the purpose of preventing the clogging of the pipe due to accumulation of fouling, two or more systems of the pipes for connecting one mixed solution tank 110 with the dryer 120 and/or the other mixed solution tank 110 are preferably provided, although they are not shown in the figure.

Thus, a method for producing a catalyst using a production apparatus comprising a plurality of mixed solution tanks comprises a step of continuously spray-drying an aqueous mixed solution, in which after an aqueous mixed solution (III) has been spray-dried from one or more mixed solution tanks, another aqueous mixed solution (III) prepared in other one or more mixed solution tanks that are different from the above described one or more mixed solution tanks is supplied to the spray dryer and is then spray-dried therein. In this case, as described above, if an aqueous mixed solution (III) is prepared in other one or more mixed solution tanks while another aqueous mixed solution (III) is spray-dried from the other one or more mixed solution tanks, the preparation and spray-drying of the aqueous mixed solution can be carried out efficiently. Thus, it is preferable.

For example, a method for producing a catalyst using the above described production apparatus 200 includes the step of continuously spray-drying the aqueous mixed solution in the dryer 120, in which after an aqueous mixed solution (III) supplied from one mixed solution tank 110 to the dryer 120 has been spray-dried by the dryer 120, another aqueous mixed solution (III) prepared in the other mixed solution tank 110 is supplied to the dryer 120 and is then spray-dried therein.

In the production method of the present embodiment, a mixed solution tank for preparing an aqueous mixed solution (III) may be identical to or different from a mixed solution tank for supplying the aqueous mixed solution (III) to the spray dryer.

When the mixed solution tank for preparing an aqueous mixed solution (III) is identical to the mixed solution tank for supplying the aqueous mixed solution (III) to the spray dryer, the production method of the present embodiment includes an embodiment in which, while an aqueous mixed solution (III) is prepared in one or more mixed solution tanks and the obtained aqueous mixed solution (III) is spray-dried, another aqueous mixed solution (III) is further prepared in other one or more mixed solution tanks that are different from the above described mixed solution tanks, and after completion of the above described spray-drying, the aqueous mixed solution (III) prepared in the other one or more mixed solution tanks is supplied to the above described spray dryer and is then spray-dried.

In addition, when the plurality of mixed solution tanks are two mixed solution tanks, the above described plurality of mixed solution tanks consist of the first mixed solution tank and the second mixed solution tank, and the production method of the present embodiment includes an embodiment in which, while an aqueous mixed solution (III) is spray-dried from the first mixed solution tank, another aqueous mixed solution (III) is further prepared in the second mixed solution tank, and after completion of the above described spray-drying, the aqueous mixed solution (III) prepared in the second mixed solution tank is supplied to the spray dryer and is then spray-dried.

In the production method of the present embodiment, while an aqueous mixed solution (III) is prepared in one or more mixed solution tanks, another aqueous mixed solution (III) may be supplied from other one or more mixed solution tanks that are different from the above described mixed solution tanks to the spray dryer, and it may be then spray-dried. In this operation, (1) each mixed solution tank may be connected with the spray dryer via a pipe. In this case, an aqueous mixed solution (III) may be prepared in each mixed solution tank, and the supply of the prepared aqueous mixed solution may be suspended, as necessary, until the supply of another aqueous mixed solution (III) from another mixed solution tank has been completed. Thereafter, the prepared aqueous mixed solution (III) may be supplied from the different mixed solution tank to the spray dryer. Alternatively, (2) a mixed solution tank may comprise a dedicated preparation tank and a dedicated storage tank, and the dedicated preparation tank may be connected with the dedicated storage tank directly or via a pipe, and the dedicated storage tank may be connected with the spray dryer via a pipe. In this case, an aqueous mixed solution prepared in the dedicated preparation tank may be transferred to the dedicated storage tank, and the supply of the prepared aqueous mixed solution (III) may be suspended, as necessary, until the supply of another aqueous mixed solution (III) from another dedicated storage tank has been completed. Thereafter, the prepared aqueous mixed solution (III) may be supplied from the different dedicated storage tank to the spray dryer.

Figure 6:
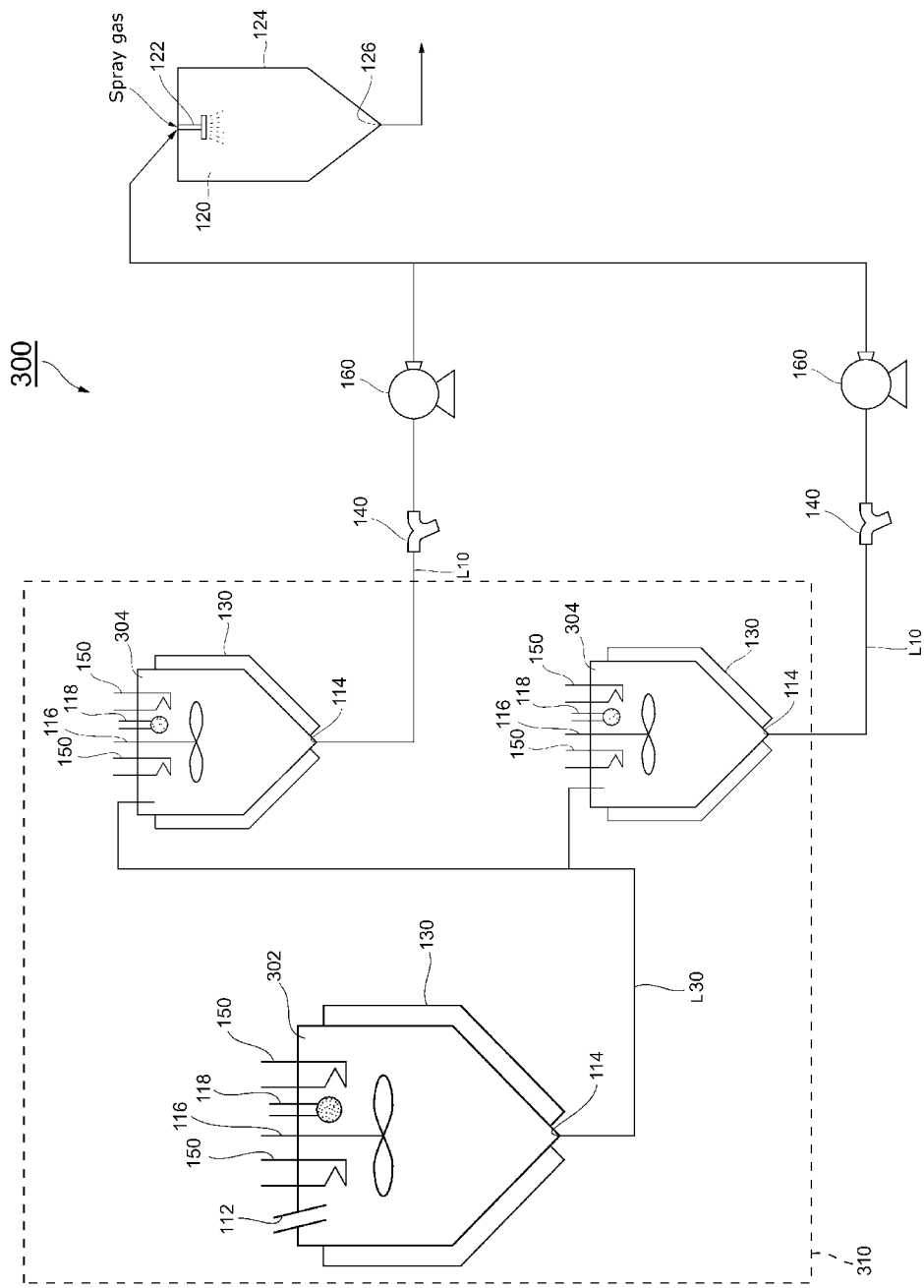
FIG. 6 shows another embodiment of a plurality of mixed solution tanks and a spray dryer for carrying out the method for producing a catalyst of the present embodiment.

Moreover, the embodiment described in (1) above may be combined with the embodiment described in (2) above. FIG. 5, which has been described above, shows an example of the embodiment described in (1) above, whereas FIG. 6 shows an example of the embodiment described in (2) above. FIG. 6 is a schematic view partially showing a further example of the apparatus for producing a catalyst of the present embodiment. This production apparatus 300 has the same configuration as that of the production apparatus 200 shown in FIG. 5, with the exception that it comprises, instead of the aforementioned two mixed solution tanks 110, a large dedicated preparation tank 302, two dedicated storage tanks 304 that are smaller than the dedicated preparation tank 302, and pipes L30 for connecting them. As the dedicated preparation tank 302, a tank similar to the mixed solution tank 110 shown in FIG. 5 can be used. That is, temperature control devices 130 and 150 are provided in the dedicated preparation tank 302, and the tank comprises a raw material supplying port 112, an aqueous mixed solution discharging port 114, and further, a stirrer 116 and a washing device 118. As the dedicated storage tank 304, a tank similar to the mixed solution tank 110 shown in FIG. 5 can be used, with the exceptions that it is smaller than the dedicated preparation tank 302 and that it has a nozzle for introducing an aqueous mixed solution (III) from the dedicated preparation tank 302, instead of the raw material supplying port 112. That is, temperature control devices 130 and 150 are provided in dedicated storage tank 304, and the tank comprises an aqueous mixed solution discharging port 114, a stirrer 116 and a washing device 118.

In all of the embodiments, it is important that, immediately after the supply of an aqueous mixed solution (III) from the previous mixed solution tank or dedicated storage tank to a spray dryer has been completed, another aqueous mixed solution (III) is supplied to the spray dryer from the next mixed solution tank or dedicated storage tank, so that spray-drying is continuously carried out. Accordingly, from the viewpoint of efficient production of a catalyst and also from the viewpoint of the improvement of the yield of a product of interest obtained using the catalyst, the preparation time of the aqueous mixed solution (III) is preferably set substantially identical to the spray-drying time. In particular, in the case of the embodiment (1) in which an aqueous mixed solution is directly supplied from each mixed solution tank to a spray dryer, a large effect of facilitating the continuous supply of the aqueous mixed solution (III) to the spray dryer can be obtained by adjusting the preparation time of the aqueous mixed solution (III) to become identical to the spray-drying time.

Herein, the expression "substantially identical" means that a time difference that does not substantially fluctuate the temperature in a spray drier is included in the time range. It is preferably within 30 minutes, more preferably within 15 minutes, and further preferably within 5 minutes.

On the other hand, in the case of the embodiment (2) in which a mixed solution tank comprises a dedicated preparation tank and a dedicated storage tank, and an aqueous mixed solution (III) is supplied from the dedicated storage tank to a spray dryer, a large mixed solution tank provided as a dedicated preparation tank and a plurality of mixed solution tanks provided as dedicated storage tanks that are smaller than the dedicated preparation tank are considered to be a preferred combination. In the case of the above described combination, it is not that an aqueous mixed solution (III) is prepared in a large mixed solution tank, and that the aqueous mixed solution (III) is supplied from the large mixed solution tank to a spray dryer and then it is directly spray-dried. In this combination, an aqueous mixed solution (III) is once distributed (supplied) from the large mixed solution tank to a plurality of small mixed solution tanks, and thereafter, the aqueous mixed solution (III) is successively supplied from the small mixed solution tanks to the spray dryer, and it is then spray-dried. The large mixed solution tank, which had completed distribution of the solution to the small mixed solution tanks, can prepare an aqueous mixed solution (III) to be used in the next batch, until all of the aqueous mixed solution (III) contained in each small mixed solution tank has been supplied to the spray dryer and has been then spray-dried, and then, it can supply it at least to the small mixed solution tanks. Thereby, continuous spray-drying can be carried out. In this case, it is preferable that a total of the preparation time of the aqueous mixed solution (III) in the large mixed solution tank and the time for distributing the prepared solution to the small mixed solution tanks be substantially identical to the spray-drying time, as stated above. The embodiment in which such a dedicated preparation tank and dedicated storage tanks are used is only an example, and the present invention includes various cases of using a plurality of mixed solution tanks. From the viewpoint that a plurality of mixed solution tanks are provided and the aqueous mixed solution (III) is continuously spray-dried, if the size of a mixed solution tank, the preparation time of the aqueous mixed solution (III) and the spray-drying time are adjusted, they are all included in the scope of the present invention.

Next, adjustment of the preparation time of the aqueous mixed solution (III) and the suspending time until the supply of the aqueous mixed solution (III) to the spray dryer will be described. As described above, from the viewpoint of catalytic performance, the aqueous mixed solution (III) is preferably aged. In order to adjust the lengths of the preparation time of the aqueous mixed solution (III) and the spray-drying time, the preparation time of the aqueous mixed solution (III) can be controlled by increasing or decreasing this aging time. When the preparation time is changed by the increase or decrease of the aging time, in an embodiment in which aging has influence on catalytic performance, from the viewpoint of keeping the catalytic performance, the lower and upper limits of the aging time have previously been examined, and the aging time is preferably determined within the ranges of the lower and upper limits. As a result of intensive studies conducted by the present inventors, a preferred lower limit of the aging time is 30 minutes, and a preferred upper limit thereof is 6 hours.

There may be a case in which the preparation time of the aqueous mixed solution (III) becomes longer than the spray-drying time due to various factors such as a fluctuation in the amount of heating/cooling fluids (heating medium/cooling medium) in the temperature control device, a deviation in the measurement of raw materials for the oxide catalyst, and the breakdown of a producing apparatus during the preparation of the aqueous mixed solution (III). In such a case, it is preferable that water or a diluted aqueous mixed solution (III) be supplied to the spray dryer, and that the temperature fluctuation in the spray dryer be reduced to the minimum without interrupting the spray-drying operation.

In contrast, there may also be a case in which the preparation time of the aqueous mixed solution (III) becomes shorter than the spray-drying time due to various reasons such as a fluctuation in the amount of heating/cooling fluids (heating medium/cooling medium), the clogging of a pump (for example, the pump 160) for supplying the aqueous mixed solution (III) to the spray dryer, a fluctuation in the supply amount due to deterioration over time, and the breakdown of the spray dryer. In such a case, the aging time of the prepared aqueous mixed solution (III) can be extended up to the time at which the spray-drying operation is completed. However, since the degree of oxidation-reduction of the aqueous mixed solution (III) changes every minute during the aging operation, the degree of oxidation-reduction of a dry product obtained while the aging time is extended is significantly different from that of a dry product obtained after an ordinary aging time. As a result, an oxide catalyst causing a low yield of a product of interest may be obtained. For such a reason, the extended amount of the aging time is preferably set within 40 hours, and preferably within 2 hours.

Preparation of the aqueous mixed solution (III), spray-drying, switching from preparation to spray-drying, and switching from spray-drying to preparation can be carried out manually. However, in industrial mass production, automatic operation is preferably carried out by sequence control.

Moreover, in industrial mass production, fouling is found in the mixed solution tank, in the pipe, and in the spray dryer (for example, on the distributor in the nozzle). Thus, the preparation time of the aqueous mixed solution (III) preferably includes the time required for washing the inside of the mixed solution tank, which is carried out after all of the prepared aqueous mixed solution (III) has been discharged from the mixed solution tank, as well as the time required for preparing the aqueous mixed solution (III).

Fouling found in the pipe, in the filter, and in the members of the spray dryer such as a distributor is preferably washed on a regular basis. As washing frequency, such washing is carried out once two weeks, preferably once a week, and more preferably once two days, because it is able to reduce accumulation of fouling.

In the step (a), the procedures of dissolving, mixing and dispersing raw materials for the above described elements that constitute the catalyst (hereinafter referred to as "catalyst-constituting elements") are not particularly limited. The raw materials may be dissolved, mixed or dispersed in a single aqueous medium. Otherwise, each raw material may be dissolved, mixed or dispersed in a different aqueous medium, and such aqueous media may be then mixed with one another. In addition, such raw materials may be heated and/or stirred, as necessary. Examples of such an aqueous medium include water and water-soluble organic solvents such as a nitric acid aqueous solution, an ammonia aqueous solution or ethanol.

(b) Filtration Step

The filtration step (hereinafter referred to as a "step (b)") is a step of filtrating the aqueous mixed solution (III) obtained via the above-mentioned step (a). By this step (b), solid fouling or gelatinous ingredients can be removed from the aqueous mixed solution (III). An example of the filtration method is a method of allowing the aqueous mixed solution (III) to pass through the above described filter.

(c) Drying Step

The drying step (hereinafter referred to as a "step (c)") is a step of drying the aqueous mixed solution (III) obtained via the above-mentioned step (b), so as to obtain a dry product.

Examples of a drying unit include spray-drying and evaporation drying. From the viewpoint of production of pseudo-spherical particles that are preferably used for fluidized bed reactions, it is preferable to adopt spray-drying in industrial production. By such spray-drying, a catalyst precursor (dry product) that is a microspherical particle can be obtained.

The type of atomization in the spray-drying method is not particularly limited. For example, atomization in the spray-drying method may be performed using a centrifugation system, a two-fluid nozzle system, a high-pressure nozzle system, or the like. As a heat source, air heated by a steam, an electrical heater, or the like can be used. With regard to the temperature in the spray-drying, the inlet temperature of a dryer is preferably from 150° C. to 300° C., and the outlet temperature thereof is preferably from 100° C. to 160° C. Moreover, during the spray-drying, for the purpose of preventing accumulation of dry products in the spray dryer, it is preferable that vibration or impact be given to the spray dryer.

Herein, the degree of oxidation-reduction of the oxide catalyst is generally changed by heating during the drying operation, and the performance of the obtained oxide catalyst is affected thereby. When a dry product is obtained from the aqueous mixed solution (III) by industrially performing spray-drying, there may be a case in which a portion of the dry product is attached to and accumulated on the wall surface and/or bottom portion of the device and it remains in the device for a long period of time. Thereby, unintended heat may be given to the dry product, the degree of oxidation-reduction of the dry product may be changed, and catalytic performance may be deteriorated. Accordingly, for the purpose of preventing accumulation of the dry product in the spray dryer, vibration is preferably given to the spray dryer. As a unit for giving such vibration, it is preferable that a vibrator or an air knocker for giving impact be equipped into the spray dryer.

The aforementioned unintended heat may be caused by interruption of the spray-drying. The present inventors have industrially prepared an aqueous mixed solution (III). Thereafter, they have performed spray-drying on the aqueous mixed solution (III) and have then calcined the resultant, so as to prepare a catalyst. As a result, it was found that, although such catalysts could be produced without problems in one to several batches, then, catalysts with low performance may be produced in many cases during continuous production of the catalysts. When practically useless catalysts were sifted from the thus produced catalysts, the yield was significantly decreased. As a result of intensive studies regarding the factor therefore, it was found that there is a time at which the spray dryer takes a pause due to the relationship among the time required for preparation of the aqueous mixed solution (III), the retention time of the aqueous mixed solution (III) that is capable of maintaining the yield of a product of interest obtained using the finally obtained catalyst, and the capacity of the spray dryer, and that the condition of the spray dryer changes during such a pause.

That is to say, the temperature in the spray dryer is decreased by evaporation of water content in the sprayed aqueous mixed solution (III). Thus, if the aqueous mixed solution (III) is not supplied and spray-drying is thereby interrupted, the temperature in the dryer is significantly increased. Although the temperature tends to be decreased if the spray-drying is started again, the high-temperature condition is continued until it reaches a stable temperature. If the aqueous mixed solution (III) is spray-dried in such a high-temperature condition, drying excessively progresses, and as a result, the performance of the obtained catalyst is decreased. As with the method described in Japanese Patent Application Laid-Open No. 2011-005364, if uneven drying of the dry product obtained in the drying step is monitored as a degree of oxidation-reduction, production of defective catalysts can be certainly prevented. However, it does not mean that generation of a dry product having an inappropriate oxidation degree due to repetition of an operation and a rest can also be prevented.

During the spray-drying operation, the temperature is maintained by the balance between heating by the spray dryer and evaporation of the water content in the aqueous mixed solution (III) dried in the dryer. However, if such a spray-drying is interrupted, the temperature in the dryer is increased by interruption of the evaporation of the water content by the spray-drying operation. In a case in which the spray-drying of the aqueous mixed solution (III) is started again after the temperature in the spray dryer has been increased, since a high-temperature condition is continued until the temperature has reached a desired drying temperature, it results in excessive heat given to a dry product. In this case, as in the case of retaining a dry product in a dryer, there is a fear that the degree of oxidation-reduction of the dry product may be changed, and that catalytic performance may be deteriorated. Particularly in the case of large-scale facilities used in industrial production, it takes a long period of time from restart of the spray-drying to the achievement of a desired drying temperature. As a result, the influence by interruption of the spray-drying is more dominant than the influence by long-term retention in the dryer.

In order to suppress the quality loss of a dry product due to interruption of the spray-drying, the present inventors have conceived of continuously performing the spray-drying so as not to substantially interrupt the spray-drying. However, the spray-drying is "continuously" performed, so as to prevent the phenomenon whereby the temperature in the device becomes excessively high due to the "interruption" as described above and it affects the properties of a dry product. Accordingly, a short-term rest that does not substantially change the temperature in the spray dryer is not included in the interruption of the spray-drying of the present embodiment. For instance, the removal and washing of a distributor or the cleaning of a pipe takes only about 10 minutes out of several days. Such a short-term rest causes only a small decrease in the temperature in the dryer, and thus, even if dry products with low quality were produced, the ratio thereof would be limited. Accordingly, such a short-term rest is not included in the interruption of the spray-drying of the present embodiment. Moreover, when an aqueous mixed solution (III) to be supplied to the spray dryer is switched from an aqueous mixed solution (III) prepared or stored in a certain mixed solution tank to another aqueous mixed solution (III) prepared or stored in another mixed solution tank different from the certain mixed solution tank, there may be generated a time at which the spray-drying is interrupted. However, in this case as well, for the same reason as described above, such a time is not included in the interruption of the spray-drying of the present embodiment. From the above described viewpoint, the time at which the spray-drying is interrupted is preferably within 30 minutes, more preferably within 15 minutes, and further preferably within 5 minutes.

In order to predict the performance of an oxide catalyst obtained by calcining the dry product obtained by the step (c) before subjecting it to the after-mentioned calcination step, a part of the dry product obtained by the step (c) can be recovered, and its absorption or reflection spectrum can be measured. When small quantities of dry products having significantly poor catalytic performance are mixed in dry products having good catalytic performance, it is difficult to monitor them based on the absorption or reflection spectra thereof. However, by measuring the absorption or reflection spectra of the obtained dry products continuously at high frequency, the performance of the finally obtained oxide catalyst can be predicted based on the absorption or reflection spectra.

The degree of oxidation-reduction of the oxide catalyst is changed by heating during the drying step, and the performance of the obtained oxide catalyst is affected thereby. When a dry product is obtained by spray-drying the aqueous mixed solution (III) in the above described drying step, a portion of the dry product is attached to and accumulated on the wall surface and/or bottom portion of the dryer, and it remains in the dryer for a long period of time. Thereby, unintended heat is given to the dry product, and the degree of oxidation-reduction of the dry product changes. In the after-mentioned calcination step, when a catalyst is calcined in the air atmosphere, it is based on the premise that the oxidation of the catalyst progresses in the calcination step. Thus, the degree of oxidation-reduction of a dry product hardly affects the performance of a catalyst as a final product. On the other hand, when a catalyst is calcined in the inert gas atmosphere in the calcination step, the degree of oxidation-reduction of a dry product easily affects the performance of an oxide catalyst. In particular, when the preparation method is optimized while taking into consideration the degree of oxidation-reduction of an oxide catalyst, if the degree of oxidation-reduction of a dry product is deviated from a desired range, the catalytic performance naturally tends to be deteriorated. A detailed mechanism is unknown, but the color of the dry product changes as the degree of oxidation-reduction thereof changes. Taking a catalyst containing Mo, V and Nb for example, as the color of a dry product particularly becomes black, the performance of the oxide catalyst thereof tends to be deteriorated. As a reason therefore, it is considered that organic ingredients or inorganic ingredients contained in the dry product are thermally decomposed by unintended heating, and that metallic elements around them are reduced or an oxidation-reduction reaction of metallic elements takes place.

If a dry product with poor catalytic performance were obtained, the cause thereof would be the presence of many dry products that remain for a long period of time in the dryer (spray dryer) or in the pipe. In such a case, it is preferable to once terminate the preparation step and the drying step and to forcibly discharge the dry product remaining in the dryer or in the pipe. As such a unit for forcibly discharging the dry product, it is more preferably to remove it by jet cleaning.

The method for measuring the absorption or reflection spectrum is not particularly limited. For example, the absorption or reflection spectrum is determined based on the absorbance of the dry product measured using a UV-visible spectrophotometer. A dry product more discolored black has larger absorbance at a wavelength of 500 nm or more, than that of a dry product that is less discolored black. Thus, absorbance at any given wavelength in a wavelength range of 500 nm or more, and preferably of 500 nm or more and 800 nm or less, can be selected and used as an index in the measurement. The correlation between the absorption spectrum and the catalytic performance can be obtained with reference to Japanese Patent Application Laid-Open No. 2011-005364, for example.

It is preferable that the absorption or reflection spectrum of the dry product be measured continuously. In this context, the expression "measured continuously" means that the measurement is performed once or more frequently in 3 months. The spectrum is measured more preferably once a month, further preferably once a week, and particularly preferably once or more frequently per day. The more frequently the measurement is performed, the more greatly the risk of forming large quantities of dry products having the inappropriate degree of oxidation-reduction can be reduced.

The dry product obtained via the step (c) can be prepared such that the content of particles having a particle size of 25 μm or smaller is preferably 20% by mass or less, more preferably 15% by mass or less, further preferably 10% by mass or less, particularly preferably 5% by mass or less, and extremely preferably 2% by mass or less. By virtue of the 20% by mass or less content of particles having a particle size of 25 μm or smaller, there is a tendency in the resulting catalyst to achieve prevention of reduction in its performance, and prevention of reduction in the yield of the product of interest in an apparatus used for fluidized-bed reactions.

The reason why oxide catalyst performance is deteriorated is not clear. Presumably, this may be because if the content of particles having a particle size of 25 μm or smaller exceeds 20% by mass, uneven calcination tends to occur in the after-mentioned calcining device (calcination tube) due to the reduced fluidity of the catalyst. According to more detailed discussion, dry product particles having a small particle size return into the calcining device, particularly in continuous calcination, and are thus exposed to the calcination atmosphere for a longer time than the desired one. Therefore, there might arise problems such as the inappropriate rate of reduction of pre-stage calcined products in pre-stage calcination described later, and the decomposition of crystals attributed to excessive calcination in main calcination. Furthermore, if the content of dry product particles having a particle size of 25 µm or smaller exceeds 20% by mass in the dry product, the resulting pre-stage calcined product particles tend to adhere to something. Therefore, the performance is deteriorated, presumably because the particles adhering to the wall of the calcining device accumulate thereon, incurring the risk of insufficient heat transfer into the inside thereof or contamination with catalysts derived from particles excessively calcined due to the long-lasting adherence. In this context, the "pre-stage calcined product" refers to a compound formed in the course of the calcination step described later. For example, a compound obtained by pre-stage calcination is referred to as the pre-stage calcined product. For these reasons, an oxide catalyst having performance (e.g., the yield of the product of interest) equivalent to that obtained in batch calcination can be produced stably in catalyst production by continuous calcination using a dry product prepared to have a 20% by mass or less content of particles having a particle size of 25 µm or smaller, even when catalyst composition is the same between the methods.

When the oxide catalyst contains Mo, Sb, and Te, and the like, a low-melting-point compound tends to be formed during calcination. Particles having a particle size of 25 µm or smaller have a larger specific surface area ratio to particle area than that of particles having a particle size exceeding 25 µm and therefore seem to tend to adhere to something more easily. If too many particles are adhered, there arise problems, for example, a sufficient calcination temperature cannot be obtained for the catalyst layer, and sufficient yields cannot be secured. Accordingly, it is preferred to create a state in which particles having a particle size of 25 µm or smaller are few in number, i.e., to adjust the content of such particles to 20% by mass or less, at a stage prior to calcination.

The dry product particle is preferably prepared such that its average particle size is preferably 35 to 75 µm, more preferably 40 to 65 µm, and further preferably 45 to 60 µm. When the oxide catalyst is used in a fluid-bed catalytic reaction, if the average particle size of a dry product particle is 35 µm or greater, there is a tendency in the resulting catalyst to achieve prevention of reduction in fluidity resulting in the reduced yield of the fluidized-bed reaction product of interest, or prevention of a great loss of the amount of the catalyst caused by flying out of a fluidized-bed reactor. If the average particle size is 75 µm or smaller, there is a tendency in the resulting catalyst to achieve prevention of reduction in oxide catalyst fluidity and in contact efficiency with reaction gas resulting in the reduced yield of the fluidized-bed reaction product of interest.

The rate of reduction of the pre-stage calcined product can be adjusted to a preferable range in the calcination step described later by adjusting the average particle size of the dry product particles to preferably 35 to 70 µm and the content of particles having a particle size of 25 µm or smaller to preferably 20% by mass or less. This mechanism is interpreted by the present inventors as follows, though it is not limited thereto.

The dry product usually contains at least one of ammonium ion, an organic acid, and an inorganic acid. When the dry product is calcined with an inert gas circulated, the catalyst-constituting elements are reduced during the evaporation, decomposition, or the like of the ammonium ion, the organic acid, and/or the inorganic acid. The ammonium ion evaporates to form an ammonia gas, which reduces pre-stage calcined product particles from the gas phase. The rate of reduction of the pre-stage calcined product varies depending on the calcination time and the calcination temperature, particularly in pre-stage calcination described later. A long calcination time or a high calcination temperature facilitates reduction, leading to the high rate of reduction. When a large number of dry products having a relatively small particle size (catalyst precursors; hereinafter, also referred to as "small particles") are contained, typically when the average particle size is smaller than 35 µm or the content of particles having a particle size of 25 µm or smaller exceeds 20% by mass, the dry product particles are entrained in an inert gas or scattered along with the rotation of a calcination tube. As a result, many particles return into the calcination tube and may thus reside in the calcination tube for a time longer than the desired one, making it difficult to obtain the preferred range of the rate of reduction. Moreover, the small particles also seem to tend to be reduced, because many sites in the surface come in contact with an ammonia gas. On the contrary, if the average particle size of the dry product particles exceeds 75 µm, its particles are large and thus have a few sites in the surface that come in contact with an ammonia gas. Thus, such a dry product is hard to be reduced. As a result, the rate of reduction may become difficult to adjust to the preferred range.

In this context, the content of particles having a particle size of 25 µm, or smaller is a value that is determined by calcining a portion of the dry product particles at 400° C. for 1 hour in the air, sieving 20 g of the obtained particles using a sieve size of 25 µm and a diameter of 20 cm upon exposure to a vibrator (e.g., Panabrator (trade name) manufactured by National) for 3 minutes, and measuring the mass of particles passing through the sieve and the mass of particles remaining on the sieve, followed by calculation using the following formula:

(Content (%) of particles with particle size of 25 µm or smaller)=(Mass of particles passing through the sieve)/{(Mass of particles passing through the sieve)+(Mass of particles remaining on the sieve)}×100.

The average particle size is determined by calcining a portion of dry product particles in the air at 400° C. for 1 hour and then measuring the obtained particles using a laser diffraction/scattering method-based particle size distribution analyzer (product name: LS230; manufactured by BECKMAN COULTER, INC.).

The reason for measuring the content of particles having a particle size of 25 µm or smaller after the "calcination in the air at 400° C. for 1 hour" of a portion of the dry product is that the dry product is prevented from being dissolved in water. This means that the "calcination in the air at 400° C. for 1 hour" is performed mainly for the measurement and is not related to the calcination step described later. It is reasonable to think that the particle size hardly changes between before and after this calcination. The rate of reduction of the sample obtained by this calcination may be different from that of the other dry products. However, usually, this sample whose amount is very small hardly influences the performance of the whole catalyst even if the sample is subjected to the calcination step described later, or not. The subject in the measurement of the average particle size may be or may not be the dry product. If necessary, the average particle size of the pre-stage calcined product may be measured.

Examples of the method for preparing particles having a 20% by mass or less content of particles having a particle size of 25 μm or smaller, and an average particle size of 35 to 75 μm include: a method of adjusting spray-drying conditions, for example, the number of rotations of an atomizer, the spray-drying temperature, or the amount of the aqueous mixed solution supplied, and a method which involves classification of the dry product. The method which involves classification of the dry product is not particularly limited. For example, a method using a general apparatus such as a centrifugal classifier, an air classifier, a gravitational classifier, an inertial classifier, a sieve, and a cyclone can be adopted. Among dry- and wet-type classifiers, the dry-type classifier can be used preferably from the viewpoint of, for example, preventing the elution of the catalyst-constituting elements into a solvent, and eliminating adverse effect on catalyst performance. The classifier is adjusted to conditions such that the recovery rate of the dry product in classification is preferably 75% by mass or more, more preferably 80% by mass or more, from the viewpoint of increasing the yield of the oxide catalyst. Alternatively, it is preferable that an apparatus that satisfies the conditions be selected for use.

(d) Calcination Step

The calcination step (hereinafter simply referred to as a "step (d)" at times) is a step of calcining a dry product obtained via the above described drying step. In the present step (d), the dry product obtained by the drying step is calcined to obtain an oxide catalyst.

For example, a rotary kiln or a fluidized calcining furnace can be used as a calcination device. If the dry product is calcined while it is left at rest, it cannot be evenly calcined. As a result, catalytic performance or the like is decreased, and it may also cause breaking, cracking or the like. Accordingly, when continuous calcination is carried out, a rotary kiln is preferably used.

The shape of the calcining device is not particularly limited. From the viewpoint of carrying out continuous calcination, it preferably has a tubular shape (a calcination tube). Moreover, the shape of the calcination tube is not particularly limited. It preferably has a cylindrical shape.

The heating method is preferably an external heating process from the viewpoint of, for example, easily adjusting the calcination temperature to the preferred pattern of temperature rise. An electric furnace can be used preferably. The size and material, and the like of the calcination tube can be selected appropriately according to the calcination conditions or yields. The inside diameter of the calcination tube is preferably 70 to 2000 mm, and more preferably 100 to 1200 mm, from the viewpoint of, for example, preventing uneven calcination temperature distribution in the catalyst layer, and adjusting the calcination time and yields to appropriate values. Moreover, the length of the calcination tube is preferably 200 to 10000 mm, and more preferably 800 to 8000 mm, from the viewpoint of, for example, minimizing the retention time of the dry product and the like in the calcination tube, i.e., calcination time distribution, preventing deformation in the calcination tube, and adjusting the calcination time and yields to appropriate values.

When an impact is given to the calcination tube, the wall thickness of the calcination tube is preferably 2 mm or larger, and more preferably 4 mm or larger, from the viewpoint of maintaining a thickness large enough to prevent the wall from being broken due to the impact. Moreover, the wall thickness is preferably 100 mm or smaller, and more preferably 50 mm or smaller, from the viewpoint of sufficiently transferring the impact to the inside of the calcination tube. The material of the calcination tube is not particularly limited, as long as it preferably has heat resistance and is strong enough to prevent the calcination tube from being broken due to the impact. For example, those made of SUS can be preferably used.

A weir plate having a hole through which the dry product passes in the central portion thereof may be disposed perpendicular (or almost perpendicular) to the flow of the dry product inside the calcination tube, so that the calcination tube can be partitioned into two or more areas. The retention time of the dry product in the calcination tube can be secured easily by the placement of the weir plate. The number of weir plates may be one or two or more. The material of the weir plate is preferably a metal from the viewpoint of improving durability to withstand the calcination atmosphere and heat resistance. The same material as that of the calcination tube can be used preferably. The height of the weir plate can be adjusted according to the retention time to be secured. For example, when the dry product is supplied at a rate of 250 g/hr using a rotary kiln having a calcination tube made of SUS with an inside diameter of 150 mm and a length of 1150 mm, the height of the weir plate is preferably 5 to 50 mm, more preferably 10 to 40 mm, and further preferably 13 to 35 mm. The thickness of the weir plate is not particularly limited and is preferably adjusted according to the size of the calcination tube. For example, in the case of using a rotary kiln having a calcination tube made of SUS with an inside diameter of 150 mm and a length of 1150 mm, the thickness of the weir plate is preferably 0.3 mm or more and 30 mm or less, and more preferably 0.5 mm or more and 15 mm or less.

In the calcination step, in order to prevent breaking, cracking or the like in the dry product and to realize uniform calcination, it is preferable that the calcination be performed, while rotating a calcining device (calcination tube). The rotation rate of the calcining device is preferably 0.1 to 30 rpm, more preferably 0.5 to 20 rpm, and further preferably 1 to 10 rpm.

With regard to the heating temperature in the calcination of the dry product, it is preferable that the dry product be heated at a temperature that starts at a temperature lower than 400° C. and is raised therefrom continuously or gradually to a temperature within the range of 550 to 800° C., from the viewpoint of, for example, achieving a preferred oxidation-reduction state of the obtained catalyst, and improving catalyst performance.

The calcination can be performed in the air atmosphere or under air circulation. However, from the viewpoint of, for example, easily adjusting the catalyst to a preferred oxidation-reduction state, it is preferable that at least a portion of the calcination be carried out while an inert gas (e.g., nitrogen) substantially free from oxygen is circulated.

The amount of the inert gas supplied is preferably 50 to 5000 N/liter, and more preferably 50 to 3000 N/liter, per kg of the dry product, from the viewpoint of adjusting the catalyst to a preferred oxidation-reduction state (wherein the term "N/liter" means a liter measured under standard temperature and pressure conditions, i.e., at 50° C. and a pressure of 1 atmosphere). In this case, the form of the contact between the inert gas and the dry product may be countercurrent contact or may be co-current contact. The countercurrent contact is preferable in consideration of gas components generated from the dry product, and air that may be mixed in a trace amount into the dry product.

The calcination may be carried out at a single stage under constant conditions. However, pre-stage calcination is preferably carried out before main calcination. With regard to temperature range, it is preferable that the pre-stage calcination be performed at 250° C. to 400° C., and that the main calcination be performed at 550° C. to 800° C. The main calcination may be performed continuously from pre-stage calcination, i.e., by directly changing the calcination temperature in the pre-stage calcination to the calcination temperature in the main calcination. Alternatively, the main calcination may be performed by restarting after the completion of pre-stage calcination, i.e., by temporarily decreasing a temperature from the calcination temperature in pre-stage calcination and then raising it to the calcination temperature in the main calcination. Moreover, the pre-stage calcination and the main calcination may each be divided into a plurality of calcination stages differing in calcination conditions.

The pre-stage calcination is performed preferably under inert gas circulation in a heating temperature (pre-stage calcination temperature) range of preferably 250° C. to 400° C., and more preferably 300° C. to 400° C. It is preferable that the pre-stage calcination temperature be maintained at a constant temperature in the heating temperature range of 250° C. to 400° C. However, the temperature may vary in the temperature range of 250° C. to 400° C. or may be raised or decreased moderately. The time for maintaining the heating temperature is preferably 30 minutes or longer, and more preferably 3 to 12 hours.

With regard to the pattern of temperature rise to reach the pre-stage calcination temperature, the temperature may be raised linearly (at a constant temperature rise rate), or the temperature rise pattern may be an upwardly or downwardly curved pattern of temperature rise (while changing the temperature rise rate in the course of temperature rise). The average rate of temperature rise during temperature rise to reach the pre-stage calcination temperature is not particularly limited. It is preferably 0.1° C. to 15° C./min., and more preferably 1° C. to 2° C./min.

From the viewpoint of, for example, easily adjusting the obtained catalyst to a preferred specific surface area, sufficiently forming a reactive crystal structure, and achieving improved catalyst performance, the main calcination is performed preferably under inert gas circulation in a heating temperature (main calcination temperature) range of preferably 550 to 800° C., more preferably 580 to 750° C., further preferably 600 to 720° C., and particularly preferably 620 to 700° C. It is preferable that the heating temperature (main calcination temperature) be maintained at a constant temperature in the temperature range of 620° C. to 700° C. However, the temperature may vary in the temperature range of 620° C. to 700° C. or may be raised or decreased moderately.

The calcination time in main calcination (time for maintaining the calcination temperature) is preferably 0.5 to 20 hours, and more preferably 1 to 15 hours, from the viewpoint of, for example, easily adjusting the obtained catalyst to a preferred specific surface area, sufficiently facilitating the formation of a reactive crystal structure, and achieving improved catalyst performance.

When the calcination tube is partitioned with a weir plate, the dry product continuously passes through at least 2 areas or areas isolated using preferably 2 to 20, and more preferably 4 to 15 weir plates, from the viewpoint of, for example, securing a retention time suitable for the dry product, etc. in the calcination tube. Temperature control can be performed using one or more controller(s). For obtaining the desired calcination pattern, it is preferable that a heater and a controller be placed for temperature control in each of these areas isolated with weir plates. For example, 7 weir plates can be placed to longitudinally divide a portion present in a heating furnace in the calcination tube into 8 equal parts. When the calcination tube thus partitioned into 8 areas is used, it is preferable that the set temperature be controlled using a heater and a controller that are placed in each of these 8 areas such that the temperature of the dry product, etc. exhibits the desired calcination temperature pattern. It is to be noted that an oxidizing component (for example, oxygen) or a reducing component (for example, ammonia) may be added to the calcination atmosphere under inert gas circulation, as desired.

With regard to the pattern of temperature rise to reach the main calcination temperature, the temperature may be raised linearly (at a constant temperature rise rate), or the temperature rise pattern may be an upwardly or downwardly curved pattern of temperature rise (while changing the temperature rise rate in the course of temperature rise). The average rate of temperature rise during temperature rise to reach the main calcination temperature is not particularly limited. From the viewpoint of, for example, easily adjusting the obtained catalyst to a preferred specific surface area, sufficiently forming a reactive crystal structure, and achieving improved catalyst performance, the average rate of temperature rise is preferably 0.1° C. to 15° C./min, and more preferably 1° C. to 8° C./min.

Moreover, from the viewpoint of, for example, sufficiently forming a reactive crystal structure, and achieving improved catalyst performance, the average rate of temperature decrease after completion of the main calcination is preferably 0.01° C. to 1000° C./min, more preferably 0.05° C. to 100° C./min, further preferably 0.1° C. to 50° C./min, and particularly preferably 0.5° C. to 10° C./min. Furthermore, from the viewpoint of, for example, sufficiently forming a reactive crystal structure, and achieving improved catalyst performance, it is also preferable that the resultant is once retained at a temperature lower than the main calcination temperature. From the same viewpoint as described above, the retention temperature is lower than the main calcination temperature by preferably 10° C. or more, more preferably 50° C. or more, and further preferably 100° C. or more. From the same viewpoint as described above, the retention time is preferably 0.5 hours or longer, more preferably 1 hour or longer, further preferably 3 hours or longer, and particularly preferably 10 hours or longer.

When the main calcination is carried out by restarting after completion of the pre-stage calcination, a low-temperature treatment is preferably performed in the main calcination. The time required for the low-temperature treatment, i.e., the time required to decrease the temperature of the pre-stage calcined product and then raise the temperature to reach the main calcinations temperature, can be adjusted, as appropriate, depending on the size, wall thickness, material, and complex oxide yields of a calcining device, a series of periods of time during the continuous calcination of the pre-stage calcined product, the rate of adherence, the amount of particles adhered, etc. For example, when a calcination tube made of SUS with an inside diameter of 500 mm, a length of 4500 mm, and a wall thickness of 20 mm is used, the time required for the above described low-temperature treatment is preferably within 30 days, more preferably within 15 days, further preferably within 3 days, and particularly preferably within 2 days in a series of periods of time during the continuous calcination of the pre-stage calcined product, from the viewpoint of, for example, sufficiently peeling off the pre-stage calcined product and/or catalyst adhered to the wall of the calcination tube, stably maintaining the temperature of the oxide layer, and improving the performance of the obtained catalyst.

(e) Step of Removing Protruding Portion

The oxide catalyst obtained via the calcination step may have a protruding portion that protrudes from the particle surface thereof. If a fluidized bed reaction is carried out using an oxide catalyst having a protruding portion on the particle surface thereof, there is a possibility that fluidity is decreased and the yield of a product of interest cannot be enhanced. Hence, the present embodiment preferably includes a step of removing a protruding portion (hereinafter also referred to as a "step (e)"), and in this step (e), the protruding portion is removed from the oxide catalyst. The mass of the protruding portion remaining in the oxide catalyst after the step (e) has been performed is preferably set at 2% by mass or less based on the mass of the oxide catalyst before the removal of the protruding portion.

If an oxide catalyst used in a fluidized bed reaction has a protruding portion, or if a protruding portion peeled from the oxide catalyst coexists with the oxide catalyst, fluidity is easily decreased. If the fluidity of the oxide catalyst is decreased, an uneven distribution of the oxide catalyst in a reaction vessel takes place with such decrease. As a result, there is a possibility that heat removing efficiency is decreased and heat accumulation causes abnormal reactions, or that the decomposition reaction of a product of interest is promoted depending on the type of the reaction. Moreover, when a part of such a protruding portion is peeled off due to a mutual contact of oxide catalysts in the reaction vessel, etc., and such a peeled part is discharged from the reaction vessel to the outside of the reaction system, it may enter other devices that are connected with the reaction vessel, and as a result, load on the devices may increase. Accordingly, it is preferable that the oxide catalyst do not coexist with the protruding portion in a fluidized bed reaction vessel.

Next, a method for producing an unsaturated acid or an unsaturated nitrile using the thus produced oxide catalyst of the present embodiment will be described. In this production method, propane or isobutane is subjected to a vapor-phase catalytic oxidation or a vapor-phase catalytic ammoxidation reaction in the presence of the above described oxide catalyst, so as to produce the corresponding unsaturared acid or unsaturated nitrile.

Raw materials for propane, isobutane, and ammonia in the case of an ammoxidation reaction are not necessarily high-purity materials, and gas at an industrial grade can be used. As an oxygen-supplying source, air, oxygen-enriched air or pure oxygen can be used. Further, as diluent gas, helium, argon, carbon dioxide, water vapor, nitrogen, etc. may also be supplied.

The vapor-phase catalytic oxidation reaction of propane or isobutane can be carried out, for example, under the following conditions.

The molar ratio of oxygen supplied in the reaction to propane or isobutane is preferably 0.1 to 6, and more preferably 0.5 to 4. The reaction temperature is preferably from 300° C. to 500° C., and more preferably from 350° C. to 450° C. The reaction pressure is preferably from $5 \times 10^4$ to $5 \times 10^5$ Pa, and more preferably from $1 \times 10^5$ to $3 \times 10^5$ Pa. The contact time is preferably 0.1 to 10 (sec·g/cc), and more preferably 0.5 to 5 (sec·g/cc).

In the present embodiment, the contact time is determined by the following formula (G):

$$\text{Contact time (sec·g/cc)} = (W/F) \times 273/(273+T) \quad (G)$$

In the above formula, W indicates the amount of a catalyst filled, F indicates the flow rate of raw material mixed gas (Ncc/sec) in a standard condition (0° C., $1.013 \times 10^5$ Pa), and T indicates a reaction temperature (° C.).

The vapor-phase catalytic ammoxidation reaction of propane or isobutane can be carried out, for example, under the following conditions.

The molar ratio of oxygen supplied in the reaction to propane or isobutane is preferably 0.1 to 6, and more preferably 0.5 to 4. The molar ratio of ammonia supplied in the reaction to propane or isobutane is preferably 0.3 to 1.5, and more preferably 0.7 to 1.2. The reaction temperature is preferably from 350° C. to 500° C., and more preferably from 380° C. to 470° C. The reaction pressure is preferably from $5 \times 10^4$ to $5 \times 10^5$ Pa, and more preferably from $1 \times 10^5$ to $3 \times 10^5$ Pa. The contact time is preferably 0.1 to 10 (sec·g/cc), and more preferably 0.5 to 5 (sec·g/cc).

As a reaction system, a conventional system such as a fixed bed, a fluidized bed or a moving bed can be adopted. From the viewpoint of easy removal of reaction heat, a system using a fluidized bed reaction vessel is preferable. In addition, the vapor-phase catalytic ammoxidation reaction may be either a single flow system or a recycle system.

As given above, the mode for carrying out the present invention has been described. However, the present invention is not limited to the above described present embodiment. The present invention may include various modifications within a range that is not deviated from the gist thereof. For example, in the apparatus for producing a catalyst, the temperature control device may be provided in either the mixed solution tank or the pipe. The temperature control device may be provided only in the mixed solution tank or only in the pipe. Moreover, the apparatus for producing a catalyst may not comprise a pump. For example, if the mixed solution tank 110 and the dryer 120 are disposed such that the aqueous mixed solution discharging port 114 of the mixed solution tank 110 can be positioned higher than the nozzle 122 of the dryer 120, then, an aqueous mixed solution can be directly supplied from the mixed solution tank 110 to the dryer 120 without using a pump.

According to the apparatus and method for producing a catalyst of the present embodiment, the prepared aqueous mixed solution can be smoothly supplied to the dryer. For example, even if the pipe for supplying the prepared aqueous mixed solution to the dryer has a site in which the solution is easily retained, or even if it takes a long period of time from the preparation of the aqueous mixed solution to the drying thereof, gelation of the aqueous mixed solution can be suppressed. In addition, even if the aqueous mixed solution becomes gelatinous, it becomes possible to prevent the clogging of the solution at the pipe or at the spray dryer. Thereby, it becomes possible to stably produce the oxide catalyst, and the catalytic performance of the produced oxide catalyst can be stably enhanced. Moreover, by providing a filtration step, the particle size of the oxide catalyst can be controlled within an appropriate range, and fluidity can be increased during a fluidized bed reaction.

Furthermore, in the present embodiment, a plurality of mixed solution tanks are preferably used. Thereby, the aqueous mixed solution can be continuously supplied to the spray dryer, so as to continuously carry out spray-drying, and thus, the spray-drying step can be carried out continuously under constantly preferred conditions. As a result, catalysts having excellent performance can be produced over a long period of time at a high recovery rate.

EXAMPLES

The present embodiment will be described more in detail in the following examples and comparative examples. However, the scope of the present embodiment is not intended to limit to these examples.

In the examples and the comparative examples, the conversion of propane, the selectivity of acrylonitrile, and the yield of acrylonitrile have definitions represented by the following formulas, respectively.

Propane conversion (%)=(the number of moles of reacted propane)/(the number of moles of supplied propane)×100

Selectivity of acrylonitrile (%)=(the number of moles of produced acrylonitrile)/(the number of reacted propane)×100

Yield of acrylonitrile (%)=(the number of moles of produced acrylonitrile)/(the number of moles of supplied propane)×100

Example 1

Preparation of Niobium Raw Material Solution

A niobium raw material solution was prepared by the following method. First, 500 kg of water was mixed with 76.33 kg of niobium acid containing 80.2% by mass of $Nb_2O_5$ and 290.2 kg of oxalic acid dihydrate [$H_2C_2O_4 \cdot 2H_2O$]. The molar ratio of the feed oxalic acid/niobium was 5.0, and the concentration of the feed niobium was 0.532 (mol-Nb/kg-solution). This solution was heated and stirred at 95° C. for 1 hour to obtain an aqueous solution in which the Nb compound was dissolved. This aqueous solution was allowed to stand and ice-cooled, and then, the solid was filtered off by suction filtration to obtain a uniform aqueous solution of the Nb compound. The same operation was repeated several times, and the obtained aqueous solutions of the Nb compounds were gathered to prepare a niobium raw material solution. The oxalic acid/niobium molar ratio of this niobium raw material solution was found to be 2.4 as a result of the following analysis.

10 g of this niobium raw material solution was precisely weighed into a crucible, was then dried overnight at 95° C., and was then heat-treated at 600° C. for 1 hour to obtain 0.8323 g of $Nb_2O_5$. From this result, the niobium concentration was found to be 0.627 (mol-Nb/kg-solution). 3 g of this niobium raw material solution was precisely weighed into a 300-mL glass beaker. Thereafter, 200 mL of hot water at about 80° C. was added, and 10 mL of 1:1 sulfuric acid was then added. While the obtained mixed solution was maintained at a solution temperature of 70° C. on a hot stirrer, the mixed solution was titrated with stirring, using ¼ normal $KMnO_4$. A point at which a light pale pink color due to $KMnO_4$ lasted for about 30 seconds or more was taken as the end point. The concentration of oxalic acid was calculated from the titer of $KMnO_4$ with reference to the following reaction formula. As a result, the concentration of oxalic acid was found to be 1.50 (mol-oxalic acid/kg).

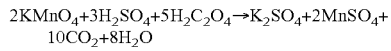

The obtained niobium raw material solution was used as a niobium raw material solution in the subsequent production of an oxide catalyst. The niobium raw material solution was prepared whenever necessary by the same manner as described above, so as to prevent the shortage of the niobium raw material solution used for an aqueous mixed solution.
(Preparation of Aqueous Mixed Solution)

An apparatus for producing a catalyst having the same configuration as that shown in FIG. 1 was prepared. However, the nozzle of a spray dryer 120 was not a two-fluid nozzle but was a centrifugal nozzle. In addition, a Type Y Strainer (manufactured by Washino KiKi Co., Ltd., product name: "type Y strainer," hole diameter: 1.0 mm) was used as a filter 140, and an uniaxial eccentric screw pump (manufactured by HEISHIN Ltd., product name: "Heishin Mono Pump") was used as a pump 160. These components were disposed in a manner opposite to those shown in FIG. 1. As a temperature control device 150 having both heating and cooling functions (pipe system heating/cooling equipment), a heat exchanger having the same heat-transfer pipe 154 as that shown in FIG. 2 was used, and stainless steel was adopted as a material for the heat-transfer pipe 154. The outer surface of a region 154a, on which a heating medium (water) had a high temperature, was coated with a fluorocarbon resin (trade name: "Teflon PTFE," manufactured by Du Pont-Mitsui Fluorochemicals Co., Ltd., wherein "Teflon" is a registered trademark (the same applies below)). As a material for the inner surface of a mixed solution tank 110, a fluorocarbon resin (trade name: "Teflon PTFE," manufactured by Du Pont-Mitsui Fluorochemicals Co., Ltd., wherein "Teflon" is a registered trademark (the same applies below)) was used. As a material for a portion of a pipe L10 that was allowed to come into contact with an aqueous mixed solution, a fluorocarbon resin (trade name: "Teflon PTFE," manufactured by Du Pont-Mitsui Fluorochemicals Co., Ltd.) was used.

First, fouling attached to the inside of the mixed solution tank 110 was washed by a washing device 118 positioned in an upper portion of the mixed solution tank 110 for 1 hour. Thereafter, 300 kg of hot water of 50° C. was poured via a raw material supplying port 112 into the mixed solution tank 110, and it was then stirred and mixed by a stirrer 116 for 5 minutes, so that the mixed solution tank 110 was washed with water.

Subsequently, 100 kg of water, 30.28 kg of ammonium heptamolybdate [$(NH_4)_6Mo_7O_{24} \cdot 4H_2O$], 4.214 kg of ammonium metavanadate [$NH_4VO_3$], 5.52 kg of diantimony trioxide [$Sb_2O_3$], and a cerium nitrate aqueous solution prepared by dissolving 372 g of cerium nitrate [$Ce(NO_3)_3 \cdot 6H_2O$] in 26 kg of water were poured via the raw material supplying port 112 into the mixed solution tank was then heated at 95° C. for 1 hour while stirring, so as to obtain an aqueous raw material solution (I).

Meanwhile, 3.89 kg of a hydrogen peroxide solution containing 30% by mass of $H_2O_2$ was added to 29.4 kg of the above described niobium raw material solution in another vessel. The solution temperature was maintained at approximately 20° C., and the solution was stirred and mixed, so as to obtain an aqueous raw material solution (II).

The obtained aqueous raw material solution (I) was cooled to 70° C. in the mixed solution tank 110, and 59.9 kg of silica sol containing 30.2% by mass of $SiO_2$ was then added thereto. Subsequently, 6.45 kg of a hydrogen peroxide solution containing 30% by mass of $H_2O_2$ was added to the reaction solution, and the obtained solution was then stirred and mixed at 55° C. for 30 minutes. Thereafter, a total amount of the above described aqueous raw material solution (II) and 2.39 kg of an ammonium metatungstate aqueous solution (50% aqueous solution) were further added to the reaction solution. Moreover, 14.8 kg of fumed silica dispersed in 214.7 kg of water was added to the solution, and the thus obtained mixed solution was then aged in an atmosphere having a gas phase oxygen concentration of 18 vol % at 50° C. for 1 hour, so as to obtain an aqueous mixed solution (III) (viscosity at 50° C. 5.0 cp). It is to be noted that Pv=1.0 kW/m³ as a stirring condition.

(Spray-Drying of Aqueous Mixed Solution Obtained in Mixed Solution Tank)

Before completion of the preparation of the aqueous mixed solution (III), the air heated to 210° C. and hot water at 50° C. adjusted to a supply of 80 kg/hr had been supplied via a nozzle to the spray dryer 120, and the inlet temperature of the dryer 120 had been set at 210° C. and the outlet temperature thereof had been set at 120° C. in advance.

After completion of the preparation of the aqueous mixed solution (III) in the mixed solution tank 110, a solution to be supplied to the dryer 120 was immediately switched from hot water to the aqueous mixed solution (III) which was to be supplied from the mixed solution tank 110. The aqueous mixed solution (III) was passed through the pipe L10, the pump 160 and the filter 140 in this order, and was then supplied to the dryer 120. In order to prevent fluctuation in the outlet temperature, the amount of the aqueous mixed solution (III) supplied to spray dryer 120 was controlled. As a result, the supply rate became 100 kg/hr. During this operation, the outlet temperature was 120±5° C., and thus there was no significant fluctuation. After completion of the spray-drying, water was supplied from the dryer 120 to the mixed solution tank 110, and the backwashing of the filter 140 was then carried out for 1 hour.

As described above, the operation from the preparation step in the mixed solution tank 110 to the backwashing of the filter 140 was repeatedly carried out for 1 month. The amount of dry products obtained for 1 month was 28.45 tons, while a theoretical recovered amount calculated from the fed amount was 29.64 tons. The recovery rate was found to be 96.0%.

(Measurement of Ultraviolet-Visible Reflection Spectrum)

The obtained dry product was sampled every other day. Thereafter, a ultraviolet-visible reflection spectrum that targeted 0.5 g out of the obtained 10 sample products was measured according to a diffuse reflection method in a wavelength range from 200 to 800 nm, using a UV/VIS spectrometer manufactured by JASCO Corporation (product name: "JASCO UV/VIS Spectrometer V-650"). As a baseline standard, "SpectraIon" (product name) manufactured by Labsphere was used. The maximum value of absorbance was found to be 1.02. The absorbance at a wavelength of 600 nm was 0.31 to 0.36. Referring to Japanese Patent Application Laid-Open No. 2011-005364, this was an absorbance in which high performance could be anticipated. Accordingly, total quantities of the obtained dry products were used in a classification operation without sorting them.

(Classification Operation)

The obtained dry products were classified using a sieve with a sieve size of 25 μm, so as to obtain a classified product. The content of particles with a size of 25 μm or less in the obtained classified product was found to be 0.8% by mass, and the average particle size was found to be 55 μm.

(Calcination of Classified Product)

The obtained classified product was supplied at a supply rate of 20 kg/hr to a cylindrical calcination tube made of SUS (inside diameter: 500 mm, length: 3500 mm, wall thickness: 20 mm), in which 7 weir plates each having a height of 150 mm were placed to divide the length of a heating furnace portion into 8 equal parts. Then, the heating furnace temperature was controlled to achieve a temperature profile, in which while the calcination tube was rotated at a rotation rate of 4 rotations/min under nitrogen gas circulation of 600 N/liter/min, the temperature was increased to 370° C. over approximately 4 hours, and the temperature was then retained at 370° C. for 3 hours. Thereafter, pre-stage calcination was carried out on the classified product, so as to obtain a pre-stage calcined product. The pre-stage calcined product was supplied at a supply rate of 15 kg/hr to another calcination tube made of SUS (inside diameter: 500 mm, length: 3500 mm, wall thickness: 20 mm), in which 7 weir plates each having a height of 150 mm were placed to divide the length of a heating furnace portion into 8 equal parts, while the calcination tube was rotate at a rate of 4 rotations/min. In this operation, while impacts were given from the direction vertical to the rotation axis that was at a height of 250 mm above the calcination tube to a portion on the pre-stage calcined product introduction side of the calcination tube (portion which is not covered with the heating furnace), at a rate of one impact every 5 seconds, with the use of a hammering device equipped with a hammer with a mass of 14 kg, the tip of the impact portion of which was made of SUS, the heating furnace temperature was controlled to achieve a temperature profile in which the temperature of the calcinations tube was increased to 680° C. at a rate of 2° C./min under nitrogen gas circulation of 500 N/liter/min, calcinations was then carried out at 680° C. for 2 hours, and the temperature was then decreased at a rate of 1° C./min. Then, main calcination was carried out on the pre-stage calcined product, so as to obtain an oxide catalyst.

(Removal of Protruding Portions)

While air was supplied to a vertical tube (inside diameter: 41.6 mm, length: 70 cm) comprising a perforated disk having three holes with a diameter of 1/64 inches at the bottom thereof and a paper filter at the upper portion thereof, 50 g of the oxide catalyst was poured therein. In this operation, the length of air current in the direction in which the air current flowed was 52 mm, and the average linear velocity of the air current was 310 m/s. Twenty-four hours later, the obtained oxide catalyst was observed by SEM. As a result, no protruding portions could be confirmed on the surface of the oxide catalyst.

(Ammoxidation Reaction of Propane)

Using the above obtained oxide catalyst, propane was subjected to a vapor phase ammoxidation reaction by the following method. That is, a Vycor glass fluidized bed reaction tube with an inside diameter of 25 mm was filled with 35 g of the oxide catalyst, and the reaction temperature was set at 440° C. and the reaction pressure was set at ordinary pressure. Thereafter, mixed gas consisting of propane, ammonia, oxygen and helium (propane:ammonia:oxygen:helium=1:1:3:18 (molar ratio)) was supplied at a constant time of 2.8 (sec·g/cc). After completion of the reaction, the propane conversion was found to be 89.5%, and the yield of acrylonitrile was found to be 53.5%.

Example 2

Preparation of Niobium Raw Material Solution

A niobium raw material solution was prepared in the same manner as that of Example 1.

(Preparation of Aqueous Mixed Solution)

As a temperature control device 150 having both heating and cooling functions (pipe system heating/cooling equipment), a heat exchanger having the same heat-transfer pipe 154 as that shown in FIG. 2 was used, and stainless steel was adopted as a material for the heat-transfer pipe 154. The outer surface of a region 154a, on which a heating medium had a high temperature, was coated with a fluorocarbon resin (trade name: "Teflon PFA," manufactured by Du Pont-Mitsui Fluorochemicals Co., Ltd.). As a material for the inner surface of a mixed solution tank 110, a fluorocarbon resin (trade name: "Teflon PFA," manufactured by Du Pont-Mitsui Fluorochemicals Co., Ltd.) was used. As a material for a portion of a pipe L10 that was allowed to come into contact with an aqueous mixed solution, a fluorocarbon resin (trade name:

"Teflon PFA," manufactured by Du Pont-Mitsui Fluorochemicals Co., Ltd.) was used. Other than these exceptions, an apparatus for producing a catalyst comprising the same configuration as that of Example 1 was used.

First, 300 kg of hot water of 50° C. was poured via a raw material supplying port 112 into the mixed solution tank 110, and it was then stirred and mixed by a stirrer 116 for 5 minutes, so that the mixed solution tank 110 was washed with water.

Subsequently, 100 kg of water, 30.28 kg of ammonium heptamolybdate [$(NH_4)_6Mo_7O_{24}.4H_2O$], 4.214 kg of ammonium metavanadate [$NH_4VO_3$], 5.52 kg of diantimony trioxide [$Sb_2O_3$], and a cerium nitrate aqueous solution prepared by dissolving 372 g of cerium nitrate [$Ce(NO_3)_3.6H_2O$] in 26 kg of water were poured via the raw material supplying port 112 into the mixed solution tank was then heated at 95° C. for 1 hour while stirring, so as to obtain an aqueous raw material solution (I).

Meanwhile, 3.89 kg of a hydrogen peroxide solution containing 30% by mass of $H_2O_2$ was added to 29.4 kg of the above described niobium raw material solution in another vessel. The solution temperature was maintained at approximately 20° C., and the solution was stirred and mixed, so as to obtain an aqueous raw material solution (II).

The obtained aqueous raw material solution (I) was cooled to 70° C. in the mixed solution tank 110, and 59.9 kg of silica sol containing 30.2% by mass of $SiO_2$ was then added thereto. Subsequently, 6.45 kg of a hydrogen peroxide solution containing 30% by mass of $H_2O_2$ was added to the reaction solution, and the obtained solution was then stirred and mixed at 55° C. for 30 minutes. Thereafter, a total amount of the above described aqueous raw material solution (II) and 2.39 kg of an ammonium metatungstate aqueous solution (50% aqueous solution) were further added to the reaction solution. Moreover, 14.8 kg of fumed silica dispersed in 214.7 kg of water was added to the solution, and the thus obtained mixed solution was then aged in an atmosphere having a gas phase oxygen concentration of 18 vol % at 50° C. for 1 hour, so as to obtain an aqueous mixed solution (III) (viscosity at 50° C.: 5.0 cp). It is to be noted that Pv=1.0 kW/m³ as a stirring condition.

(Spray-Drying of Aqueous Mixed Solution Obtained in Mixed Solution Tank)

Before completion of the preparation of the aqueous mixed solution (III), the air heated to 210° C. and hot water at 50° C. adjusted to a supply of 80 kg/hr had been supplied via a nozzle to the spray dryer 120, and the inlet temperature of the dryer 120 had been set at 210° C. and the outlet temperature thereof had been set at 120° C. in advance.

After completion of the preparation of the aqueous mixed solution (III) in the mixed solution tank 110, a solution to be supplied to the dryer 120 was immediately switched from hot water to the aqueous mixed solution (III) which was to be supplied from the mixed solution tank 110. The aqueous mixed solution (III) was passed through the pipe L10, the pump 160 and the filter 140 in this order, and was then supplied to the dryer 120. In order to prevent fluctuation in the outlet temperature, the amount of the aqueous mixed solution (III) supplied to spray dryer 120 was controlled. As a result, the supply rate became 100 kg/hr. During this operation, the outlet temperature was 120±5° C., and thus there was no significant fluctuation. After completion of the spray-drying, water was supplied from the dryer 120 to the mixed solution tank 110, and the backwashing of the filter 140 was then carried out for 1 hour.

As described above, the operation from the preparation step in the mixed solution tank 110 to the backwashing of the filter 140 was repeatedly carried out for 1 month. The amount of dry products obtained for 1 month was 27.68 tons, while a theoretical recovered amount calculated from the fed amount was 29.64 tons. The recovery rate was found to be 93.4%.

(Measurement of Ultraviolet-Visible Reflection Spectrum)

The obtained dry product was sampled every other day. Thereafter, a ultraviolet-visible reflection spectrum that targeted 0.5 g out of the obtained 10 sample products was measured according to a diffuse reflection method in a wavelength range from 200 to 800 nm, using a UV/VIS spectrometer manufactured by JASCO Corporation (product name: "JASCO UV/VIS Spectrometer V-650"). As a baseline standard, "SpectraIon" (product name) manufactured by Labspere was used. The maximum value of absorbance was found to be 1.02. The absorbance at a wavelength of 600 nm was 0.31 to 0.36. Referring to Japanese Patent Application Laid-Open No. 2011-005364, this was an absorbance in which high performance could be anticipated. Accordingly, total quantities of the obtained dry products were used in a classification operation without sorting them.

(Classification Operation)

The obtained dry products were classified using a sieve with a sieve size of 25 μm, so as to obtain a classified product. The content of particles with a size of 25 μm or less in the obtained classified product was found to be 1.0% by mass, and the average particle size was found to be 53 μm.

(Calcination of Classified Product)

The obtained classified product was calcined in the same manner as that of Example 1.

(Removal of Protruding Portions)

Removal of protruding portions was carried out in the same manner as that of Example 1. Twenty-four hours later, the obtained oxide catalyst was observed by SEM. As a result, no protruding portions could be confirmed on the surface of the oxide catalyst.

(Ammoxidation Reaction of Propane)

Using the above obtained oxide catalyst, propane was subjected to a vapor phase ammoxidation reaction by the following method. That is, a Vycor glass fluidized bed reaction tube with an inside diameter of 25 mm was filled with 35 g of the oxide catalyst, and the reaction temperature was set at 440° C. and the reaction pressure was set at ordinary pressure. Thereafter, mixed gas consisting of propane, ammonia, oxygen and helium (propane:ammonia:oxygen:helium=1:1:3:18 (molar ratio)) was supplied at a constant time of 2.8 (sec·g/cc). After completion of the reaction, the propane conversion was found to be 89.0%, and the yield of acrylonitrile was found to be 53.1%.

Example 3

Preparation of Niobium Raw Material Solution

A niobium raw material solution was prepared in the same manner as that of Example 1.

(Preparation of Aqueous Mixed Solution)

As a temperature control device 150 having both heating and cooling functions (pipe system heating/cooling equipment), a heat exchanger having the same heat-transfer pipe 154 as that shown in FIG. 2 was used, and a fluorocarbon resin (trade name: "Teflon PFA," manufactured by Du Pont-Mitsui Fluorochemicals Co., Ltd.) was used as a material for the heat-transfer pipe 154. As a material for the inner surface of a mixed solution tank 110, a fluorocarbon resin (trade name: "Teflon PTFE," manufactured by Du Pont-Mitsui Fluorochemicals Co., Ltd.) was used. Other than these exceptions, an apparatus for producing a catalyst comprising the same configuration as that of Example 1 was used.

First, fouling attached to the inside of the mixed solution tank 110 was washed by a washing device 118 positioned in an upper portion of the mixed solution tank 110 for 1 hour. Thereafter, 300 kg of hot water of 50° C. was poured via a raw material supplying port 112 into the mixed solution tank 110, and it was then stirred and mixed by a stirrer 116 for 5 minutes, so that the mixed solution tank 110 was washed with water.

Subsequently, 100 kg of water, 30.28 kg of ammonium heptamolybdate [$(NH_4)_6Mo_7O_{24}\cdot 4H_2O$], 4.214 kg of ammonium metavanadate [$NH_4VO_3$], 5.52 kg of diantimony trioxide [$Sb_2O_3$], and a cerium nitrate aqueous solution prepared by dissolving 372 g of cerium nitrate [$Ce(NO_3)_3\cdot 6H_2O$] in 26 kg of water were poured via the raw material supplying port 112 into the mixed solution tank was then heated at 95° C. for 1 hour while stirring, so as to obtain an aqueous raw material solution (I).

Meanwhile, 3.89 kg of a hydrogen peroxide solution containing 30% by mass of $H_2O_2$ was added to 29.4 kg of the above described niobium raw material solution in another vessel. The solution temperature was maintained at approximately 20° C., and the solution was stirred and mixed, so as to obtain an aqueous raw material solution (II).

The obtained aqueous raw material solution (I) was cooled to 70° C. in the mixed solution tank 110, and 59.9 kg of silica sol containing 30.2% by mass of $SiO_2$ was then added thereto. Subsequently, 6.45 kg of a hydrogen peroxide solution containing 30% by mass of $H_2O_2$ was added to the reaction solution, and the obtained solution was then stirred and mixed at 55° C. for 30 minutes. Thereafter, a total amount of the above described aqueous raw material solution (II) and 2.39 kg of an ammonium metatungstate aqueous solution (50% aqueous solution) were further added to the reaction solution. Moreover, 14.8 kg of fumed silica dispersed in 214.7 kg of water was added to the solution, and the thus obtained mixed solution was then aged in an atmosphere having a gas phase oxygen concentration of 18 vol % at 50° C. for 1 hour, so as to obtain an aqueous mixed solution (III) (viscosity at 50° C.: 5.0 cp). It is to be noted that Pv=1.0 kW/m³ as a stirring condition.

(Spray-Drying of Aqueous Mixed Solution Obtained in Mixed Solution Tank)

Before completion of the preparation of the aqueous mixed solution (III), the air heated to 210° C. and hot water at 50° C. adjusted to a supply of 80 kg/hr had been supplied via a nozzle to the spray dryer 120, and the inlet temperature of the dryer 120 had been set at 210° C. and the outlet temperature thereof had been set at 120° C. in advance.

After completion of the preparation of the aqueous mixed solution (III) in the mixed solution tank 110, a solution to be supplied to the dryer 120 was immediately switched from hot water to the aqueous mixed solution (III) which was to be supplied from the mixed solution tank 110. The aqueous mixed solution (III) was passed through the pipe L10, the pump 160 and the filter 140 in this order, and was then supplied to the dryer 120. In order to prevent fluctuation in the outlet temperature, the amount of the aqueous mixed solution (III) supplied to spray dryer 120 was controlled. As a result, the supply rate became 100 kg/hr. During this operation, the outlet temperature was 120±5° C., and thus there was no significant fluctuation. After completion of the spray-drying, water was supplied from the dryer 120 to the mixed solution tank 110, and the backwashing of the filter 140 was then carried out for 1 hour.

As described above, the operation from the preparation step in the mixed solution tank 110 to the backwashing of the filter 140 was repeatedly carried out for 1 month. The amount of dry products obtained for 1 month was 28.60 tons, while a theoretical recovered amount calculated from the fed amount was 29.64 tons. The recovery rate was found to be 96.5%.

(Measurement of Ultraviolet-Visible Reflection Spectrum)

The obtained dry product was sampled every other day. Thereafter, a ultraviolet-visible reflection spectrum that targeted 0.5 g out of the obtained 10 sample products was measured according to a diffuse reflection method in a wavelength range from 200 to 800 nm, using a UV/VIS spectrometer manufactured by JASCO Corporation (product name: "JASCO UV/VIS Spectrometer V-650"). As a baseline standard, "SpectraIon" (product name) manufactured by Labspere was used. The maximum value of absorbance was found to be 1.02. The absorbance at a wavelength of 600 nm was 0.31 to 0.36. Referring to Japanese Patent Application Laid-Open No. 2011-005364, this was an absorbance in which high performance could be anticipated. Accordingly, total quantities of the obtained dry products were used in a classification operation without sorting them.

(Classification Operation)

The obtained dry products were classified using a sieve with a sieve size of 25 μm, so as to obtain a classified product. The content of particles with a size of 25 μm or less in the obtained classified product was found to be 0.8% by mass, and the average particle size was found to be 55 μm.

(Calcination of Classified Product)

The obtained classified product was calcined in the same manner as that of Example 1.

(Removal of Protruding Portions)

Removal of protruding portions was carried out in the same manner as that of Example 1. Twenty-four hours later, the obtained oxide catalyst was observed by SEM. As a result, no protruding portions could be confirmed on the surface of the oxide catalyst.

(Ammoxidation Reaction of Propane)

Using the above obtained oxide catalyst, propane was subjected to a vapor phase ammoxidation reaction by the following method. That is, a Vycor glass fluidized bed reaction tube with an inside diameter of 25 mm was filled with 35 g of the oxide catalyst, and the reaction temperature was set at 440° C. and the reaction pressure was set at ordinary pressure. Thereafter, mixed gas consisting of propane, ammonia, oxygen and helium (propane:ammonia:oxygen:helium=1:1:3:18 (molar ratio)) was supplied at a constant time of 2.8 (sec·g/cc). After completion of the reaction, the propane conversion was found to be 88.9%, and the yield of acrylonitrile was found to be 53.1%.

Example 4

Preparation of Niobium Raw Material Solution

A niobium raw material solution was prepared in the same manner as that of Example 1.

(Preparation of Aqueous Mixed Solution)

A type Y strainer (manufactured by KITZ Corporation, product name: Type Y Strainer, hole diameter: 1.4 mm) was used as filter 140, and a screw pump (manufactured by Iwaki Co., Ltd., product name: Screw Pump) was used as a pump 160. As a temperature control device 150 having both heating and cooling functions (pipe system heating/cooling equipment), a heat exchanger having the same heat-transfer pipe 154 as that shown in FIG. 2 was used, and stainless steel was adopted as a material for the heat-transfer pipe 154. As a material for the inner surface of a mixed solution tank 110, and as a material for a portion of a pipe L10 that was allowed to come into contact with the aqueous mixed solution (III), stainless steel was used. Other than these exceptions, an apparatus for producing a catalyst comprising the same configuration as that of Example 1 was used.

First, fouling attached to the inside of the mixed solution tank 110 was washed by a washing device 118 positioned in an upper portion of the mixed solution tank 110 for 1 hour. Thereafter, 300 kg of hot water of 50° C. was poured via a raw material supplying port 112 into the mixed solution tank 110, and it was then stirred and mixed by a stirrer 116 for 5 minutes, so that the mixed solution tank 110 was washed with water.

Subsequently, 100 kg of water, 30.28 kg of ammonium heptamolybdate [$(NH_4)_6Mo_7O_{24} \cdot 4H_2O$], 4.214 kg of ammonium metavanadate [$NH_4VO_3$], 5.52 kg of diantimony trioxide [$Sb_2O_3$], and a cerium nitrate aqueous solution prepared by dissolving 372 g of cerium nitrate [$Ce(NO_3)_3 \cdot 6H_2O$] in 26 kg of water were poured via the raw material supplying port 112 into the mixed solution tank was then heated at 95° C. for 1 hour while stirring, so as to obtain an aqueous raw material solution (I).

Meanwhile, 3.89 kg of a hydrogen peroxide solution containing 30% by mass of $H_2O_2$ was added to 29.4 kg of the above described niobium raw material solution in another vessel. The solution temperature was maintained at approximately 20° C., and the solution was stirred and mixed, so as to obtain an aqueous raw material solution (II).

The obtained aqueous raw material solution (I) was cooled to 70° C. in the mixed solution tank 110, and 59.9 kg of silica sol containing 30.2% by mass of $SiO_2$ was then added thereto. Subsequently, 6.45 kg of a hydrogen peroxide solution containing 30% by mass of $H_2O_2$ was added to the reaction solution, and the obtained solution was then stirred and mixed at 55° C. for 30 minutes. Thereafter, a total amount of the above described aqueous raw material solution (II) and 2.39 kg of an ammonium metatungstate aqueous solution (50% aqueous solution) were further added to the reaction solution. Moreover, 14.8 kg of fumed silica dispersed in 214.7 kg of water was added to the solution, and the thus obtained mixed solution was then aged in an atmosphere having a gas phase oxygen concentration of 18 vol % at 50° C. for 1 hour, so as to obtain an aqueous mixed solution (III) (viscosity at 50° C.: 5.0 cp). It is to be noted that Pv=1.0 kW/m³ as a stirring condition.

(Spray-Drying of Aqueous Mixed Solution Obtained in Mixed Solution Tank)

Before completion of the preparation of the aqueous mixed solution (III), the air heated to 210° C. and hot water at 50° C. adjusted to a supply of 80 kg/hr had been supplied via a nozzle to the spray dryer 120, and the inlet temperature of the dryer 120 had been set at 210° C. and the outlet temperature thereof had been set at 120° C. in advance.

After completion of the preparation of the aqueous mixed solution (III) in the mixed solution tank 110, a solution to be supplied to the dryer 120 was immediately switched from hot water to the aqueous mixed solution (III) which was to be supplied from the mixed solution tank 110. The aqueous mixed solution (III) was passed through the pipe L10, the pump 160 and the filter 140 in this order, and was then supplied to the dryer 120. In order to prevent fluctuation in the outlet temperature, the amount of the aqueous mixed solution (III) supplied to spray dryer 120 was controlled. As a result, the supply rate became 100 kg/hr. During this operation, the outlet temperature was 120±5° C., and thus there was no significant fluctuation. After completion of the spray-drying, water was supplied from the dryer 120 to the mixed solution tank 110, and the backwashing of the filter 140 was then carried out for 1 hour.

As described above, the operation from the preparation step in the mixed solution tank 110 to the backwashing of the filter 140 was repeatedly carried out for 1 month. The amount of dry products obtained for 1 month was 27.57 tons, while a theoretical recovered amount calculated from the fed amount was 29.64 tons. The recovery rate was found to be 93.0%.

(Measurement of Ultraviolet-Visible Reflection Spectrum)

The obtained dry product was sampled every other day. Thereafter, a ultraviolet-visible reflection spectrum that targeted 0.5 g out of the obtained 10 sample products was measured according to a diffuse reflection method in a wavelength range from 200 to 800 nm, using a UV/VIS spectrometer manufactured by JASCO Corporation (product name: "JASCO UV/VIS Spectrometer V-650"). As a baseline standard, "SpectraIon" (product name) manufactured by Labspere was used. The maximum value of absorbance was found to be 1.02. The absorbance at a wavelength of 600 nm was 0.31 to 0.36. Referring to Japanese Patent Application Laid-Open No. 2011-005364, this was an absorbance in which high performance could be anticipated. Accordingly, total quantities of the obtained dry products were used in a classification operation without sorting them.

(Classification Operation)

The obtained dry products were classified using a sieve with a sieve size of 25 μm, so as to obtain a classified product. The content of particles with a size of 25 μm, or less in the obtained classified product was found to be 1.2% by mass, and the average particle size was found to be 52 μm.

(Calcination of Classified Product)

The obtained classified product was calcined in the same manner as that of Example 1.

(Removal of Protruding Portions)

Removal of protruding portions was carried out in the same manner as that of Example 1. Twenty-four hours later, the obtained oxide catalyst was observed by SEM. As a result, no protruding portions could be confirmed on the surface of the oxide catalyst.

(Ammoxidation Reaction of Propane)

Using the above obtained oxide catalyst, propane was subjected to a vapor phase ammoxidation reaction by the following method. That is, a Vycor glass fluidized bed reaction tube with an inside diameter of 25 mm was filled with 35 g of the oxide catalyst, and the reaction temperature was set at 440° C. and the reaction pressure was set at ordinary pressure. Thereafter, mixed gas consisting of propane, ammonia, oxygen and helium (propane:ammonia:oxygen:helium=1:1:3:18 (molar ratio)) was supplied at a constant time of 2.8 (sec·g/cc). After completion of the reaction, the propane conversion was found to be 88.9%, and the yield of acrylonitrile was found to be 52.9%.

Example 5

Preparation of Niobium Raw Material Solution

A niobium raw material solution was prepared in the same manner as that of Example 1.

(Preparation of Aqueous Mixed Solution)

The same apparatus for producing a catalyst as that of Example 3 was used.

First, 300 kg of hot water of 50° C. was poured via a raw material supplying port 112 into the mixed solution tank 110, and it was then stirred and mixed by a stirrer 116 for 5 minutes, so that the mixed solution tank 110 was washed with water.

Subsequently, 100 kg of water, 30.28 kg of ammonium heptamolybdate [$(NH_4)_6Mo_7O_{24}\cdot 4H_2O$], 4.214 kg of ammonium metavanadate [$NH_4VO_3$], 5.52 kg of diantimony trioxide [$Sb_2O_3$], and a cerium nitrate aqueous solution prepared by dissolving 372 g of cerium nitrate [$Ce(NO_3)_3\cdot 6H_2O$] in 26 kg of water were poured via the raw material supplying port 112 into the mixed solution tank was then heated at 95° C. for 1 hour while stirring, so as to obtain an aqueous raw material solution (I).

Meanwhile, 3.89 kg of a hydrogen peroxide solution containing 30% by mass of $H_2O_2$ was added to 29.4 kg of the above described niobium raw material solution in another vessel. The solution temperature was maintained at approximately 20° C., and the solution was stirred and mixed, so as to obtain an aqueous raw material solution (II).

The obtained aqueous raw material solution (I) was cooled to 70° C. in the mixed solution tank 110, and 59.9 kg of silica sol containing 30.2% by mass of $SiO_2$ was then added thereto. Subsequently, 6.45 kg of a hydrogen peroxide solution containing 30% by mass of $H_2O_2$ was added to the reaction solution, and the obtained solution was then stirred and mixed at 55° C. for 30 minutes. Thereafter, a total amount of the above described aqueous raw material solution (II) and 2.39 kg of an ammonium metatungstate aqueous solution (50% aqueous solution) were further added to the reaction solution. Moreover, 14.8 kg of fumed silica dispersed in 214.7 kg of water was added to the solution, and the thus obtained mixed solution was then aged in an atmosphere having a gas phase oxygen concentration of 18 vol % at 50° C. for 1 hour, so as to obtain an aqueous mixed solution (III) (viscosity at 50° C.: 5.0 cp). It is to be noted that Pv=1.0 kW/m³ as a stirring condition.

(Spray-Drying of Aqueous Mixed Solution Obtained in Mixed Solution Tank)

Before completion of the preparation of the aqueous mixed solution (III), the air heated to 210° C. and hot water at 50° C. adjusted to a supply of 80 kg/hr had been supplied via a nozzle to the spray dryer 120, and the inlet temperature of the dryer 120 had been set at 210° C. and the outlet temperature thereof had been set at 120° C. in advance.

After completion of the preparation of the aqueous mixed solution (III) in the mixed solution tank 110, a solution to be supplied to the dryer 120 was immediately switched from hot water to the aqueous mixed solution (III) which was to be supplied from the mixed solution tank 110. The aqueous mixed solution (III) was passed through the pipe L10, the pump 160 and the filter 140 in this order, and was then supplied to the dryer 120. In order to prevent fluctuation in the outlet temperature, the amount of the aqueous mixed solution (III) supplied to spray dryer 120 was controlled. As a result, the supply rate became 100 kg/hr. During this operation, the outlet temperature was 120±5° C., and thus there was no significant fluctuation. After completion of the spray-drying, water was supplied from the dryer 120 to the mixed solution tank 110, and the backwashing of the filter 140 was then carried out for 1 hour.

As described above, the operation from the preparation step in the mixed solution tank 110 to the backwashing of the filter 140 was repeatedly carried out for 1 month. The amount of dry products obtained for 1 month was 26.68 tons, while a theoretical recovered amount calculated from the fed amount was 29.64 tons. The recovery rate was found to be 90.0%.

(Measurement of Ultraviolet-Visible Reflection Spectrum)

The obtained dry product was sampled every other day. Thereafter, a ultraviolet-visible reflection spectrum that targeted 0.5 g out of the obtained 10 sample products was measured according to a diffuse reflection method in a wavelength range from 200 to 800 nm, using a UV/VIS spectrometer manufactured by JASCO Corporation (product name: "JASCO UV/VIS Spectrometer V-650"). As a baseline standard, "SpectraIon" (product name) manufactured by Labspere was used. The maximum value of absorbance was found to be 1.02. The absorbance at a wavelength of 600 nm was 0.31 to 0.36. Referring to Japanese Patent Application Laid-Open No. 2011-005364, this was an absorbance in which high performance could be anticipated. Accordingly, total quantities of the obtained dry products were used in a classification operation without sorting them.

(Classification Operation)

The obtained dry products were classified using a sieve with a sieve size of 25 µm, so as to obtain a classified product. The content of particles with a size of 25 µm or less in the obtained classified product was found to be 1.4% by mass, and the average particle size was found to be 50 µm.

(Calcination of Classified Product)

The obtained classified product was calcined in the same manner as that of Example 1.

(Removal of Protruding Portions)

Removal of protruding portions was carried out in the same manner as that of Example 1. Twenty-four hours later, the obtained oxide catalyst was observed by SEM. As a result, no protruding portions could be confirmed on the surface of the oxide catalyst.

(Ammoxidation Reaction of Propane)

Using the above obtained oxide catalyst, propane was subjected to a vapor phase ammoxidation reaction by the following method. A Vycor glass fluidized bed reaction tube with an inside diameter of 25 mm was filled with 35 g of the oxide catalyst, and the reaction temperature was set at 440° C. and the reaction pressure was set at ordinary pressure. Thereafter, mixed gas consisting of propane, ammonia, oxygen and helium (propane:ammonia:oxygen:helium=1:1:3:18 (molar ratio)) was supplied at a constant time of 2.8 (sec·g/cc). After completion of the reaction, the propane conversion was found to be 88.5%, and the yield of acrylonitrile was found to be 52.5%.

Example 6

Preparation of Niobium Raw Material Solution

A niobium raw material solution was prepared in the same manner as that of Example 1.

(Preparation of Aqueous Mixed Solution)

An apparatus for producing a catalyst comprising the same configuration as that of Example 1 was used with the exceptions that two mixed solution tanks 110 were used, and that as shown in FIG. 5, the two mixed solution tanks were connected with a dryer 120 by a pipe L10.

(Preparation of Aqueous Mixed Solution in First Mixed Solution Tank)

First, by a washing device 118 positioned in an upper portion in one mixed solution tank of the two mixed solution tanks (hereinafter referred to as a "first mixed solution tank 110"), fouling attached to the inside of the first mixed solution tank 110 was washed for 5 minutes. Moreover, 300 kg of hot water of 50° C. was poured via a raw material supplying port 112 into the first mixed solution tank 110, and it was then stirred and mixed by a stirrer 116 for 5 minutes, so that the first mixed solution tank 110 was washed with water.

Subsequently, 100 kg of water, 30.28 kg of ammonium heptamolybdate [$(NH_4)_6Mo_7O_{24}.4H_2O$], 4.214 kg of ammonium metavanadate [$NH_4VO_3$], 5.52 kg of diantimony trioxide [$Sb_2O_3$], and a cerium nitrate aqueous solution prepared by dissolving 372 g of cerium nitrate [$Ce(NO_3)_3.6H_2O$] in 26 kg of water were poured into the first mixed solution tank 110, and the obtained mixed solution was then heated at 95° C. for 1 hour while stirring, so as to obtain an aqueous raw material solution (I).

Meanwhile, 3.89 kg of a hydrogen peroxide solution containing 30% by mass of $H_2O_2$ was added to 29.4 kg of the above described niobium raw material solution in another vessel. The solution temperature was maintained at approximately 20° C., and the solution was stirred and mixed, so as to obtain an aqueous raw material solution (II).

The obtained aqueous raw material solution (I) was cooled to 70° C. in the first mixed solution tank 110, and 59.9 kg of silica sol containing 30.2% by mass of $SiO_2$ was then added thereto. Subsequently, 6.45 kg of a hydrogen peroxide solution containing 30% by mass of $H_2O_2$ was added to the reaction solution, and the obtained solution was then stirred and mixed at 55° C. for 30 minutes. Thereafter, a total amount of the above described aqueous raw material solution (II) and 2.39 kg of an ammonium metatungstate aqueous solution (50% aqueous solution) were further added to the reaction solution. Moreover, 14.8 kg of fumed silica dispersed in 214.7 kg of water was added to the solution, and the thus obtained mixed solution was then aged in an atmosphere having a gas phase oxygen concentration of 18 vol % at 50° C. for 1 hour, so as to obtain an aqueous mixed solution (III) (viscosity at 50° C.: 5.0 cp). It is to be noted that Pv=1.0 kW/m³ as a stirring condition. The time for preparing the aqueous mixed solution in the first mixed solution tank, which included the water-washing operation, was 4 hours.

(Spray-Drying of Aqueous Mixed Solution Obtained in First Mixed Solution Tank)

Before completion of the preparation of the aqueous mixed solution (III), the air heated to 210° C. and hot water at 50° C. adjusted to a supply of 80 kg/hr had been supplied via a nozzle to the spray dryer 120, and the inlet temperature of the dryer 120 had been set at 210° C. and the outlet temperature thereof had been set at 120° C. in advance.

After completion of the preparation of the aqueous mixed solution (III) in the first mixed solution tank 110, a solution to be supplied to the dryer 120 was immediately switched from hot water to the aqueous mixed solution (III) which was supplied from the first mixed solution tank 110. The aqueous mixed solution (III) was passed through the pipe L10, the pump 160 and the filter 140 in this order, and was then supplied to the dryer 120. In order to prevent fluctuation in the outlet temperature, the amount of the aqueous mixed solution (III) supplied to spray dryer 120 was controlled. As a result, the supply rate became 100 kg/hr. The spray-drying was continued until the preparation of an aqueous mixed solution in the second mixed solution tank 110 was completed, and during this operation, the outlet temperature was 120±5° C., and thus there was no significant fluctuation. The total spray-drying time was 4 hours. After completion of the spray-drying, water was supplied from the dryer 120 to the first mixed solution tank 110, and the backwashing of the filter 140 was then carried out for 5 minutes.

(Preparation of Aqueous Mixed Solution in Second Mixed Solution Tank)

After the preparation of the aqueous mixed solution (III) in the first mixed solution tank had been complete, a solution to be supplied to the spray dryer was switched from hot water to the aqueous mixed solution (III) prepared in the first mixed solution tank. Thereafter, the preparation of an aqueous mixed solution (III) was initiated in the other tank of the two mixed solution tanks 110 (hereinafter referred to as a "second mixed solution tank 110"). The preparation of the aqueous mixed solution (III) in the second mixed solution tank 110, which included the water-washing of the second mixed solution tank 110, was carried out in the same manner as that for the preparation of the aqueous mixed solution (III) in the first mixed solution tank 110. The time for preparing the aqueous mixed solution (III) in the second mixed solution tank 110 was 3 hours and 55 minutes. When the preparation of the aqueous mixed solution (III) in the second mixed solution tank was completed, the spray-drying operation in the first mixed solution tank 110 has not yet been completed. Therefore, the aging operation was extended, and the next operation was suspended.

(Spray-Drying of Aqueous Mixed Solution Obtained in Second Mixed Solution Tank)

While the aging operation was extended for 5 minutes and the next operation was suspended, the spray-drying of the aqueous mixed solution (III) prepared in the first mixed solution tank 110 was completed. Thus, it was switched to the spray-drying of the aqueous mixed solution (III) prepared in the second mixed solution tank 110. This spray-drying was carried out under the same conditions as those for the spray-drying of the aqueous mixed solution (III) prepared in the first mixed solution tank 110. When the spray-drying of the aqueous mixed solution (III) prepared in the first mixed solution tank 110 was switched to the spray-drying of the aqueous mixed solution (III) prepared in the second mixed solution tank 110, the outlet temperature of the dryer 120 was somewhat fluctuated, but it was within 120±5° C. The total spray-drying time was 4 hours. As described above, the spray-drying of the aqueous mixed solution (III) prepared in the first mixed solution tank 110 and the spray-drying of the aqueous mixed solution (III) prepared in the second mixed solution tank 110 were repeatedly carried out, so that continuous spray-drying could be carried out substantially without interrupting spray-drying. The amount of dry products obtained by the continuous spray-drying for 1 month was 28.75 tons, while a theoretical recovered amount calculated from the fed amount was 29.64 tons. The recovery rate was found to be 97.0%.

(Measurement of Ultraviolet-Visible Reflection Spectrum)

The obtained dry product was sampled every other day. Thereafter, a ultraviolet-visible reflection spectrum that targeted 0.5 g out of the obtained 10 sample products was measured according to a diffuse reflection method in a wavelength range from 200 to 800 nm, using a UV/VIS spectrometer manufactured by JASCO Corporation (product name: "JASCO UV/VIS Spectrometer V-650"). As a baseline standard, "SpectraIon" (product name) manufactured by Labspere was used. The maximum value of absorbance was found to be 1.02. The absorbance at a wavelength of 600 nm was 0.31 to 0.36. Referring to Japanese Patent Application Laid-Open No. 2011-005364, this was an absorbance in which high performance could be anticipated. Accordingly, total quantities of the obtained dry products were used in a classification operation without sorting them.

(Classification Operation)

The obtained dry products were classified using a sieve with a sieve size of 25 μm, so as to obtain a classified product. The content of particles with a size of 25 μm or less in the obtained classified product was found to be 0.8% by mass, and the average particle size was found to be 55 μm.

(Calcination of Classified Product)

The obtained classified product was supplied at a supply rate of 20 kg/hr to a cylindrical calcination tube made of SUS (inside diameter: 500 mm, length: 3500 mm, wall thickness: 20 mm), in which 7 weir plates each having a height of 150 mm were placed to divide the length of a heating furnace portion into 8 equal parts. Then, the heating furnace temperature was controlled to achieve a temperature profile, in which while the calcination tube was rotated at a rotation rate of 4 rotations/min under nitrogen gas circulation of 600 N/liter/min, the temperature was increased to 370° C. over approximately 4 hours, and the temperature was then retained at 370° C. for 3 hours. Thereafter, pre-stage calcination was carried out on the classified product, so as to obtain a pre-stage calcined product. The pre-stage calcined product was supplied at a supply rate of 15 kg/hr to another calcination tube made of SUS (inside diameter: 500 mm, length: 3500 mm, wall thickness: 20 mm), in which 7 weir plates each having a height of 150 mm were placed to divide the length of a heating furnace portion into 8 equal parts, while the calcination tube was rotate at a rate of 4 rotations/min. In this operation, while impacts were given from the direction vertical to the rotation axis that was at a height of 250 mm above the calcination tube to a portion on the pre-stage calcined product introduction side of the calcinations tube, at a rate of one impact every 5 seconds, with the use of a hammering device equipped with a hammer with a mass of 14 kg, the tip of the impact portion of which was made of SUS, the heating furnace temperature was controlled to achieve a temperature profile in which the temperature of the calcinations tube was increased to 680° C. at a rate of 2° C./min under nitrogen gas circulation of 500 N/liter/min, calcinations was then carried out at 680° C. for 2 hours, and the temperature was then decreased at a rate of 1° C./min. Then, main calcination was carried out on the pre-stage calcined product, so as to obtain an oxide catalyst.

(Removal of Protruding Portions)

While air was supplied to a vertical tube (inside diameter: 41.6 mm, length: 70 cm) comprising a perforated disk having three holes with a diameter of 1/64 inches at the bottom thereof and a paper filter at the upper portion thereof, 50 g of the oxide catalyst was poured therein. In this operation, the length of air current in the direction in which the air current flowed was 52 mm, and the average linear velocity of the air current was 310 m/s. Twenty-four hours later, the obtained oxide catalyst was observed by SEM. As a result, no protruding portions could be confirmed on the surface of the oxide catalyst.

(Ammoxidation Reaction of Propane)

Using the above obtained oxide catalyst, propane was subjected to a vapor phase ammoxidation reaction by the following method. That is, a Vycor glass fluidized bed reaction tube with an inside diameter of 25 mm was filled with 35 g of the oxide catalyst, and the reaction temperature was set at 440° C. and the reaction pressure was set at ordinary pressure. Thereafter, mixed gas consisting of propane, ammonia, oxygen and helium (propane:ammonia:oxygen:helium=1:1:3:18 (molar ratio)) was supplied at a constant time of 2.8 (sec·g/cc). After completion of the reaction, the propane conversion was found to be 89.5%, and the yield of acrylonitrile was found to be 53.5%.

Example 7

Preparation of Niobium Raw Material Solution

A niobium raw material solution was prepared in the same manner as that of Example 1.

(Preparation of Aqueous Mixed Solution in Large Mixed Solution Tank)

Instead of the two mixed solution tanks 110, there was used a mixed solution tank 310 comprising a large dedicated preparation tank (hereinafter referred to as a "large mixed solution tank") 302, two dedicated storage tanks (hereinafter referred to as "small mixed solution tanks") 304 that were smaller than the large dedicated preparation tank 302, and a pipe L30 for connecting them, as shown in FIG. 6. As materials for the inner surfaces of the large mixing tank 302 and the two small mixing tanks 304, and as a material for a portion in the pipe L30 that was allowed to come into contact with an aqueous mixed solution, a fluorocarbon resin (trade name: "Teflon PTFE," manufactured by Du Pont-Mitsui Fluorochemicals Co., Ltd.) was used. Other than these exceptions, an apparatus for producing a catalyst comprising the same configuration as that of Example 6 was used.

First, fouling attached to the inside of the large mixed solution tank 302 was washed by a washing device 118 positioned in an upper portion in the large mixed solution tank 302 for 15 minutes. Moreover, 600 kg of hot water of 50° C. was poured via a raw material supplying port 112 into the large mixed solution tank 302, and it was then stirred and mixed by a stirrer 116 for 5 minutes, so that the large mixed solution tank 302 was washed with water.

Subsequently, 150 kg of water, 45.42 kg of ammonium heptamolybdate [$(NH_4)_6Mo_7O_{24} \cdot 4H_2O$], 6.321 kg of ammonium metavanadate [$NH_4VO_3$], 8.28 kg of diantimony trioxide [$Sb_2O_3$], and a cerium nitrate aqueous solution prepared by dissolving 558 g of cerium nitrate [$Ce(NO_3)_3 \cdot 6H_2O$] in 39 kg of water were poured via a raw material supplying port 112 into the large mixed solution tank 302, and the obtained mixed solution was then heated at 95° C. for 1 hour while stirring, so as to obtain an aqueous raw material solution (I).

Meanwhile, 5.84 kg of a hydrogen peroxide solution containing 30% by mass of $H_2O_2$ was added to 44.1 kg of the above described niobium raw material solution in another vessel. The solution temperature was maintained at approximately 20° C., and the solution was stirred and mixed, so as to obtain an aqueous raw material solution (II).

The obtained aqueous raw material solution (I) was cooled to 70° C. in the large mixed solution tank 302, and 89.9 kg of silica sol containing 30.2% by mass of $SiO_2$ was then added thereto. Subsequently, 9.68 kg of a hydrogen peroxide solution containing 30% by mass of $H_2O_2$ was added to the reaction solution, and the obtained solution was then stirred and mixed at 55° C. for 30 minutes. Thereafter, a total amount of the above described aqueous raw material solution (II) and 3.59 kg of an ammonium metatungstate aqueous solution (50% aqueous solution) were further added to the reaction solution. Moreover, 22.2 kg of fumed silica dispersed in 322.1 kg of water was added to the solution, and the thus obtained mixed solution was then aged at 50° C. for 3 hours, so as to obtain an aqueous mixed solution (III). The time for preparing the aqueous mixed solution (III) in large mixed solution tank 302, which included water-washing, was 5 hours and 30 minutes. The obtained aqueous mixed solution (III) was supplied in almost half amount each to one of the two small mixed solution tanks 304 (hereinafter referred to as a "first small mixed solution tank 304") and the other small mixed solution tank (hereinafter referred to as a "second small mixed solution tank 304") through the pipe L30, and it was then stored in them. The time for supplying the aqueous mixed solution (III) to the first and second small mixed solution tanks 304 was 30 minutes.

(Spray-Drying from Small Mixed Solution Tank)

Before completion of the preparation of the aqueous mixed solution (III), the air heated to 210° C. and hot water at 50° C. adjusted to a supply of 80 kg/hr had been supplied to a centrifugal spray dryer, and the inlet temperature of the dryer had been set at 210° C. and the outlet temperature thereof had been set at 120° C. in advance.

After the supply of the aqueous mixed solution (III) from the large mixed solution tank 302 to the first small mixed solution tank 304 had been completed, the solution to be subjected to spray-drying was switched from hot water to the aqueous mixed solution (III) stored in the first small mixed solution tank 304. In order to prevent fluctuation in the outlet temperature of the dryer 120, the amount of the aqueous mixed solution (III) supplied to the dryer 120 was controlled. As a result, the supply rate became 100 kg/Hr. The spray-drying was continued for 3 hours, and during this operation, the outlet temperature was 120±5° C., and thus, there was no significant fluctuation. Immediately after the spray-drying of the aqueous mixed solution (III) stored in the first small mixed solution tank 304 had been completed, it was switched to the spray-drying of the aqueous mixed solution (III) stored in the second small mixed solution tank 304. The time for spray-drying the aqueous mixed solution (III) stored in the second small mixed solution tank 304 was also 3 hours. After completion of the spray-drying, water was supplied from the dryer 120 to the small mixed solution tanks 304, and the backwashing of the filters 140 was then carried out for 5 minutes.

(Preparation of Aqueous Mixed Solution in Large Mixed Solution Tank)

Immediately after the preparation of the aqueous mixed solution (III) in the large mixed solution tank 302 and the supply of the prepared solution to the first and second small mixed solution tanks 304 had been completed, and the solution to be supplied to the dryer 120 had been switched from hot water to the aqueous mixed solution (III) stored in the first small mixed solution tank 304, the preparation of the aqueous mixed solution (III) in the large mixed solution tank 304 was initiated.

As described above, the spray-drying of the aqueous mixed solution (III) from the first small mixed solution tank 304 and the spray-drying of the aqueous mixed solution (III) from the second small mixed solution tank 304 were repeatedly carried out, so that continuous spray-drying could be carried out substantially without interrupting spray-drying. The amount of dry products obtained by the continuous spray-drying for 1 month was 28.60 tons, while a theoretical recovered amount calculated from the fed amount was 29.64 tons. The recovery rate was found to be 96.5%.

(Measurement of Ultraviolet-Visible Reflection Spectrum)

The obtained dry product was sampled every other day. Thereafter, a ultraviolet-visible reflection spectrum that targeted 0.5 g out of the obtained 10 sample products was measured according to a diffuse reflection method in a wavelength range from 200 to 800 nm, using a UV/VIS spectrometer manufactured by JASCO Corporation (product name: "JASCO UV/VIS Spectrometer V-650"). As a baseline standard, "Spectralon" (product name) manufactured by Labspere was used. The maximum value of absorbance was found to be 1.02. The absorbance at a wavelength of 600 nm was 0.31 to 0.36. Referring to Japanese Patent Application Laid-Open No. 2011-005364, this was an absorbance in which high performance could be anticipated. Accordingly, total quantities of the obtained dry products were used in a classification operation without sorting them.

(Classification Operation)

The obtained dry products were classified using a sieve with a sieve size of 25 μm, so as to obtain a classified product. The content of particles with a size of 25 μm or less in the obtained classified product was found to be 0.8% by mass, and the average particle size was found to be 55 μm.

(Calcination of Classified Product)

The obtained classified product was calcined in the same manner as that of Example 1.

(Removal of Protruding Portions)

Removal of protruding portions was carried out in the same manner as that of Example 1. Twenty-four hours later, the obtained oxide catalyst was observed by SEM. As a result, no protruding portions could be confirmed on the surface of the oxide catalyst.

(Ammoxidation Reaction of Propane)

Using the above obtained oxide catalyst, propane was subjected to a vapor phase ammoxidation reaction by the following method. That is, a Vycor glass fluidized bed reaction tube with an inside diameter of 25 mm was filled with 35 g of the oxide catalyst, and the reaction temperature was set at 440° C. and the reaction pressure was set at ordinary pressure. Thereafter, mixed gas consisting of propane, ammonia, oxygen and helium (propane:ammonia:oxygen:helium=1:1:3:18 (molar ratio)) was supplied at a constant time of 2.8 (sec·g/cc). After completion of the reaction, the propane conversion was found to be 89.2%, and the yield of acrylonitrile was found to be 53.4%.

Comparative Example 1

Preparation of Niobium Raw Material Solution

A niobium raw material solution was prepared in the same manner as that of Example 1.

(Preparation of Aqueous Mixed Solution)

There was used an apparatus for producing a catalyst comprising the same configuration as that of Example 1 with the exception that it did not comprise a filter 140.

First, fouling attached to the inside of the mixed solution tank 110 was washed by a washing device 118 positioned in an upper portion of the mixed solution tank 110 for 1 hour. Thereafter, 300 kg of hot water of 50° C. was poured via a raw material supplying port 112 into the mixed solution tank 110, and it was then stirred and mixed by a stirrer 116 for 5 minutes, so that the mixed solution tank 110 was washed with water.

Subsequently, 100 kg of water, 30.28 kg of ammonium heptamolybdate [$(NH_4)_6Mo_7O_{24}\cdot 4H_2O$], 4.214 kg of ammonium metavanadate [$NH_4VO_3$], 5.52 kg of diantimony trioxide [$Sb_2O_3$], and a cerium nitrate aqueous solution prepared by dissolving 372 g of cerium nitrate [$Ce(NO_3)_3\cdot 6H_2O$] in 26 kg of water were poured via the raw material supplying port 112 into the mixed solution tank was then heated at 95° C. for 1 hour while stirring, so as to obtain an aqueous raw material solution (I).

Meanwhile, 3.89 kg of a hydrogen peroxide solution containing 30% by mass of $H_2O_2$ was added to 29.4 kg of the above described niobium raw material solution in another vessel. The solution temperature was maintained at approximately 20° C., and the solution was stirred and mixed, so as to obtain an aqueous raw material solution (II).

The obtained aqueous raw material solution (I) was cooled to 70° C. in the mixed solution tank 110, and 59.9 kg of silica sol containing 30.2% by mass of $SiO_2$ was then added thereto. Subsequently, 6.45 kg of a hydrogen peroxide solution containing 30% by mass of $H_2O_2$ was added to the reaction solution, and the obtained solution was then stirred and mixed at 55° C. for 30 minutes. Thereafter, a total amount of the above described aqueous raw material solution (II) and 2.39 kg of an ammonium metatungstate aqueous solution (50% aqueous solution) were further added to the reaction solution. Moreover, 14.8 kg of fumed silica dispersed in 214.7 kg of water was added to the solution, and the thus obtained mixed solution was then aged in an atmosphere having a gas phase oxygen concentration of 18 vol % at 50° C. for 1 hour, so as to obtain an aqueous mixed solution (III) (viscosity at 50° C.: 5.0 cp). It is to be noted that $Pv=1.0$ $kW/m^3$ as a stirring condition.

(Spray-Drying of Aqueous Mixed Solution Obtained in Mixed Solution Tank)

Before completion of the preparation of the aqueous mixed solution (III), the air heated to 210° C. and hot water at 50° C. adjusted to a supply of 80 kg/hr had been supplied via a nozzle to the spray dryer 120, and the inlet temperature of the dryer 120 had been set at 210° C. and the outlet temperature thereof had been set at 120° C. in advance.

After completion of the preparation of the aqueous mixed solution (III) in the mixed solution tank 110, a solution to be supplied to the dryer 120 was immediately switched from hot water to the aqueous mixed solution (III) which was to be supplied from the mixed solution tank 110. The aqueous mixed solution (III) was passed through the pipe L10 and the pump 160, and it was then supplied to the dryer 120. In order to prevent fluctuation in the outlet temperature, the amount of the aqueous mixed solution (III) supplied to spray dryer 120 was controlled. As a result, the supply rate became 100 kg/hr. During this operation, the outlet temperature was 120±5° C., and thus there was no significant fluctuation.

As described above, the operation from the preparation step in the mixed solution tank 110 to the drying step performed in the spray dryer 120 was repeatedly carried out for 1 month. The amount of dry products obtained for 1 month was 23.95 tons, while a theoretical recovered amount calculated from the fed amount was 29.64 tons. The recovery rate was found to be 80.8%.

(Measurement of Ultraviolet-Visible Reflection Spectrum)

The obtained dry product was sampled every other day. Thereafter, a ultraviolet-visible reflection spectrum that targeted 0.5 g out of the obtained 10 sample products was measured according to a diffuse reflection method in a wavelength range from 200 to 800 nm, using a UV/VIS spectrometer manufactured by JASCO Corporation (product name: "JASCO UV/VIS Spectrometer V-650"). As a baseline standard, "SpectraIon" (product name) manufactured by Labspere was used. The maximum value of absorbance was found to be 1.02. The absorbance at a wavelength of 600 nm was 0.31 to 0.36. Referring to Japanese Patent Application Laid-Open No. 2011-005364, this was an absorbance in which high performance could be anticipated. Accordingly, total quantities of the obtained dry products were used in a classification operation without sorting them.

(Classification Operation)

The obtained dry products were classified using a sieve with a sieve size of 25 μm, so as to obtain a classified product. The content of particles with a size of 25 μm or less in the obtained classified product was found to be 6.2% by mass, and the average particle size was found to be 39 μm.

(Calcination of Classified Product)

The obtained classified product was calcined in the same manner as that of Example 1.

(Removal of Protruding Portions)

Removal of protruding portions was carried out in the same manner as that of Example 1. Twenty-four hours later, the obtained oxide catalyst was observed by SEM. As a result, no protruding portions could be confirmed on the surface of the oxide catalyst.

(Ammoxidation Reaction of Propane)

Using the above obtained oxide catalyst, propane was subjected to a vapor phase ammoxidation reaction by the following method. That is, a Vycor glass fluidized bed reaction tube with an inside diameter of 25 mm was filled with 35 g of the oxide catalyst, and the reaction temperature was set at 440° C. and the reaction pressure was set at ordinary pressure. Thereafter, mixed gas consisting of propane, ammonia, oxygen and helium (propane:ammonia:oxygen:helium=1:1:3:18 (molar ratio)) was supplied at a constant time of 2.8 (sec·g/cc). After completion of the reaction, the propane conversion was found to be 87.0%, and the yield of acrylonitrile was found to be 49.8%.

Comparative Example 2

Preparation of Niobium Raw Material Solution

A niobium raw material solution was prepared in the same manner as that of Example 1.

(Preparation of Aqueous Mixed Solution)

The same apparatus for producing a catalyst as that of Comparative Example 1 was used.

First, 300 kg of hot water of 50° C. was poured via a raw material supplying port 112 into the mixed solution tank 110, and it was then stirred and mixed by a stirrer 116 for 5 minutes, so that the mixed solution tank 110 was washed with water.

Subsequently, 100 kg of water, 30.28 kg of ammonium heptamolybdate $[(NH_4)_6Mo_7O_{24}.4H_2O]$, 4.214 kg of ammonium metavanadate $[NH_4VO_3]$, 5.52 kg of diantimony trioxide $[Sb_2O_3]$, and a cerium nitrate aqueous solution prepared by dissolving 372 g of cerium nitrate $[Ce(NO_3)_3.6H_2O]$ in 26 kg of water were poured via the raw material supplying port 112 into the mixed solution tank was then heated at 95° C. for 1 hour while stirring, so as to obtain an aqueous raw material solution (I).

Meanwhile, 3.89 kg of a hydrogen peroxide solution containing 30% by mass of $H_2O_2$ was added to 29.4 kg of the above described niobium raw material solution in another vessel. The solution temperature was maintained at approximately 20° C., and the solution was stirred and mixed, so as to obtain an aqueous raw material solution (II).

The obtained aqueous raw material solution (I) was cooled to 70° C. in the mixed solution tank 110, and 59.9 kg of silica sol containing 30.2% by mass of $SiO_2$ was then added thereto. Subsequently, 6.45 kg of a hydrogen peroxide solution containing 30% by mass of $H_2O_2$ was added to the reaction solution, and the obtained solution was then stirred and mixed at 55° C. for 30 minutes. Thereafter, a total amount of the above described aqueous raw material solution (II) and 2.39 kg of an ammonium metatungstate aqueous solution (50% aqueous solution) were further added to the reaction solution. Moreover, 14.8 kg of fumed silica dispersed in 214.7 kg of water was added to the solution, and the thus obtained mixed solution was then aged in an atmosphere having a gas phase oxygen concentration of 18 vol % at 50° C. for 1 hour, so as to obtain an aqueous mixed solution (III) (viscosity at 50° C.: 5.0 cp). It is to be noted that $Pv=1.0$ $kW/m^3$ as a stirring condition.

(Spray-Drying of Aqueous Mixed Solution Obtained in Mixed Solution Tank)

Before completion of the preparation of the aqueous mixed solution (III), the air heated to 210° C. and hot water at 50° C. adjusted to a supply of 80 kg/hr had been supplied via a nozzle to the spray dryer 120, and the inlet temperature of the dryer 120 had been set at 210° C. and the outlet temperature thereof had been set at 120° C. in advance.

After completion of the preparation of the aqueous mixed solution (III) in the mixed solution tank 110, a solution to be supplied to the dryer 120 was immediately switched from hot water to the aqueous mixed solution (III) which was to be supplied from the mixed solution tank 110. The aqueous mixed solution (III) was passed through the pipe L10 and the pump 160, and it was then supplied to the dryer 120. In order to prevent fluctuation in the outlet temperature, the amount of the aqueous mixed solution (III) supplied to spray dryer 120 was controlled. As a result, the supply rate became 100 kg/hr. During this operation, the outlet temperature was 120±5° C., and thus there was no significant fluctuation.

As described above, the operation from the preparation step in the mixed solution tank 110 to the drying step performed in the spray dryer 120 was repeatedly carried out for 1 month. The amount of dry products obtained for 1 month was 22.23 tons, while a theoretical recovered amount calculated from the fed amount was 29.64 tons. The recovery rate was found to be 75.0%.

(Measurement of Ultraviolet-Visible Reflection Spectrum)

The obtained dry product was sampled every other day. Thereafter, a ultraviolet-visible reflection spectrum that targeted 0.5 g out of the obtained 10 sample products was measured according to a diffuse reflection method in a wavelength range from 200 to 800 nm, using a UV/VIS spectrometer manufactured by JASCO Corporation (product name: "JASCO UV/VIS Spectrometer V-650"). As a baseline standard, "SpectraIon" (product name) manufactured by Labspere was used. The maximum value of absorbance was found to be 1.02. The absorbance at a wavelength of 600 nm was 0.31 to 0.36. Referring to Japanese Patent Application Laid-Open No. 2011-005364, this was an absorbance in which high performance could be anticipated. Accordingly, total quantities of the obtained dry products were used in a classification operation without sorting them.

(Classification Operation)

The obtained dry products were classified using a sieve with a sieve size of 25 μm, so as to obtain a classified product. The content of particles with a size of 25 μm or less in the obtained classified product was found to be 7.2% by mass, and the average particle size was found to be 35 μm.

(Calcination of Classified Product)

The obtained classified product was calcined in the same manner as that of Example 1.

(Removal of Protruding Portions)

Removal of protruding portions was carried out in the same manner as that of Example 1. Twenty-four hours later, the obtained oxide catalyst was observed by SEM. As a result, no protruding portions could be confirmed on the surface of the oxide catalyst.

(Ammoxidation Reaction of Propane)

Using the above obtained oxide catalyst, propane was subjected to a vapor phase ammoxidation reaction by the following method. That is, a Vycor glass fluidized bed reaction tube with an inside diameter of 25 mm was filled with 35 g of the oxide catalyst, and the reaction temperature was set at 440° C. and the reaction pressure was set at ordinary pressure. Thereafter, mixed gas consisting of propane, ammonia, oxygen and helium (propane:ammonia:oxygen:helium=1:1:3:18 (molar ratio)) was supplied at a constant time of 2.8 (sec·g/cc). After completion of the reaction, the propane conversion was found to be 86.2%, and the yield of acrylonitrile was found to be 49.1%.

Comparative Example 3

Preparation of Niobium Raw Material Solution

A niobium raw material solution was prepared in the same manner as that of Example 1.

(Preparation of Aqueous Mixed Solution)

As a temperature control device 150 having both heating and cooling functions (pipe system heating/cooling equipment), a heat exchanger having the same heat-transfer pipe 154 as that shown in FIG. 2 was used, and stainless steel was adopted as a material for the heat-transfer pipe 154. As a material for the inner surface of a mixed solution tank 110, and as a material for a portion of a pipe L10 that was allowed to come into contact with an aqueous mixed solution, stainless steel was used. Other than these exceptions, an apparatus for producing a catalyst comprising the same configuration as that of Comparative Example 1 was used.

First, fouling attached to the inside of the mixed solution tank 110 was washed by a washing device 118 positioned in an upper portion of the mixed solution tank 110 for 1 hour. Thereafter, 300 kg of hot water of 50° C. was poured via a raw material supplying port 112 into the mixed solution tank 110, and it was then stirred and mixed by a stirrer 116 for 5 minutes, so that the mixed solution tank 110 was washed with water.

Subsequently, 100 kg of water, 30.28 kg of ammonium heptamolybdate $[(NH_4)_6Mo_7O_{24}.4H_2O]$, 4.214 kg of ammonium metavanadate $[NH_4VO_3]$, 5.52 kg of diantimony trioxide $[Sb_2O_3]$, and a cerium nitrate aqueous solution prepared by dissolving 372 g of cerium nitrate $[Ce(NO_3)_3.6H_2O]$ in 26 kg of water were poured via the raw material supplying port 112 into the mixed solution tank was then heated at 95° C. for 1 hour while stirring, so as to obtain an aqueous raw material solution (I).

Meanwhile, 3.89 kg of a hydrogen peroxide solution containing 30% by mass of $H_2O_2$ was added to 29.4 kg of the above described niobium raw material solution in another vessel. The solution temperature was maintained at approximately 20° C., and the solution was stirred and mixed, so as to obtain an aqueous raw material solution (II).

The obtained aqueous raw material solution (I) was cooled to 70° C. in the mixed solution tank 110, and 59.9 kg of silica sol containing 30.2% by mass of $SiO_2$ was then added thereto. Subsequently, 6.45 kg of a hydrogen peroxide solution containing 30% by mass of $H_2O_2$ was added to the reaction solution, and the obtained solution was then stirred and mixed at 55° C. for 30 minutes. Thereafter, a total amount of the above described aqueous raw material solution (II) and 2.39 kg of an ammonium metatungstate aqueous solution (50% aqueous solution) were further added to the reaction solution. Moreover, 14.8 kg of fumed silica dispersed in 214.7 kg of water was added to the solution, and the thus obtained mixed solution was then aged in an atmosphere having a gas phase oxygen concentration of 18 vol % at 50° C. for 1 hour, so as to obtain an aqueous mixed solution (III) (viscosity at 50° C.: 5.0 cp). It is to be noted that Pv=1.0 kW/m³ as a stirring condition.

(Spray-Drying of Aqueous Mixed Solution Obtained in Mixed Solution Tank)

Before completion of the preparation of the aqueous mixed solution (III), the air heated to 210° C. and hot water at 50° C.

adjusted to a supply of 80 kg/hr had been supplied via a nozzle to the spray dryer 120, and the inlet temperature of the dryer 120 had been set at 210° C. and the outlet temperature thereof had been set at 120° C. in advance.

After completion of the preparation of the aqueous mixed solution (III) in the mixed solution tank 110, a solution to be supplied to the dryer 120 was immediately switched from hot water to the aqueous mixed solution (III) which was to be supplied from the mixed solution tank 110. The aqueous mixed solution (III) was passed through the pipe L10 and the pump 160, and was then supplied to the dryer 120. In order to prevent fluctuation in the outlet temperature, the amount of the aqueous mixed solution (III) supplied to spray dryer 120 was controlled. As a result, the supply rate became 100 kg/hr. During this operation, the outlet temperature was 120±5° C., and thus there was no significant fluctuation.

As described above, the operation from the preparation step in the mixed solution tank 110 to the backwashing of the filter 140 was repeatedly carried out for 1 month. The amount of dry products obtained for 1 month was 22.20 tons, while a theoretical recovered amount calculated from the fed amount was 29.64 tons. The recovery rate was found to be 74.9%.

(Measurement of Ultraviolet-Visible Reflection Spectrum)

The obtained dry product was sampled every other day. Thereafter, a ultraviolet-visible reflection spectrum that targeted 0.5 g out of the obtained 10 sample products was measured according to a diffuse reflection method in a wavelength range from 200 to 800 nm, using a UV/VIS spectrometer manufactured by JASCO Corporation (product name: "JASCO UV/VIS Spectrometer V-650"). As a baseline standard, "SpectraIon" (product name) manufactured by Labspere was used. The maximum value of absorbance was found to be 1.02. The absorbance at a wavelength of 600 nm was 0.31 to 0.36. Referring to Japanese Patent Application Laid-Open No. 2011-005364, this was an absorbance in which high performance could be anticipated. Accordingly, total quantities of the obtained dry products were used in a classification operation without sorting them.

(Classification Operation)

The obtained dry products were classified using a sieve with a sieve size of 25 μm, so as to obtain a classified product. The content of particles with a size of 25 μm or less in the obtained classified product was found to be 7.5% by mass, and the average particle size was found to be 35 μm.

(Calcination of Classified Product)

The obtained classified product was calcined in the same manner as that of Example 1.

(Removal of Protruding Portions)

Removal of protruding portions was carried out in the same manner as that of Example 1. Twenty-four hours later, the obtained oxide catalyst was observed by SEM. As a result, no protruding portions could be confirmed on the surface of the oxide catalyst.

(Ammoxidation Reaction of Propane)

Using the above obtained oxide catalyst, propane was subjected to a vapor phase ammoxidation reaction by the following method. That is, a Vycor glass fluidized bed reaction tube with an inside diameter of 25 mm was filled with 35 g of the oxide catalyst, and the reaction temperature was set at 440° C. and the reaction pressure was set at ordinary pressure. Thereafter, mixed gas consisting of propane, ammonia, oxygen and helium (propane:ammonia:oxygen:helium=1:1:3:18 (molar ratio)) was supplied at a constant time of 2.8 (sec·g/cc). After completion of the reaction, the propane conversion was found to be 86.0%, and the yield of acrylonitrile was found to be 49.0%.

Comparative Example 4

Preparation of Niobium Raw Material Solution

A niobium raw material solution was prepared in the same manner as that of Example 1.

(Preparation of Aqueous Mixed Solution)

The same apparatus for producing a catalyst as that of Comparative Example 3 was used.

First, 300 kg of hot water of 50° C. was poured via a raw material supplying port 112 into the mixed solution tank 110, and it was then stirred and mixed by a stirrer 116 for 5 minutes, so that the mixed solution tank 110 was washed with water.

Subsequently, 100 kg of water, 30.28 kg of ammonium heptamolybdate [$(NH_4)_6Mo_7O_{24}.4H_2O$], 4.214 kg of ammonium metavanadate [$NH_4VO_3$], 5.52 kg of diantimony trioxide [$Sb_2O_3$], and a cerium nitrate aqueous solution prepared by dissolving 372 g of cerium nitrate [$Ce(NO_3)_3.6H_2O$] in 26 kg of water were poured via the raw material supplying port 112 into the mixed solution tank was then heated at 95° C. for 1 hour while stirring, so as to obtain an aqueous raw material solution (I).

Meanwhile, 3.89 kg of a hydrogen peroxide solution containing 30% by mass of $H_2O_2$ was added to 29.4 kg of the above described niobium raw material solution in another vessel. The solution temperature was maintained at approximately 20° C., and the solution was stirred and mixed, so as to obtain an aqueous raw material solution (II).

The obtained aqueous raw material solution (I) was cooled to 70° C. in the mixed solution tank 110, and 59.9 kg of silica sol containing 30.2% by mass of $SiO_2$ was then added thereto. Subsequently, 6.45 kg of a hydrogen peroxide solution containing 30% by mass of $H_2O_2$ was added to the reaction solution, and the obtained solution was then stirred and mixed at 55° C. for 30 minutes. Thereafter, a total amount of the above described aqueous raw material solution (II) and 2.39 kg of an ammonium metatungstate aqueous solution (50% aqueous solution) were further added to the reaction solution. Moreover, 14.8 kg of fumed silica dispersed in 214.7 kg of water was added to the solution, and the thus obtained mixed solution was then aged in an atmosphere having a gas phase oxygen concentration of 18 vol % at 50° C. for 1 hour, so as to obtain an aqueous mixed solution (III) (viscosity at 50° C.: 5.0 cp). It is to be noted that Pv=1.0 kW/m$^3$ as a stirring condition.

(Spray-Drying of Aqueous Mixed Solution Obtained in Mixed Solution Tank)

Before completion of the preparation of the aqueous mixed solution (III), the air heated to 210° C. and hot water at 50° C. adjusted to a supply of 80 kg/hr had been supplied via a nozzle to the spray dryer 120, and the inlet temperature of the dryer 120 had been set at 210° C. and the outlet temperature thereof had been set at 120° C. in advance.

After completion of the preparation of the aqueous mixed solution (III) in the mixed solution tank 110, a solution to be supplied to the dryer 120 was immediately switched from hot water to the aqueous mixed solution (III) which was to be supplied from the mixed solution tank 110. The aqueous mixed solution (III) was passed through the pipe L10 and the pump 160, and was then supplied to the dryer 120. In order to prevent fluctuation in the outlet temperature, the amount of the aqueous mixed solution (III) supplied to spray dryer 120 was controlled. As a result, the supply rate became 100 kg/hr. During this operation, the outlet temperature was 120±5° C., and thus there was no significant fluctuation.

As described above, the operation from the preparation step in the mixed solution tank 110 to the backwashing of the filter 140 was repeatedly carried out for 1 month. The amount of dry products obtained for 1 month was 20.81 tons, while a theoretical recovered amount calculated from the fed amount was 29.64 tons. The recovery rate was found to be 70.2%.

(Measurement of Ultraviolet-Visible Reflection Spectrum)

The obtained dry product was sampled every other day. Thereafter, a ultraviolet-visible reflection spectrum that targeted 0.5 g out of the obtained 10 sample products was measured according to a diffuse reflection method in a wavelength range from 200 to 800 nm, using a UV/VIS spectrometer manufactured by JASCO Corporation (product name: "JASCO UV/VIS Spectrometer V-650"). As a baseline standard, "SpectraIon" (product name) manufactured by Labspere was used. The maximum value of absorbance was found to be 1.02. The absorbance at a wavelength of 600 nm was 0.31 to 0.36. Referring to Japanese Patent Application Laid-Open No. 2011-005364, this was an absorbance in which high performance could be anticipated. Accordingly, total quantities of the obtained dry products were used in a classification operation without sorting them.

(Classification Operation)

The obtained dry products were classified using a sieve with a sieve size of 25 μm, so as to obtain a classified product. The content of particles with a size of 25 μm or less in the obtained classified product was found to be 9.3% by mass, and the average particle size was found to be 30 μm.

(Calcination of Classified Product)

The obtained classified product was calcined in the same manner as that of Example 1.

(Removal of Protruding Portions)

Removal of protruding portions was carried out in the same manner as that of Example 1. Twenty-four hours later, the obtained oxide catalyst was observed by SEM. As a result, no protruding portions could be confirmed on the surface of the oxide catalyst.

(Ammoxidation Reaction of Propane)

Using the above obtained oxide catalyst, propane was subjected to a vapor phase ammoxidation reaction by the following method. That is, a Vycor glass fluidized bed reaction tube with an inside diameter of 25 mm was filled with 35 g of the oxide catalyst, and the reaction temperature was set at 440° C. and the reaction pressure was set at ordinary pressure. Thereafter, mixed gas consisting of propane, ammonia, oxygen and helium (propane:ammonia:oxygen:helium=1:1:3:18 (molar ratio)) was supplied at a constant time of 2.8 (sec·g/cc). After completion of the reaction, the propane conversion was found to be 84.8%, and the yield of acrylonitrile was found to be 48.4%.

According to the present invention, there can be provided: an apparatus and a method for producing a catalyst, which are capable of smoothly supplying the prepared aqueous mixed solution to a dryer; and a method for producing an unsaturated acid or an unsaturated nitrile using the aforementioned catalyst.

The present application is based on the Japanese patent application (Japanese Patent Application No. 2010-282346) filed on Dec. 17, 2010, and the Japanese patent application (Japanese Patent Application No. 2011-006328) filed on Jan. 14, 2011; the disclosure of each of which is hereby incorporated by reference.

DESCRIPTION OF SYMBOLS

100: apparatus for producing a catalyst, 110: mixed solution tank, 112: raw material supplying port, 114: aqueous mixed solution discharging port, 116: stirrer, 118: washing device, 120: dryer, 122: nozzle, 124: dry chamber, 126: dry product discharging port, 130, 150: temperature control device, 140: filter, 160: pump, L10: pipe.

What is claimed is:

1. An apparatus for producing a catalyst, comprising a tank configured to prepare an aqueous mixed solution containing a Mo compound, a V compound and a Nb compound, a dryer configured to spray-dry the aqueous mixed solution, and a pipe for connecting the tank with the dryer so that the aqueous mixed solution can be supplied from the tank to the dryer, wherein
a heater configured to heat the aqueous mixed solution is provided in the tank and/or the pipe, and a filter configured to filtrate the aqueous mixed solution is provided in the pipe.

2. The apparatus for producing a catalyst according to claim 1, wherein at least a part of an inner surface of the tank and/or an inner surface of the pipe consist of a fluorocarbon resin.

3. The apparatus for producing a catalyst according to claim 2, wherein a cooler configured to cool the aqueous mixed solution is provided in the tank.

4. The apparatus for producing a catalyst according to claim 3, wherein at least a part of a region of the heater and/or the cooler provided in the tank, the region being allowed to come into contact with the aqueous mixed solution, consist of a fluorocarbon resin.

5. The apparatus for producing a catalyst according to claim 2, comprising, inside the tank, a washer configured to wash an inner surface of the tank.

6. The apparatus for producing a catalyst according to claim 5, wherein the washer is configured to spray and/or inject water into the tank so that the water is allowed to come into contact with the inner surface of the tank.

7. The apparatus for producing a catalyst according to claim 2, comprising a plurality of the tanks, wherein the tanks are configured so that the aqueous mixed solution prepared in one or more of the tanks is spray-dried by the dryer, and thereafter, the aqueous mixed solution prepared in other one or more of the tanks that are different from the former one or more of the tanks is spray-dried by the dryer.

8. A method for producing a catalyst using the apparatus for producing a catalyst according to claim 2, comprising:
(a) a step of preparing an aqueous mixed solution containing a Mo compound, a V compound and a Nb compound; and
(b) a step of drying the aqueous mixed solution by a dryer, wherein the apparatus for producing a catalyst comprises a plurality of tanks, and
the method comprises:
a step of, while spray-drying the aqueous mixed solution from one or more of the tanks, further preparing the aqueous mixed solution in other one or more of the tanks that are different from the former one or more of the tanks; and
a step of continuously spray-drying the aqueous mixed solution by supplying the aqueous mixed solution prepared in the other one or more of the tanks to the dryer and spray-drying the aqueous mixed solution, after the aqueous mixed solution from the former one or more of the tanks has been spray-dried.

9. The method for producing a catalyst according to claim 8, wherein the catalyst has a composition represented by the following general formula (1):

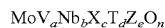  (1)

(wherein X represents one or more elements selected from the group consisting of Sb, Te, Sr, Ba, Sc, Y, La, Ce, Pr, Yb, W, Cr, Ta, Ti, Zr, Hf, Mn, Re, Fe, Ru, Co, Rh, Ni, Pd, Pt, Ag, Zn, B, Al, Ga, In, Ge, Sn, Pb, P, Bi, rare earth elements and alkaline earth elements; T represents one or more elements selected from the group consisting of Ti, Zr, Hf, Ta, Cr, W, Mn, Re, Fe, Co, Ni, Au, Zn, B, Al, Ga, In, Ge, Sn, Pb, P and Bi; Z represents one or more elements selected from the group consisting of La, Ce, Pr, Yb, Y, Sc, Sr and Ba; a, b, c, d and e are within the ranges of $0.01 \leq a \leq 1$, $0.01 \leq b \leq 1$, $0.01 \leq c \leq 1$, $0 \leq d < 1$, and $0 \leq e < 1$, respectively; and n is a value satisfying the balance of valences).

10. A method comprising carrying out a vapor-phase catalytic oxidation reaction or vapor-phase catalytic ammoxidation reaction of propane or isobutane so as to produce a corresponding unsaturated acid or unsaturated nitrile, wherein a catalyst obtained by the method for producing a catalyst according to claim 8 is used.

11. A method for producing a catalyst using the apparatus for producing a catalyst according to claim 2, wherein the catalyst has a composition represented by the following formula (1):

$$MoV_aNb_bX_cT_dZ_eO_n \qquad (1)$$

(wherein X represents one or more elements selected from the group consisting of Sb, Te, Sr, Ba, Sc, Y, La, Ce, Pr, Yb, W, Cr, Ta, Ti, Zr, Hf, Mn, Re, Fe, Ru, Co, Rh, Ni, Pd, Pt, Ag, Zn, B, Al, Ga, In, Ge, Sn, Pb, P, Bi, rare earth elements and alkaline earth elements; T represents one or more elements selected from the group consisting of Ti, Zr, Hf, Ta, Cr, W, Mn, Re, Fe, Co, Ni, Au, Zn, B, Al, Ga, In, Ge, Sn, Pb, P and Bi; Z represents one or more elements selected from the group consisting of La, Ce, Pr, Yb, Y, Sc, Sr and Ba; a, b, c, d and e are within the ranges of $0.01 \leq a \leq 1$, $0.01 \leq b \leq 1$, $0.01 \leq c \leq 1$, $0 \leq d < 1$, and $0 \leq e < 1$, respectively; and n is a value satisfying the balance of valences).

12. The apparatus for producing a catalyst according to claim 1, wherein a cooler configured to cool the aqueous mixed solution is provided in the tank.

13. The apparatus for producing a catalyst according to claim 12, wherein at least a part of a region of the heater and/or the cooler provided in the tank, the region being allowed to come into contact with the aqueous mixed solution, consist of a fluorocarbon resin.

14. The apparatus for producing a catalyst according to claim 1, comprising, inside the tank, a washer configured to wash an inner surface of the tank.

15. The apparatus for producing a catalyst according to claim 14, wherein the washer is configured to spray and/or inject water into the tank so that the water is allowed to come into contact with the inner surface of the tank.

16. The apparatus for producing a catalyst according to claim 1, comprising a plurality of the tanks, wherein the tanks are configured so that the aqueous mixed solution prepared in one or more of the tanks is spray-dried by the dryer, and thereafter, the aqueous mixed solution prepared in other one or more of the tanks that are different from the former one or more of the tanks is spray-dried by the dryer.

17. A method for producing a catalyst using the apparatus for producing a catalyst according to claim 1, comprising:
(a) a step of preparing an aqueous mixed solution containing a Mo compound, a V compound and a Nb compound; and
(b) a step of drying the aqueous mixed solution by a dryer, wherein the apparatus for producing a catalyst comprises a plurality of tanks, and
the method comprises:
a step of, while spray-drying the aqueous mixed solution from one or more of the tanks, further preparing the aqueous mixed solution in other one or more of the tanks that are different from the former one or more of the tanks; and
a step of continuously spray-drying the aqueous mixed solution by supplying the aqueous mixed solution prepared in the other one or more of the tanks to the dryer and spray-drying the aqueous mixed solution, after the aqueous mixed solution from the former one or more of the tanks has been spray-dried.

18. The method for producing a catalyst according to claim 17, wherein the catalyst has a composition represented by the following general formula (1):

$$MoV_aNb_bX_cT_dZ_eO_n \qquad (1)$$

(wherein X represents one or more elements selected from the group consisting of Sb, Te, Sr, Ba, Sc, Y, La, Ce, Pr, Yb, W, Cr, Ta, Ti, Zr, Hf, Mn, Re, Fe, Ru, Co, Rh, Ni, Pd, Pt, Ag, Zn, B, Al, Ga, In, Ge, Sn, Pb, P, Bi, rare earth elements and alkaline earth elements; T represents one or more elements selected from the group consisting of Ti, Zr, Hf, Ta, Cr, W, Mn, Re, Fe, Co, Ni, Au, Zn, B, Al, Ga, In, Ge, Sn, Pb, P and Bi; Z represents one or more elements selected from the group consisting of La, Ce, Pr, Yb, Y, Sc, Sr and Ba; a, b, c, d and e are within the ranges of $0.01 \leq a \leq 1$, $0.01 \leq b \leq 1$, $0.01 \leq c \leq 1$, $0 \leq d < 1$, and $0 \leq e < 1$, respectively; and n is a value satisfying the balance of valences).

19. A method comprising carrying out a vapor-phase catalytic oxidation reaction or vapor-phase catalytic ammoxidation reaction of propane or isobutane so as to produce a corresponding unsaturated acid or unsaturated nitrile, wherein a catalyst obtained by the method for producing a catalyst according to claim 17 is used.

20. A method for producing a catalyst using the apparatus for producing a catalyst according to claim 1, wherein the catalyst has a composition represented by the following formula (1):

$$MoV_aNb_bX_cT_dZ_eO_n \qquad (1)$$

(wherein X represents one or more elements selected from the group consisting of Sb, Te, Sr, Ba, Sc, Y, La, Ce, Pr, Yb, W, Cr, Ta, Ti, Zr, Hf, Mn, Re, Fe, Ru, Co, Rh, Ni, Pd, Pt, Ag, Zn, B, Al, Ga, In, Ge, Sn, Pb, P, Bi, rare earth elements and alkaline earth elements; T represents one or more elements selected from the group consisting of Ti, Zr, Hf, Ta, Cr, W, Mn, Re, Fe, Co, Ni, Au, Zn, B, Al, Ga, In, Ge, Sn, Pb, P and Bi; Z represents one or more elements selected from the group consisting of La, Ce, Pr, Yb, Y, Sc, Sr and Ba; a, b, c, d and e are within the ranges of $0.01 \leq a \leq 1$, $0.01 \leq b \leq 1$, $0.01 \leq c \leq 1$, $0 \leq d < 1$, and $0 \leq e < 1$, respectively; and n is a value satisfying the balance of valences).

* * * * *